(12) United States Patent
Dresser et al.

(10) Patent No.: US 12,059,316 B2
(45) Date of Patent: Aug. 13, 2024

(54) SYSTEMS AND METHODS FOR DENTAL TREATMENT AND VERIFICATION

(71) Applicant: Enamel Pure, Worcester, MA (US)

(72) Inventors: Charles Dresser, Wayland, MA (US); Nathan Monty, Shrewsbury, MA (US)

( * ) Notice: Subject to any disclaimer, the term of this patent is extended or adjusted under 35 U.S.C. 154(b) by 0 days.

(21) Appl. No.: 18/093,307

(22) Filed: Jan. 4, 2023

(65) Prior Publication Data
US 2024/0081966 A1 Mar. 14, 2024

Related U.S. Application Data

(60) Provisional application No. 63/404,953, filed on Sep. 8, 2022.

(51) Int. Cl.
| G06K 9/00 | (2022.01) |
| A61B 5/00 | (2006.01) |
| A61C 1/00 | (2006.01) |
| A61C 9/00 | (2006.01) |
| A61C 13/00 | (2006.01) |
| A61C 19/04 | (2006.01) |
| A61C 19/05 | (2006.01) |
| A61N 5/067 | (2006.01) |
| G06T 5/50 | (2006.01) |
| G06T 5/70 | (2024.01) |
| G06T 7/33 | (2017.01) |

(Continued)

(52) U.S. Cl.
CPC ............ *A61C 19/05* (2013.01); *A61B 5/0088* (2013.01); *A61C 1/0046* (2013.01); *A61C 9/0053* (2013.01); *A61C 13/0004* (2013.01); *A61C 19/04* (2013.01); *A61N 5/067* (2021.08); *G06T 5/50* (2013.01); *G06T 5/70* (2024.01); *G06T 7/33* (2017.01); *G16H 40/20* (2018.01); *G16H 50/70* (2018.01); *G06T 2207/10028* (2013.01); *G06T 2207/20081* (2013.01); *G06T 2207/30036* (2013.01)

(58) Field of Classification Search
None
See application file for complete search history.

(56) References Cited

U.S. PATENT DOCUMENTS

| 5,055,048 A | 10/1991 | Vassiliadis et al. |
| 5,275,564 A | 1/1994 | Vassiliadis et al. |
| 7,013,191 B2 | 3/2006 | Rubbert et al. |

(Continued)

FOREIGN PATENT DOCUMENTS

| AU | 2004223469 B2 | 7/2009 |
| AU | 2012206109 B2 | 2/2015 |

(Continued)

*Primary Examiner* — Wei Wen Yang

(57) ABSTRACT

Some aspects relate to systems and methods for dental treatment and verification. An exemplary system may include a laser configured to generate a laser beam as a function of a laser parameter, a beam delivery system configured to deliver the laser beam from the laser, a hand piece configured to accept the laser beam from the beam delivery system and direct the laser beam to dental tissue, a sensor configured to detect a treatment parameter as a function of a treatment phenomenon; and a computing device configured to receive the treatment parameter from the sensor; and determine aggregated treated surfaces as a function of the treatment parameter.

20 Claims, 28 Drawing Sheets

(51) Int. Cl.
*G16H 40/20* (2018.01)
*G16H 50/70* (2018.01)

(56) References Cited

U.S. PATENT DOCUMENTS

| | | |
|---|---|---|
| 7,090,497 B1 | 8/2006 | Harris et al. |
| 9,463,081 B2 | 10/2016 | Urakabe et al. |
| 9,864,485 B2 | 1/2018 | Patton et al. |
| 10,219,685 B2 | 3/2019 | Hakomori et al. |
| 10,390,913 B2 | 8/2019 | Sabina et al. |
| 10,506,929 B2 | 12/2019 | Almoumen et al. |
| 10,509,838 B2 | 12/2019 | Elbaz et al. |
| 10,850,115 B2 | 12/2020 | Zhou et al. |
| 11,357,404 B2 | 6/2022 | Atiya et al. |
| 11,357,603 B2 | 6/2022 | Elbaz et al. |
| 11,478,314 B1 | 10/2022 | Roh et al. |
| 2003/0158544 A1 | 8/2003 | Slatkine et al. |
| 2005/0259933 A1 | 11/2005 | Temelkuran et al. |
| 2007/0134615 A1 | 6/2007 | Lovely et al. |
| 2010/0009308 A1 | 1/2010 | Wen et al. |
| 2014/0272764 A1 | 9/2014 | Miller et al. |
| 2016/0012182 A1 | 1/2016 | Golay et al. |
| 2016/0113495 A1 | 4/2016 | Nanuundappa et al. |
| 2016/0135925 A1 | 5/2016 | Mason et al. |
| 2016/0143703 A1 | 5/2016 | Monty et al. |
| 2016/0154468 A1 | 6/2016 | Kimmel et al. |
| 2017/0215989 A1 | 8/2017 | Gregg et al. |
| 2018/0005377 A1* | 1/2018 | Alvarez ............... G06T 7/74 |
| 2018/0028065 A1 | 2/2018 | Elbaz et al. |
| 2018/0085002 A1 | 3/2018 | Glinec et al. |
| 2018/0356501 A1 | 12/2018 | Send et al. |
| 2019/0125250 A1 | 5/2019 | Monty et al. |
| 2019/0192262 A1 | 6/2019 | Pesach et al. |
| 2019/0247050 A1 | 8/2019 | Goldsmith et al. |
| 2019/0298448 A1* | 10/2019 | Kerbage ............... A61B 90/37 |
| 2019/0328489 A1 | 10/2019 | Richard et al. |
| 2020/0066391 A1 | 2/2020 | Sachdeva et al. |
| 2020/0214538 A1 | 7/2020 | Pesach et al. |
| 2020/0306011 A1 | 10/2020 | Chekhonin et al. |
| 2020/0315754 A1 | 10/2020 | Ciriello et al. |
| 2021/0137653 A1 | 5/2021 | Saphier et al. |
| 2021/0145538 A1 | 5/2021 | Boutoussov et al. |
| 2021/0196429 A1* | 7/2021 | Shojaei ................ A61C 7/002 |
| 2021/0205633 A1* | 7/2021 | Kerbage ............. A61N 5/0613 |
| 2021/0321872 A1 | 10/2021 | Saphier et al. |
| 2021/0353216 A1 | 11/2021 | Hillen et al. |
| 2021/0357688 A1* | 11/2021 | Kearney ................ G16H 50/70 |
| 2022/0023003 A1 | 1/2022 | Cramer et al. |
| 2022/0067943 A1* | 3/2022 | Claessen ................. G06T 7/00 |
| 2022/0249214 A1 | 8/2022 | Serval et al. |

FOREIGN PATENT DOCUMENTS

| | | |
|---|---|---|
| BR | 112021014639 A2 | 9/2021 |
| CN | 105358092 A | 2/2016 |
| CN | 107529968 A | 1/2018 |
| CN | 111083922 A | 4/2020 |
| CN | 211381887 U | 9/2020 |
| CN | 114302672 A | 4/2022 |
| EP | 2569748 A1 | 3/2013 |
| EP | 2204136 B1 | 8/2013 |
| EP | 3684292 A4 | 6/2021 |
| ES | 2758839 T3 | 5/2020 |
| JP | 6018618 B2 | 11/2016 |
| JP | 6262936 B2 | 1/2018 |
| JP | 6673703 B2 | 3/2020 |
| KR | 101277226 B1 | 6/2013 |
| KR | 101483216 B1 | 1/2015 |
| PH | 11999002531 B | 3/2002 |
| WO | 0009030 A1 | 2/2000 |
| WO | 0019929 A1 | 4/2000 |
| WO | 2018112273 A2 | 6/2018 |
| WO | 2019023631 A1 | 1/2019 |
| WO | 2019093426 A1 | 5/2019 |
| WO | 2019207588 A2 | 10/2019 |
| WO | 2021155054 A1 | 8/2021 |
| WO | 2022020267 A1 | 1/2022 |
| WO | 2022119930 A1 | 6/2022 |
| WO | 2022212507 A1 | 10/2022 |

\* cited by examiner

SYSTEMS AND METHODS FOR DENTAL TREATMENT AND VERIFICATION

CROSS-REFERENCE TO RELATED APPLICATIONS

This patent application is related to U.S. Provisional Patent Application Ser. No. 63/404,953, titled "DENTAL LASER SYSTEMS AND METHODS WITH CONCURRENT ANALYSIS FEATURES" filed on Sep. 8, 2022.

TECHNICAL FIELD

The present invention generally relates to the field of dentistry. In particular, the present invention is directed to dental laser systems and methods with concurrent analysis features.

BACKGROUND

The subject matter discussed in the background section should not be assumed to be prior art merely because of its mention in the background section. Similarly, a problem mentioned in the background section or associated with the subject matter of the background section should not be assumed to have been previously recognized in the prior art. The subject matter in the background section merely represents different approaches, which in and of themselves may also be inventions.

While many people have dental issues that necessitate replacement prostheses (such as crowns), many of these people choose not to have this procedure done because it is usually costly, time-consuming, and often ineffective. Additionally, traditional methods for creating restorative prostheses using physical dental impressions require a lot of work, are expensive, and take a long period. Improvements in computer-aided dentistry have aided the treatment of many patients. However, these technological improvements require additional equipment and slow workflow.

Further limitations and disadvantages of conventional approaches will become apparent to one of skill in the art, through the comparison of described systems with some aspects of the present disclosure, as outlined in the remainder of the present application and with reference to the drawings.

SUMMARY OF THE DISCLOSURE

A system and method for estimating future bite arrangement are provided substantially, as shown in and/or described in connection with at least one of the figures.

An aspect of the present disclosure relates to a system for estimating future bite arrangement includes a scheduling system, configured to schedule a patient for detecting a plurality of oral images representing a plurality of exposed tooth surfaces on a plurality of the patient's teeth, a sensor configured to periodically detect the plurality of oral images as a function of the schedule, and a computing device configured to: receive the plurality of oral images from the sensor, aggregate a first aggregated oral image as a function of the plurality of oral images at a first time, aggregate a second aggregated oral image as a function of the plurality of oral images at a second time, and estimate a future bite arrangement as a function of the first aggregated oral image and the second aggregated oral image.

In another aspect, a method of estimating future bite arrangement includes scheduling, using a scheduling system, a patient for detecting a plurality of oral images representing a plurality of exposed tooth surfaces on a plurality of the patient's teeth, periodically detecting, using a sensor, the plurality of oral images as a function of the schedule, receiving, using a computing device, the plurality of oral images from the sensor, aggregating, using the computing device, a first aggregated oral image as a function of the plurality of oral images at a first time, aggregating, using the computing device, a second aggregated oral image as a function of the plurality of oral images at a second time, and estimating, using the computing device, a future bite arrangement as a function of the first aggregated oral image and the second aggregated oral image.

In another aspect, a system for dental treatment and remote oversight includes a laser configured to generate a laser beam as a function of a laser parameter, a beam delivery system configured to deliver the laser beam from the laser, a hand piece configured to accept the laser beam from the beam delivery system and direct the laser beam to dental tissue, a sensor configured to detect a dental parameter as a function of a dental phenomenon, a computing device configured to receive the dental parameter from the sensor and communicate the dental parameter to a remote device configured to interface with a remote user. In some embodiments, the sensor comprises a camera and the dental parameter comprises an image of oral tissue. In some cases, the camera is located proximal to the hand piece, and the hand piece is further configured to facilitate an optical path between the oral tissue and the camera. In some cases, the optical path comprises one or more of a zinc sulfide lens, a calcium fluoride lens, a magnesium fluoride optic, a sodium chloride optic, a potassium bromide optic, or a barium fluoride optic. In some cases, the camera comprises a global shutter. In some embodiments, the beam delivery system comprises a beam scanner configured to scan the laser beam as a function of a scan parameter; wherein, the computing device is further configured to control the scan parameter. In some embodiments, the computing device is further configured to control the laser parameter. In some embodiments, the remote device is configured to communicate with a user of the system. In some cases, the remote device communicates by way of a network. In some cases, the network includes the Internet.

In some aspects, a method of dental treatment and remote oversight includes generating, using a laser configured, a laser beam as a function of a laser parameter, delivering, using a beam delivery system, the laser beam from the laser, accepting, using a hand piece, the laser beam from the beam delivery system, directing, using the hand piece, the laser beam to dental tissue, detecting, using a sensor, a dental parameter as a function of a dental phenomenon, receiving, using a computing device, the dental parameter from the sensor, and communicating, using the computing device, the dental parameter to a remote device configured to interface with a remote user. In some embodiments, the sensor comprises a camera and the dental parameter comprises an image of oral tissue. In some cases, the camera is located proximal to the hand piece, and the method further comprises facilitating, using the hand piece, an optical path between the oral tissue and the camera. In some cases, the optical path includes a zinc selenide lens. In some cases, the camera has a global shutter. In some embodiments, the method may additionally include scanning, using a beam scanner of the beam delivery system, to scan the laser beam as a function of a scan parameter and controlling, using the computing device, the scan parameter. In some embodiments, the method may additionally include controlling, using the computing device, the laser parameter. In some embodiments, the remote device is configured to communicate with a user of the system. In some cases, the remote device communicates by way of a network. In some cases, the network includes the Internet.

In another aspect, a system for dental treatment and verification includes a laser configured to generate a laser beam as a function of a laser parameter, a beam delivery system configured to deliver the laser beam from the laser, a hand piece configured to accept the laser beam from the beam delivery system and direct the laser beam to dental tissue, a sensor configured to detect a treatment parameter as a function of a treatment phenomenon, and a computing device configured to receive the treatment parameter from the sensor and determine aggregated treated surfaces as a function of the treatment parameter and the laser parameter. In some embodiments, the sensor comprises a position sensor and the treatment parameter represents a treated location. In some cases, the computing device is configured to generate a three-dimensional representation of the treated location. In some embodiments, the treatment parameter comprises an image of a restorative procedure. In some embodiments, the sensor comprises an optical sensor. In some cases, the optical sensor comprises a camera. In some embodiments, the computing device is further configured to generate a treatment metric as a function of one or more of the treatment parameter and the aggregated treated surfaces and communicate the treatment metric to a remote device. In some cases, generating the treatment metric comprises inputting one or more of the treatment parameter and a representation of the aggregated treated surfaces into a treatment metric machine learning model and outputting the treatment metric as a function of the treatment metric machine learning model and one or more of the treatment parameter and the representation of the aggregated treated surfaces. In some cases, generating the treatment metric further comprises training the treatment metric machine learning model by inputting a treatment metric training set into a machine learning algorithm, wherein the treatment metric training set correlates treatment metrics to one or more of the treatment parameter and the representation of the aggregated treated surfaces and training the treatment metric machine learning model as a function of the treatment metric training set and the machine learning algorithm. In some cases, the treatment metric is related to a treatment including one or more of cleaning, purifying, whitening, and alignment.

In some aspects a method of dental treatment and verification includes generating, using a laser, a laser beam as a function of a laser parameter, delivering, using a beam delivery system, the laser beam from the laser, accepting, using a hand piece, the laser beam from the beam delivery system, directing, using the hand piece, the laser beam to dental tissue, detecting, using a sensor, a treatment parameter as a function of a treatment phenomenon, receiving, using a computing device, the treatment parameter from the sensor, and determining, using the computing device, aggregated treated surfaces as a function of the treatment parameter and the laser parameter. In some embodiments, the sensor comprises a position sensor and the treatment parameter represents a treated location. In some cases, the method additionally includes generating, using the computing device, a three-dimensional representation of the treated location. In some embodiments, the treatment parameter comprises an image of a restorative procedure. In some embodiments, the sensor comprises an optical sensor. In some cases, the optical sensor comprises a camera. In some embodiments, the method additionally includes generating, using the computing device, a treatment metric as a function of one or more of the treatment parameter and the aggregated treated surfaces and communicating, using the computing device, the treatment metric to a remote device. In some cases, generating the treatment metric comprises inputting one or more of the treatment parameter and a representation of the aggregated treated surfaces into a treatment metric machine learning model and outputting the treatment metric as a function of the treatment metric machine learning model and one or more of the treatment parameter and the representation of the aggregated treated surfaces. In some cases, generating the treatment metric further comprises training the treatment metric machine learning model by inputting a treatment metric training set into a machine learning algorithm, wherein the treatment metric training set correlates treatment metrics to one or more of the treatment parameter and the representation of the aggregated treated surfaces and training the treatment metric machine learning model as a function of the treatment metric training set and the machine learning algorithm. In some cases, the treatment metric is related to a treatment including one or more of cleaning, purifying, whitening, and alignment.

In another aspect, a system for generating an image representative of oral tissue concurrently with dental laser treatment includes a laser configured to generate a laser beam as a function of a laser parameter, a beam delivery system configured to deliver the laser beam from the laser, a hand piece configured to accept the laser beam from the beam delivery system and direct the laser beam to dental tissue, a sensor configured to detect a plurality of oral images as a function of oral phenomena concurrently with delivery of the laser beam to the dental tissue, and a computing device configured to receive the plurality of oral images from the sensor and aggregate an aggregated oral image as a function of the plurality of oral images. In some cases, the aggregated oral image comprises a three-dimensional representation of oral tissue. In some cases, the computing device is further configured to associate the aggregated oral image with the laser parameter. In some embodiments, aggregating the aggregated oral image further comprises identifying at least a common feature in a first oral image and a second oral image of the plurality of oral images and transforming one or more of the first oral image and the second oral image as a function of the at least a common feature. In some cases, aggregating the aggregated oral image further comprises blending a demarcation between the first oral image and the second oral image. In some cases, blending the demarcation comprises comparing pixel values between overlapping pixels in the first oral image and the second oral image and altering the demarcation as a function of the comparison. In some cases, altering the demarcation comprises minimizing a difference in value between overlapping pixels between the first oral image and the second oral image along the demarcation. In some cases, the aggregated oral image has a resolution that is finer than one or more of 500, 250, 150, 100, 50, or 25 micrometers. In some embodiments, aggregating the aggregated oral image comprises inputting the plurality of oral images into an image aggregation machine learning model and outputting the aggregated oral image as a function of the plurality of oral images and the image aggregation machine learning model. In some cases, aggregating the aggregated oral image further comprises training the image aggregation machine learning model by inputting an image aggregation training set into a machine learning process, wherein the image aggregation training set correlates aggregated oral images to pluralities of oral images and training the image aggregation metric machine learning model as a function of the image aggregation training set and the machine learning algorithm.

In some aspects, the method of generating an image representative of oral tissue concurrently with dental laser treatment includes generating, using a laser, a laser beam as a function of a laser parameter, delivering, using a beam delivery system, the laser beam from the laser, accepting, using a hand piece, the laser beam from the beam delivery system, directing, using the hand piece, the laser beam to dental tissue, detecting, using a sensor, a plurality of oral images as a function of oral phenomena concurrently with delivery of the laser beam to the dental tissue, receiving, using a computing device, the plurality of oral images from the sensor, and aggregating, using the computing device, an aggregated oral image as a function of the plurality of oral images. In some embodiments, the aggregated oral image comprises a three-dimensional representation of oral tissue. In some cases, the method additionally includes associating, using the computing device, the aggregated oral image with the laser parameter. In some embodiments, aggregating the aggregated oral image further comprises identifying at least a common feature in a first oral image and a second oral image of the plurality of oral images and transforming one or more of the first oral image and the second oral image as a function of the at least a common feature. In some cases, aggregating the aggregated oral image further comprises blending a demarcation between the first oral image and the second oral image. In some cases, blending the demarcation comprises comparing pixel values between overlapping pixels in the first oral image and the second oral image and altering the demarcation as a function of the comparison. In some cases, altering the demarcation comprises minimizing a difference in value between overlapping pixels between the first oral image and the second oral image along the demarcation. In some embodiments, the aggregated oral image has a resolution that is finer than one or more of 500, 250, 150, 100, 50, or 25 micrometers. In some embodiments, aggregating the aggregated oral image comprises inputting the plurality of oral images into an image aggregation machine learning model and outputting the aggregated oral image as a function of the plurality of oral images and the image aggregation machine learning model. In some embodiments, wherein aggregating the aggregated oral image further comprises training the image aggregation machine learning model by inputting an image aggregation training set into a machine learning process, wherein the image aggregation training set correlates aggregated oral images to pluralities of oral images and training the image aggregation metric machine learning model as a function of the image aggregation training set and the machine learning algorithm.

In another aspect, a system for estimating future bite arrangement includes a sensor configured to detect a plurality of oral images as a function of oral phenomena and a computing device configured to receive the plurality of oral images from the sensor, aggregate an aggregated oral image as a function of the plurality of oral images, and estimate a future bite arrangement as a function of the aggregated oral image. In some embodiments, the aggregated oral image comprises a three-dimensional representation of oral tissue. In some embodiments, aggregating the aggregated oral image further comprises identifying at least a common feature in a first oral image and a second oral image of the plurality of oral images and transforming one or more of the first oral image and the second oral image as a function of the at least a common feature. In some cases, aggregating the aggregated oral image further comprises blending a demarcation between the first oral image and the second oral image. In some cases, blending the demarcation comprises comparing pixel values between overlapping pixels in the first oral image and the second oral image and altering the demarcation as a function of the comparison. In some cases, altering the demarcation comprises minimizing a difference in value between overlapping pixels between the first oral image and the second oral image along the demarcation. In some embodiments, estimating the future bite arrangement comprises inputting the aggregated oral image to a bite estimation machine learning model and estimating the future bite arrangement using the bite estimation machine learning model. In some cases, estimating the future bite arrangement further comprises inputting bite estimation training data into machine learning processes, wherein the bite estimation training data correlates oral images to subsequent bite arrangements and training the bite estimation machine learning model, using the bite estimation training data. In some cases, estimating the future bite arrangement further comprises classifying the aggregated oral image and selecting the bite estimation training data from a plurality of training data as a function of the classification of the aggregated oral image. In some cases, classifying the aggregated oral image is performed as a function of patient information.

In some aspects, a method of estimating future bite arrangement includes detecting, using a sensor, a plurality of oral images as a function of oral phenomena, receiving, using a computing device, the plurality of oral images from the sensor, aggregating, using the computing device, an aggregated oral image as a function of the plurality of oral images and estimating, using the computing device, a future bite arrangement as a function of the aggregated oral image. In some embodiments, the aggregated oral image comprises a three-dimensional representation of oral tissue. In some embodiments, aggregating the aggregated oral image further comprises identifying at least a common feature in a first oral image and a second oral image of the plurality of oral images and transforming one or more of the first oral image and the second oral image as a function of the at least a common feature. In some cases, aggregating the aggregated oral image further comprises blending a demarcation between the first oral image and the second oral image. In some cases, blending the demarcation comprises comparing pixel values between overlapping pixels in the first oral image and the second oral image and altering the demarcation as a function of the comparison. In some cases, altering the demarcation comprises minimizing a difference in value between overlapping pixels between the first oral image and the second oral image along the demarcation. estimating the future bite arrangement comprises inputting the aggregated oral image to a bite estimation machine learning model and estimating the future bite arrangement using the bite estimation machine learning model. In some cases, estimating the future bite arrangement further comprises inputting bite estimation training data into a machine learning processes, wherein the bite estimation training data correlates oral images to subsequent bite arrangements and training the bite estimation machine learning model, using the bite estimation training data. In some cases, estimating the future bite arrangement further comprises classifying the aggregated oral image and selecting the bite estimation training data from a plurality of training data as a function of the classification of the aggregated oral image. In some cases, classifying the aggregated oral image is performed as a function of patient information.

In another aspect, a system for correlating surface and subsurface oral imagery includes a sensor configured to detect a plurality of oral images as a function of oral phenomena and a computing device configured to receive the plurality of oral images from the sensor, aggregate an aggregated oral image as a function of the plurality of oral images and correlate a subsurface oral image with the aggregated oral image. In some embodiments, the aggregated oral image comprises a three-dimensional representation of oral tissue. In some embodiments, aggregating the aggregated oral image further comprises identifying at least a common feature in a first oral image and a second oral image of the plurality of oral images and transforming one or more of the first oral image and the second oral image as a function of the at least a common feature. In some cases, aggregating the aggregated oral image further comprises blending a demarcation between the first oral image and the second oral image. In some cases, blending the demarcation comprises comparing pixel values between overlapping pixels in the first oral image and the second oral image and altering the demarcation as a function of the comparison. In some cases, altering the demarcation comprises minimizing a difference in value between overlapping pixels between the first oral image and the second oral image along the demarcation. In some embodiments, wherein correlating the subsurface image with the aggregated oral image further comprises identifying at least a common feature in the aggregated oral image and the subsurface oral image of the plurality of oral images and transforming one or more of the aggregated oral image and the subsurface oral image as a function of the at least a common feature. In some embodiments, correspondence between the subsurface oral image and the aggregated oral image is within one or more of 500, 250, 150, 100, 50, or 25 micrometers. In some embodiments, wherein correlating the subsurface oral image with the aggregated oral image comprises inputting the subsurface oral image and the aggregated oral image into an image correspondence machine learning model and correlating the subsurface oral image and the aggregated oral image as a function of the subsurface oral image and the aggregated oral image and the image correspondence machine learning model. In some cases, aggregating the aggregated oral image further comprises training the image aggregation machine learning model by inputting an image correspondence training set into a machine learning process, wherein the image correspondence training set correlates aggregated oral images to subsurface oral images and training the image correspondence metric machine learning model as a function of the image correspondence training set and the machine learning algorithm.

In some aspects, a method for correlating surface and subsurface oral imagery includes detecting, using a sensor, a plurality of oral images as a function of oral phenomena, receiving, using a computing device, the plurality of oral images from the sensor, aggregating, using the computing device, an aggregated oral image as a function of the plurality of oral images, and correlating, using the computing device, a subsurface oral image with the aggregated oral image. In some embodiments, the aggregated oral image comprises a three-dimensional representation of oral tissue. In some embodiments, aggregating the aggregated oral image further comprises identifying at least a common feature in a first oral image and a second oral image of the plurality of oral images and transforming one or more of the first oral image and the second oral image as a function of the at least a common feature. In some cases, aggregating the aggregated oral image further comprises blending a demarcation between the first oral image and the second oral image. In some cases, blending the demarcation comprises comparing pixel values between overlapping pixels in the first oral image and the second oral image and altering the demarcation as a function of the comparison. In some cases, altering the demarcation comprises minimizing a difference in value between overlapping pixels between the first oral image and the second oral image along the demarcation. In some embodiments, correlating the subsurface image with the aggregated oral image further comprises identifying at least a common feature in the aggregated oral image and the subsurface oral image of the plurality of oral images and transforming one or more of the aggregated oral image and the subsurface oral image as a function of the at least a common feature. In some embodiments, correspondence between the subsurface oral image and the aggregated oral image is within one or more of 500, 250, 150, 100, 50, or 25 micrometers. In some embodiments, correlating the subsurface oral image with the aggregated oral image comprises inputting the subsurface oral image and the aggregated oral image into an image correspondence machine learning model and correlating the subsurface oral image and the aggregated oral image as a function of the subsurface oral image and the aggregated oral image and the image correspondence machine learning model. In some cases, aggregating the aggregated oral image further comprises training the image aggregation machine learning model by inputting an image correspondence training set into a machine learning process, wherein the image correspondence training set correlates aggregated oral images to subsurface oral images and training the image correspondence metric machine learning model as a function of the image correspondence training set and the machine learning algorithm.

In another aspect, a system for dental treatment and diagnosis includes a laser configured to generate a laser beam as a function of a laser parameter, a beam delivery system configured to deliver the laser beam from the laser, a hand piece configured to accept the laser beam from the beam delivery system and direct the laser beam to dental tissue, a sensor configured to detect a dental parameter as a function of a dental phenomenon, and a computing device configured to receive the dental parameter from the sensor and estimate a diagnosis as a function of the dental parameter. In some embodiments, the sensor comprises a camera and the dental parameter comprises an image of oral tissue. In some cases, the camera is located proximal to the hand piece, and the hand piece is further configured to facilitate an optical path between the oral tissue and the camera. In some embodiments, the diagnosis is a function of one or more of alignment trend, attrition trend, discoloration trend, or decay trend. In some embodiments, the beam delivery system comprises a beam scanner configured to scan the laser beam as a function of a scan parameter; and the computing device is further configured to control the scan parameter. In some cases, the computing device is further configured to control the laser parameter. In some cases, estimating the diagnosis comprises inputting the dental parameter into a diagnosis machine learning model and estimating the diagnosis using the diagnosis machine learning model. In some cases, estimating the diagnosis further comprises inputting diagnostic training data into a machine learning processes, wherein the diagnostic training data correlates dental parameters to diagnosis and training the diagnostic machine learning model, using the diagnostic training data. In some cases, estimating the diagnosis further comprises classifying the dental parameter and selecting the diagnostic training data from a plurality of training data as a function of the classification of the dental parameter. In some cases, classifying the dental parameter is performed as a function of patient information.

In some aspects, a method of dental treatment and diagnosis includes generating, using a laser, a laser beam as a function of a laser parameter, delivering, using a beam delivery system, the laser beam from the laser, accepting, using a hand piece, the laser beam from the beam delivery system, directing, using the hand piece, the laser beam to dental tissue, detecting, using a sensor, a dental parameter as a function of a dental phenomenon, receiving, using a computing device, the dental parameter from the sensor, and estimating, using the computing device, a diagnosis as a function of the dental parameter. In some embodiments, the sensor comprises a camera and the dental parameter comprises an image of oral tissue. In some cases, the camera is located proximal to the hand piece, and the method further comprises facilitating, using the hand piece, an optical path between the oral tissue and the camera. In some embodiments, the diagnosis is a function of one or more of alignment trend, attrition trend, discoloration trend, or decay trend. In some embodiments, the method additionally includes scanning, using a beam scanner of the beam delivery system, the laser beam as a function of a scan parameter, and controlling, using the computing device, the scan parameter. In some embodiments, the method additionally includes controlling, using the computing device, the laser parameter. In some embodiments, estimating the diagnosis comprises inputting the dental parameter to a diagnosis machine learning model and estimating the diagnosis using the diagnosis machine learning model. In some cases, estimating the diagnosis further comprises inputting diagnostic training data into a machine learning processes, wherein the diagnostic training data correlates dental parameters to diagnosis and training the diagnostic machine learning model, using the diagnostic training data. In some cases, estimating the diagnosis further comprises classifying the dental parameter and selecting the diagnostic training data from a plurality of training data as a function of the classification of the dental parameter. In some cases, classifying the dental parameter is performed as a function of patient information.

In another aspect, a system for estimating a trend includes a sensor configured to periodically detect a plurality of oral images representing a plurality of exposed tooth surfaces, as a function of a schedule and a computing device configured to receive the plurality of oral images from the sensor, aggregate a first aggregated oral image as a function of the plurality of oral images at a first time, aggregate a second aggregated oral image as a function of the plurality of oral images at a second time, and estimate a trend as a function of the first aggregated oral image and the second aggregated oral image. In some embodiments, a scheduling system is configured to schedule a patient for detecting a plurality of oral images representing a plurality of exposed tooth surfaces on a plurality of the patient's teeth. In some embodiments, the patient includes a pediatric patient. In some cases, the pediatric patient has deciduous teeth. In some embodiments, the trend includes an attrition trend. In some embodiments, the trend includes a future bite arrangement. In some embodiments, the trend includes an alignment trend. In some embodiments, the trend includes a decay trend. In some embodiments, the trend includes a discoloration trend. In some embodiments, estimating the trend comprises a machine learning process.

In some aspects, a method of estimating a trend includes periodically detecting, using a sensor, the plurality of oral images as a function of the schedule, receiving, using a computing device, the plurality of oral images from the sensor, aggregating, using the computing device, a first aggregated oral image as a function of the plurality of oral images at a first time, aggregating, using the computing device, a second aggregated oral image as a function of the plurality of oral images at a second time, and estimating, using the computing device, a future bite arrangement as a function of the first aggregated oral image and the second aggregated oral image. In some embodiments, scheduling, using a scheduling system, a patient for detecting a plurality of oral images representing a plurality of exposed tooth surfaces on a plurality of the patient's teeth. In some embodiments, the patient includes a pediatric patient. In some cases, the pediatric patient has deciduous teeth. In some embodiments, the trend includes an attrition trend. In some embodiments, the trend includes a future bite arrangement. In some embodiments, the trend includes an alignment trend. In some embodiments, the trend includes a decay trend. In some embodiments, the trend includes a discoloration trend. In some embodiments, estimating the trend comprises a machine learning process.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

The accompanying drawings illustrate the various embodiments of systems, methods, and other aspects of the disclosure. Any person with ordinary skills in the art will appreciate that the illustrated element boundaries (e.g., boxes, groups of boxes, or other shapes) in the figures represent one example of the boundaries. In some examples, one element may be designed as multiple elements, or multiple elements may be designed as one element. In some examples, an element shown as an internal component of one element may be implemented as an external component in another and vice versa. Further, the elements may not be drawn to scale.

Various embodiments will hereinafter be described in accordance with the appended drawings, which are provided to illustrate and not to limit the scope in any manner, wherein similar designations denote similar elements, and in which.

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

The present disclosure is best understood with reference to the detailed figures and description set forth herein. Various embodiments have been discussed with reference to the figures. However, those skilled in the art will readily appreciate that the detailed descriptions provided herein with respect to the figures are merely for explanatory purposes, as the methods and systems may extend beyond the described embodiments. For instance, the teachings presented and the needs of a particular application may yield multiple alternative and suitable approaches to implement the functionality of any detail described herein. Therefore, any approach may extend beyond certain implementation choices in the following embodiments.

References to "one embodiment," "at least one embodiment," "an embodiment," "one example," "an example," "for example," and so on indicate that the embodiment(s) or example(s) may include a particular feature, structure, characteristic, property, element, or limitation but that not every embodiment or example necessarily includes that particular feature, structure, characteristic, property, element, or limitation. Further, repeated use of the phrase "in an embodiment" does not necessarily refer to the same embodiment.

Methods of the present invention may be implemented by performing or completing manually, automatically, or a combination thereof, selected steps or tasks. The term "method" refers to manners, means, techniques, and procedures for accomplishing a given task including, but not limited to, those manners, means, techniques, and procedures either known to or readily developed from known manners, means, techniques, and procedures by practitioners of the art to which the invention belongs. The descriptions, examples, methods, and materials presented in the claims and the specification are not to be construed as limiting but rather as illustrative only. Those skilled in the art will envision many other possible variations within the scope of the technology described herein.

Figure 1:
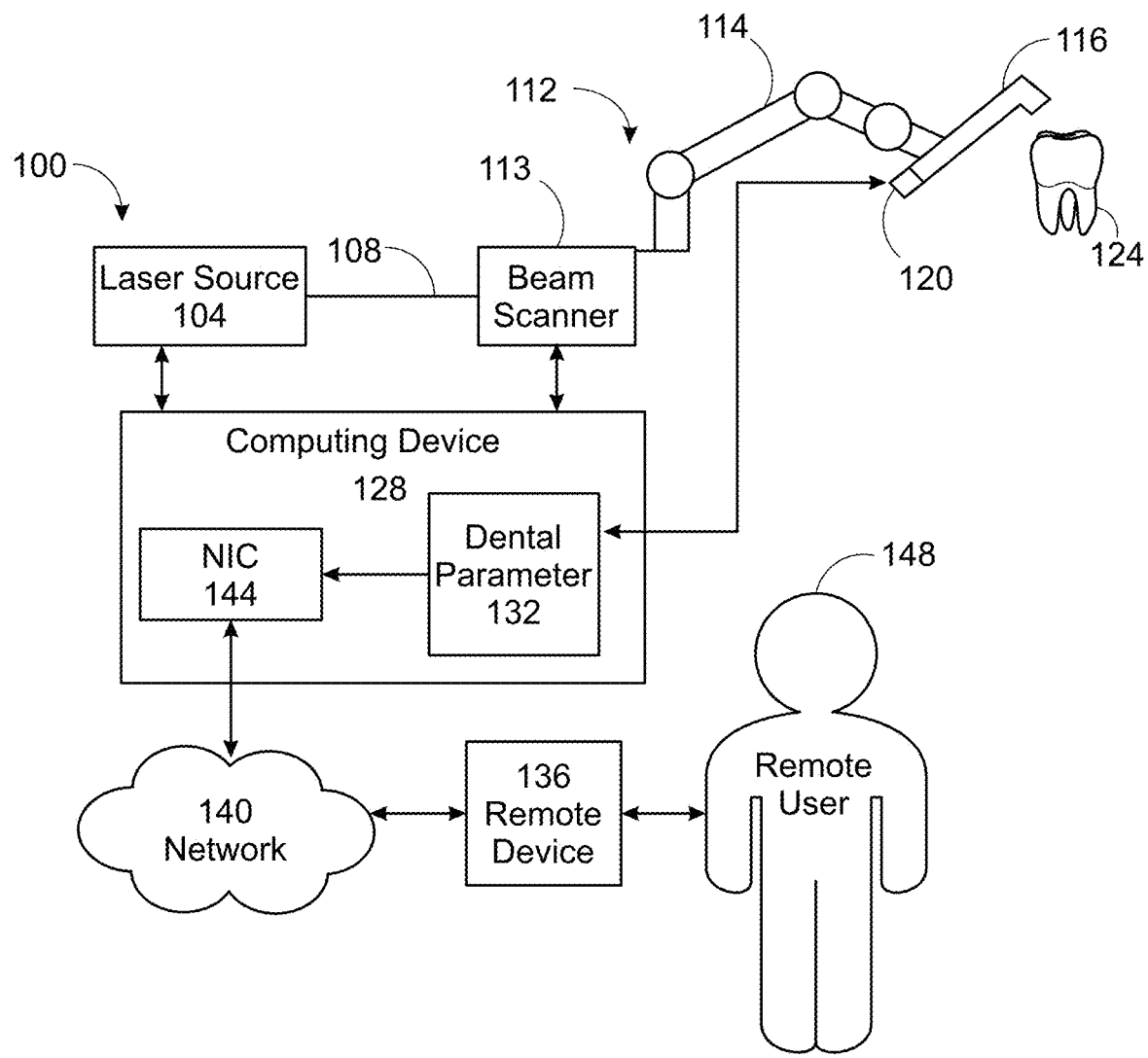
FIG. 1 illustrates a block diagram of a system for dental treatment and remote oversight, in accordance with at least one embodiment.

FIG. 1 illustrates a block diagram of a system 100 for dental treatment and remote oversight, in accordance with at least one embodiment. System 100 may include any system or constituent subsystem described in this disclosure. In some cases, the system 100 may include a laser 104, i.e. laser source. Laser may be configured to generate a laser beam 108. In some cases, laser 104 may generate a laser beam as a function of a laser parameter. In some cases, the generation of the laser beam 108 by the laser 104 is performed as part of a laser treatment, for instance a preventative treatment such as without limitation cleaning, laser acid resistance, whitening, laser bacteria removal, and the like.

With continued reference to FIG. 1, in some embodiments, the laser treatment may begin by generating the laser beam 108. The laser beam is typically generated using the laser source 104. Exemplary laser sources 104 include, without limitation, $CO_2$ lasers having a wavelength between 9 μm and 11 μm, fiber lasers, diode pumped solid state lasers (DPSS), Q-switched solid-state lasers (e.g., third harmonic Nd:YAG lasers having a wavelength of about 355 nm), Excimer lasers, and diode lasers. Commonly the laser beam 108 may have a wavelength that is well absorbed (e.g., has a wavelength having an absorption coefficient greater than 1 $cm^{-1}$, 100 $cm^{-1}$, or 1,000 $cm^{-1}$) by a dental tissue, such as a dental hard tissue like enamel or dental soft tissue, which is largely water.

With continued reference to FIG. 1, in some embodiments, system 100 may include a beam delivery system 112. The beam delivery system 112 may include any optical arrangement that transmits the laser beam 108 from an input to an output at a location different from that of the input. Exemplary beam delivery systems 112 include articulated arms, waveguides, and fiber optics. In some cases, beam delivery system 112 may be configured to deliver the laser beam 108 from the laser 104. For instance, in some cases, the beam delivery system 112 may accept the laser beam 108 at an input of the beam delivery system and transmit the laser beam 108 to an output of the laser beam delivery system.

Still referring to FIG. 1, in some embodiments the beam delivery system 112 may include a beam scanner 113. A beam scanner may include any optical component configured to actively scan the laser beam 108. Exemplary beam scanners include, without limitation, Risley prisms, spinning polygon mirrors, voice coil scanners (e.g., Part No. MR-15-30 from Optotune of Dietikon, Switzerland), galvanometers (e.g., Lightning II 2-axis scan head from Cambridge Technology of Bedford, Massachusetts, U.S.A.), and a gantry with a translating focus optic. Scanning methods related to dental laser systems are described in U.S. Pat. No. 9,408,673 by N. Monty et al., incorporated herein by reference. In some cases, beam scanner 113 may be configured to scan the laser beam 108 as a function of a scan parameter. Exemplary non-limiting scan parameters include scan patterns, scan jobs, jump speed, jump delay, mark speed, mark delay, dwell time, and the like. In some cases, scan parameters are a function of the laser parameters or vice versa. For example, in some cases a dwell time, duration of the beam scanner 113 leaves the laser beam 108 at a single point in a scan pattern, may be greater than the pulse duration of the laser beam 108, to limit beam smearing. Alternatively, or additionally, a scan pattern may be configured to have substantially no dwell time, and laser pulses are delivered while the beam scanner is in motion.

Still referring to FIG. 1, in some embodiments, beam delivery system 112 may include an articulated arm 114. An articulated arm 114 may include a number of reflective optics and a number of rotational joints, which allows a laser beam entering an arm input to be transmitted to an arm output which may be dynamically positioned relative to the arm input. An exemplary articulated arm is provided by Laser Mechanisms of Novi, Michigan, U.S.A.

With continued reference to FIG. 1, in some embodiments, a hand piece 116 may be configured to accept the laser beam 108 from the beam delivery system 112 and direct the laser beam 108 to dental tissue 124. In some embodiments, a hand piece 116 may be configured to accept the laser beam 108 from the beam delivery system 112. For example, in some cases, a hand piece input may be positioned in optical communication with the arm output of the articulated arm 114, such that the laser beam 108 leaving the articulating arm 114 enters the hand piece 116. The hand piece 116 may be configured to be used by a local user of the system; for example, the local user may manipulate the hand piece using her hand. In some cases, the hand piece 116 may be configured to direct the laser beam to a target, such as dental tissue. In some cases, the hand piece 116 is configured to be used intra-orally (i.e., within an oral cavity). Typically, the hand piece 116 includes a focus optic (not shown) that converges the laser beam to a focal region outside of the hand piece 116. The laser beam 108 may be directed toward any number of surfaces of the dental tissue. In some embodiments, the laser beam is directed into an intra-oral cavity using a beam delivery system. The laser beam is often directed within the intra-oral cavity using the hand piece. In some embodiments, the laser beam is converged, using a focus optic, as it is directed toward the dental hard tissue, such that it comes to a focal region proximal to the surface of the dental hard tissue. Exemplary focus optics include lenses (e.g., Zinc Selenide Plano-Convex lenses having an effective focal length of 200 mm) and parabolic mirrors. In some cases, any optic described in this disclosure, such as without limitation focus optic, may include a transmissive optic (e.g., window, lens, prism, or the like). Transmissive optics may include, without limitation, a zinc sulfide optic, a zinc selenide optic, a calcium fluoride optic, a magnesium fluoride optic, a sodium chloride optic, a potassium bromide optic, or a barium fluoride optic.

With continued reference to FIG. 1, system 100 may include a sensor 120. Sensor 120 may include any device configured to detect a parameter as a function of a phenomenon. In some cases, sensor 120 may be configured to detect a dental parameter 132 as a function of a dental phenomenon. A dental parameter 132 may include any representation of a dental phenomenon. A dental phenomenon may include any phenomenon relating to dental or oral tissue. In some cases, the sensor 120 may detect the dental parameter at substantially the same time as treatment, i.e., during treatment or concurrently while laser is generating laser beam.

Still referring to FIG. 1, in some embodiments, sensor 120 may include a camera 120. In some cases, the dental parameter 132 may include an image of oral tissue. As used in this disclosure, a camera may include a device that is configured to sense electromagnetic radiation, such as without limitation visible light, and generate an image representing the electromagnetic radiation. In some cases, a camera may include one or more optics. Exemplary non-limiting optics include spherical lenses, aspherical lenses, reflectors, polarizers, filters, windows, aperture stops, and the like. In some cases, at least a camera may include an image sensor. Exemplary non-limiting image sensors include digital image sensors, such as without limitation charge-coupled device (CCD) sensors and complementary metal-oxide-semiconductor (CMOS) sensors, chemical image sensors, and analog image sensors, such as without limitation film. In some cases, a camera may be sensitive within a non-visible range of electromagnetic radiation, such as without limitation infrared. As used in this disclosure, image data may include information representing at least a physical scene, space, and/or object. In some cases, image data may be generated by a camera. "Image data" may be used interchangeably through this disclosure with "image," where the image is used as a noun. An image may be optical, such as without limitation where at least an optic is used to generate an image of an object. An image may be material, such as without limitation when the film is used to capture an image. An image may be digital, such as without limitation when represented as a bitmap. Alternatively, an image may be comprised of any media capable of representing a physical scene, space, and/or object. Alternatively, where "image" is used as a verb, in this disclosure, it refers to the generation and/or formation of an image.

Still referring to FIG. 1, in some embodiments, sensor 120 may include a machine vision system that includes at least a camera 120. A machine vision system may use images from at least a camera 120, to determine a scene, space, and/or object. For example, in some cases, a machine vision system may be used for world modeling or registration of objects within a space. In some cases, registration may include image processing, such as without limitation object recognition, feature detection, edge/corner detection, and the like. A non-limiting example of feature detection may include scale-invariant feature transform (SIFT), Canny edge detection, Shi Tomasi corner detection, and the like. In some cases, registration may include one or more transformations to orient a camera frame (or an image or video stream) relative to a three-dimensional coordinate system; exemplary transformations include without limitation homography transforms and affine transforms. In an embodiment, registration of the first frame to a coordinate system may be verified and/or corrected using object identification and/or computer vision, as described above. For instance, and without limitation, an initial registration to two dimensions, represented for instance as registration to the x and y coordinates, may be performed using a two-dimensional projection of points in three dimensions onto a first frame, however. A third dimension of registration, representing depth and/or a z-axis, may be detected by comparison of two frames; for instance, where the first frame includes a pair of frames captured using a pair of cameras (e.g., the stereoscopic camera also referred to in this disclosure as stereo-camera), image recognition and/or edge detection software may be used to detect a pair of stereoscopic views of images of an object; two stereoscopic views may be compared to derive z-axis values of points on object permitting, for instance, derivation of further z-axis points within and/or around the object using interpolation. This may be repeated with multiple objects in the field of view, including without limitation environmental features of interest identified by the object classifier and/or indicated by an operator. In an embodiment, x and y axes may be chosen to span a plane common to two cameras used for stereoscopic image capturing and/or a xy plane of a first frame; a result, x and y translational components and q may be pre-populated in translational and rotational matrices, for the affine transformation of coordinates of the object, also as described above. Initial x and y coordinates and/or guesses at transformational matrices may alternatively or additionally be performed between the first frame and second frame, as described above. For each point of a plurality of points on the object and/or edge and/or edges of the object as described above, x and y coordinates of a first stereoscopic frame may be populated, with an initial estimate of z coordinates based, for instance, on assumptions about the object, such as an assumption that ground is substantially parallel to a xy plane as selected above. Z coordinates, and/or x, y, and z coordinates, registered using the image capturing and/or object identification processes as described above may then be compared to coordinates predicted using initial guess at transformation matrices; an error function may be computed using by comparing the two sets of points, and new x, y, and/or z coordinates, may be iteratively estimated and compared until the error function drops below a threshold level. In some cases, a machine vision system may use a classifier, such as any classifier described throughout this disclosure.

Still referring to FIG. 1, in some embodiments, sensor 120 may include a machine vision camera 120. An exemplary machine vision camera is an OpenMV Cam H7 from OpenMV, LLC of Atlanta, Georgia, U.S.A. OpenMV Cam comprises a small, low-power, microcontroller which allows the execution of machine vision applications. OpenMV Cam comprises an ARM Cortex M7 processor and a 640×480 image sensor operating at a frame rate of up to 150 fps. OpenMV Cam may be programmed with Python using a Remote Python/Procedure Call (RPC) library. OpenMV CAM may be used to operate image classification and segmentation models, such as without limitation by way of TensorFlow Lite; detection motion, for example by way of frame differencing algorithms; marker detection, for example, blob detection; object detection, for example, face detection; eye tracking; person detection, for example by way of a trained machine learning model; camera motion detection, for example by way of optical flow detection; code (barcode) detection and decoding; image capture; and video recording.

Still referring to FIG. 1, sensor 120 may include a stereo-camera 120. As used in this disclosure, a stereo camera may include a camera that senses two or more images from two or more vantages. As used in this disclosure, a "vantage" is a location of a camera relative to a scene, space, and/or object that the camera is configured to sense. In some cases, a stereo camera may determine the depth of an object in a scene as a function of parallax. As used in this disclosure, "parallax" is a difference in the perceived location of a corresponding object in two or more images. An exemplary stereo camera is TaraXL from e-con Systems, Inc of San Jose, California. TaraXL is a USB 3.0 stereo camera that is optimized for NVIDIA® Jetson AGX Xavier™/Jetson™ TX2 and NVIDIA GPU Cards. TaraXL's accelerated Software Development Kit (TaraXL SDK) is capable of doing high-quality 3D depth mapping of WVGA at a rate of up to 60 frames per second. TaraXL is based on an MT9V024 stereo sensor from ON Semiconductor. Additionally, TaraXL includes a global shutter, houses 6 inertial measurement units (IMUs), and allows the mounting of optics by way of an S-mount lens holder. TaraXL may operate at depth ranges of about 50 cm to about 300 cm.

Still referring to FIG. 1, in some embodiments, sensor 120 may include a range-imaging camera 120. An exemplary range-imaging camera may be Intel® RealSense™ D430 Module, from Intel® of Mountainview, California, U.S.A. D430 Module comprises active infrared (IR) illumination and a stereoscopic camera, having global shutters and a frame rate of up to 90 fps. D430 Module provides a field of view (FOV) of 85.2° (horizontal) by 58° (vertical) and an image resolution of 1280×720. The range-sensing camera may be operated independently by dedicated hardware or, in some cases, a range-sensing camera may be operated by a computing device. In some cases, the range-sensing camera may include software and firmware resources (for execution on hardware, such as without limitation dedicated hardware or a computing device). D430 Module may be operating using software resources including Intel® RealSense™ SDK 2.0, which includes open-source cross-platform libraries.

With continued reference to FIG. 1, in an embodiment, a system 100 for generating an image representative of oral tissue concurrently with dental laser treatment includes a laser configured to generate a laser beam as a function of a laser parameter, a beam delivery system configured to deliver the laser beam from the laser, a hand piece configured to accept the laser beam from the beam delivery system and direct the laser beam to dental tissue, a sensor configured to detect a plurality of oral images as a function of oral phenomena concurrently with delivery of the laser beam to the dental tissue, and a computing device configured to receive the plurality of oral images from the sensor and aggregate an aggregated oral image as a function of the plurality of oral images. In some cases, the aggregated oral image comprises a three-dimensional representation of oral tissue. In some cases, the computing device is further configured to associate the aggregated oral image with the laser parameter. In some embodiments, aggregating the aggregated oral image further comprises identifying at least a common feature in a first oral image and a second oral image of the plurality of oral images and transforming one or more of the first oral image and the second oral image as a function of the at least a common feature. In some cases, aggregating the aggregated oral image further comprises blending a demarcation between the first oral image and the second oral image. In some cases, blending the demarcation comprises comparing pixel values between overlapping pixels in the first oral image and the second oral image and altering the demarcation as a function of the comparison. In some cases, altering the demarcation comprises minimizing a difference in value between overlapping pixels between the first oral image and the second oral image along the demarcation. In some cases, the aggregated oral image has a resolution that is finer than one or more of 500, 250, 150, 100, 50, or 25 micrometers. In some embodiments, aggregating the aggregated oral image comprises inputting the plurality of oral images into an image aggregation machine learning model and outputting the aggregated oral image as a function of the plurality of oral images and the image aggregation machine learning model. In some cases, aggregating the aggregated oral image further comprises training the image aggregation machine learning model by inputting an image aggregation training set into a machine learning process, wherein the image aggregation training set correlates aggregated oral images to pluralities of oral images and training the image aggregation metric machine learning model as a function of the image aggregation training set and the machine learning algorithm.

With continued reference to FIG. 1, according to an embodiment herein, the method of generating an image representative of oral tissue concurrently with dental laser treatment includes generating, using a laser, a laser beam as a function of a laser parameter, delivering, using a beam delivery system, the laser beam from the laser, accepting, using a hand piece, the laser beam from the beam delivery system, directing, using the hand piece, the laser beam to dental tissue, detecting, using a sensor, a plurality of oral images as a function of oral phenomena concurrently with delivery of the laser beam to the dental tissue, receiving, using a computing device, the plurality of oral images from the sensor, and aggregating, using the computing device, an aggregated oral image as a function of the plurality of oral images. In some embodiments, the aggregated oral image comprises a three-dimensional representation of oral tissue. In some cases, the method additionally includes associating, using the computing device, the aggregated oral image with the laser parameter. In some cases, aggregating the aggregated oral image further comprises identifying at least a common feature in a first oral image and a second oral image of the plurality of oral images and transforming one or more of the first oral image and the second oral image as a function of the at least a common feature. In some cases, aggregating the aggregated oral image further comprises blending a demarcation between the first oral image and the second oral image. In some cases, blending the demarcation comprises comparing pixel values between overlapping pixels in the first oral image and the second oral image and altering the demarcation as a function of the comparison. In some cases, altering the demarcation comprises minimizing a difference in value between overlapping pixels between the first oral image and the second oral image along the demarcation. In some embodiments, the aggregated oral image has a resolution that is finer than one or more of 500, 250, 150, 100, 50, or 25 micrometers. In some embodiments, aggregating the aggregated oral image comprises inputting the plurality of oral images into an image aggregation machine learning model and outputting the aggregated oral image as a function of the plurality of oral images and the image aggregation machine learning model. In some embodiments, wherein aggregating the aggregated oral image further comprises training the image aggregation machine learning model by inputting an image aggregation training set into a machine learning process, wherein the image aggregation training set correlates aggregated oral images to pluralities of oral images and training the image aggregation metric machine learning model as a function of the image aggregation training set and the machine learning algorithm.

With continued reference to FIG. 1, in another embodiment, a system 100 for correlating surface and subsurface oral imagery includes a sensor configured to detect a plurality of oral images as a function of oral phenomena and a computing device configured to receive the plurality of oral images from the sensor, aggregate an aggregated oral image as a function of the plurality of oral images and correlate a subsurface oral image with the aggregated oral image. In some embodiments, the aggregated oral image comprises a three-dimensional representation of oral tissue. In some embodiments, aggregating the aggregated oral image further comprises identifying at least a common feature in a first oral image and a second oral image of the plurality of oral images and transforming one or more of the first oral image and the second oral image as a function of the at least a common feature. In some cases, aggregating the aggregated oral image further comprises blending a demarcation between the first oral image and the second oral image. In some cases, blending the demarcation comprises comparing pixel values between overlapping pixels in the first oral image and the second oral image and altering the demarcation as a function of the comparison. In some cases, altering the demarcation comprises minimizing a difference in value between overlapping pixels between the first oral image and the second oral image along the demarcation. In some embodiments, wherein correlating the subsurface image with the aggregated oral image further comprises identifying at least a common feature in the aggregated oral image and the subsurface oral image of the plurality of oral images and transforming one or more of the aggregated oral image and the subsurface oral image as a function of the at least a common feature. In some embodiments, correspondence between the subsurface oral image and the aggregated oral image is within one or more of 500, 250, 150, 100, 50, or 25 micrometers. In some embodiments, wherein correlating the subsurface oral image with the aggregated oral image comprises inputting the subsurface oral image and the aggregated oral image into an image correspondence machine learning model and correlating the subsurface oral image and the aggregated oral image as a function of the subsurface oral image and the aggregated oral image and the image correspondence machine learning model. In some cases, aggregating the aggregated oral image further comprises training the image aggregation machine learning model by inputting an image correspondence training set into a machine learning process, wherein the image correspondence training set correlates aggregated oral images to subsurface oral images and training the image correspondence metric machine learning model as a function of the image correspondence training set and the machine learning algorithm.

With continued reference to FIG. 1, according to an embodiment herein, a method for correlating surface and subsurface oral imagery includes detecting, using a sensor, a plurality of oral images as a function of oral phenomena, receiving, using a computing device, the plurality of oral images from the sensor, aggregating, using the computing device, an aggregated oral image as a function of the plurality of oral images, and correlating, using the computing device, a subsurface oral image with the aggregated oral image. In some embodiments, the aggregated oral image comprises a three-dimensional representation of oral tissue. In some embodiments, aggregating the aggregated oral image further comprises identifying at least a common feature in a first oral image and a second oral image of the plurality of oral images and transforming one or more of the first oral image and the second oral image as a function of the at least a common feature. In some cases, aggregating the aggregated oral image further comprises blending a demarcation between the first oral image and the second oral image. In some cases, blending the demarcation comprises comparing pixel values between overlapping pixels in the first oral image and the second oral image and altering the demarcation as a function of the comparison. In some cases, altering the demarcation comprises minimizing a difference in value between overlapping pixels between the first oral image and the second oral image along the demarcation. In some embodiments, correlating the subsurface image with the aggregated oral image further comprises identifying at least a common feature in the aggregated oral image and the subsurface oral image of the plurality of oral images and transforming one or more of the aggregated oral image and the subsurface oral image as a function of the at least a common feature. In some embodiments, correspondence between the subsurface oral image and the aggregated oral image is within one or more of 500, 250, 150, 100, 50, or 25 micrometers. In some embodiments, correlating the subsurface oral image with the aggregated oral image comprises inputting the subsurface oral image and the aggregated oral image into an image correspondence machine learning model and correlating the subsurface oral image and the aggregated oral image as a function of the subsurface oral image and the aggregated oral image and the image correspondence machine learning model. In some cases, aggregating the aggregated oral image further comprises training the image aggregation machine learning model by inputting an image correspondence training set into a machine learning process, wherein the image correspondence training set correlates aggregated oral images to subsurface oral images and training the image correspondence metric machine learning model as a function of the image correspondence training set and the machine learning algorithm.

With continued reference to FIG. 1, system 100 may include a computing device 128. The computing device 128 may be configured to receive dental parameter 132 from the sensor 120 and/or communicate the dental parameter 132 to a remote device 136. A remote device 136 may include a computing device located remotely from the system 100. Computing devices are described in greater detail below. In some cases, the computing device may be said to be in communication with the sensor 120 and/or the remote device 136. Communication, for instance between a computing device 128 and another device such as a sensor 120 and/or remote device, may be performed by way of one or more networks 140 and/or protocols. Exemplary communication networks and protocols are described in greater detail below. In some cases, communication may be performed using one or more signals; for instance, a signal may represent the dental parameter 132.

Still referring to FIG. 1, As used in this disclosure, a "signal" is any intelligible representation of data, for example from one device to another. A signal may include an optical signal, a hydraulic signal, a pneumatic signal, a mechanical, signal, an electric signal, a digital signal, an analog signal, and the like. In some cases, a signal may be used to communicate with a computing device, for example by way of one or more ports. In some cases, a signal may be transmitted and/or received by a computing device for example by way of an input/output port. An analog signal may be digitized, for example by way of an analog-to-digital converter. In some cases, an analog signal may be processed, for example by way of any analog signal processing steps described in this disclosure, before digitization. In some cases, a digital signal may be used to communicate between two or more devices, including without limitation computing devices. In some cases, a digital signal may be communicated by way of one or more communication protocols, including without limitation internet protocol (IP), controller area network (CAN) protocols, serial communication protocols (e.g., universal asynchronous receiver-transmitter [UART]), parallel communication protocols (e.g., IEEE 128 [printer port]), and the like.

Still referring to FIG. 1, in some cases, system 100 or one or more subsystems such as a computing device 128, sensor, 120, and/or remote device 140 may perform one or more signal processing steps on a signal. For instance, a system may analyze, modify, and/or synthesize a signal representative of data to improve the signal, for instance, by improving transmission, storage efficiency, or signal-to-noise ratio. Exemplary methods of signal processing may include analog, continuous time, discrete, digital, nonlinear, and statistical. Analog signal processing may be performed on non-digitized or analog signals. Exemplary analog processes may include passive filters, active filters, additive mixers, integrators, delay lines, compandors, multipliers, voltage-controlled filters, voltage-controlled oscillators, and phase-locked loops. Continuous-time signal processing may be used, in some cases, to process signals which vary continuously within a domain, for instance, time. Exemplary non-limiting continuous time processes may include time domain processing, frequency domain processing (Fourier transform), and complex frequency domain processing. Discrete-time signal processing may be used when a signal is sampled non-continuously or at discrete time intervals (i.e., quantized in time). Analog discrete-time signal processing may process a signal using the following exemplary circuits sample and hold circuits, analog time-division multiplexers, analog delay lines, and analog feedback shift registers. Digital signal processing may be used to process digitized discrete-time sampled signals. Commonly, digital signal processing may be performed by a computing device or other specialized digital circuits, such as without limitation an application-specific integrated circuit (ASIC), a field-programmable gate array (FPGA), or a specialized digital signal processor (DSP). Digital signal processing may be used to perform any combination of typical arithmetical operations, including fixed-point and floating-point, real-valued and complex-valued, multiplication, and addition. Digital signal processing may additionally operate circular buffers and lookup tables. Further non-limiting examples of algorithms that may be performed according to digital signal processing techniques include fast Fourier transform (FFT), finite impulse response (FIR) filter, infinite impulse response (IIR) filter, and adaptive filters such as the Wiener and Kalman filters. Statistical signal processing may be used to process a signal as a random function (i.e., a stochastic process), utilizing statistical properties. For instance, in some embodiments, a signal may be modeled with a probability distribution indicating noise, which then may be used to reduce noise in a processed signal.

With continued reference to FIG. 1, remote device 136 may be configured to interface with a remote user. In some cases, a remote user may include a licensed dentist or medical professional. In some cases, the remote device may include any computing device described herein. The remote user may interface with remote device 136 and communicate with a user of system 100. In some cases, the system 100 may communicate the dental parameter at substantially the same time as treatment, i.e., during treatment or concurrently while laser is generating laser beam.

With continued reference to FIG. 1, in another embodiment, a system 100 for dental treatment and remote oversight includes a laser configured to generate a laser beam as a function of a laser parameter, a beam delivery system configured to deliver the laser beam from the laser, a hand piece configured to accept the laser beam from the beam delivery system and direct the laser beam to dental tissue, a sensor configured to detect a dental parameter as a function of a dental phenomenon, a computing device configured to receive the dental parameter from the sensor and communicate the dental parameter to a remote device configured to interface with a remote user. In some embodiments, the sensor comprises a camera and the dental parameter comprises an image of oral tissue. In some cases, the camera is located proximal to the hand piece, and the hand piece is further configured to facilitate an optical path between the oral tissue and the camera. In some cases, the optical path comprises one or more of a zinc sulfide lens, a calcium fluoride lens, a magnesium fluoride optic, a sodium chloride optic, a potassium bromide optic, or a barium fluoride optic. In some cases, the camera comprises a global shutter. In some embodiments, the beam delivery system comprises a beam scanner configured to scan the laser beam as a function of a scan parameter; wherein, the computing device is further configured to control the scan parameter. In some embodiments, the computing device is further configured to control the laser parameter. In some embodiments, the remote device is configured to communicate with a user of the system. In some cases, the remote device communicates by way of a network. In some cases, the network includes the Internet.

With continued reference to FIG. 1, according to an embodiment herein, a method of dental treatment and remote oversight includes generating, using a laser configured, a laser beam as a function of a laser parameter, delivering, using a beam delivery system, the laser beam from the laser, accepting, using a hand piece, the laser beam from the beam delivery system, directing, using the hand piece, the laser beam to dental tissue, detecting, using a sensor, a dental parameter as a function of a dental phenomenon, receiving, using a computing device, the dental parameter from the sensor, and communicating, using the computing device, the dental parameter to a remote device configured to interface with a remote user. In some embodiments, the sensor comprises a camera and the dental parameter comprises an image of oral tissue. In some cases, the camera is located proximal to the hand piece, and the method further comprises facilitating, using the hand piece, an optical path between the oral tissue and the camera. In some cases, the optical path includes a zinc selenide lens. In some cases, the camera has a global shutter. In some embodiments, the method may additionally include scanning, using a beam scanner of the beam delivery system, to scan the laser beam as a function of a scan parameter and controlling, using the computing device, the scan parameter. In some embodiments, the method may additionally include controlling, using the computing device, the laser parameter. In some embodiments, the remote device is configured to communicate with a user of the system. In some cases, the remote device communicates by way of a network. In some cases, the network includes the Internet.

Still referring to FIG. 1, in some embodiments, the computing device 128 may be configured to control the laser parameter and/or the scan parameter. In some embodiments, the laser parameter of the laser beam is controlled to affect treatment. Typically, the parameter of the laser beam is controlled to heat a portion of the surface of the dental hard tissue to a temperature within a range, for example between about 100° C. and about 1300° C. Exemplary laser parameters include pulse energy, pulse duration, peak power, average power, repetition rate, wavelength, duty cycle, laser focal region size, laser focal region location, and laser focal region scan speed. During laser treatment, a laser beam is generated and directed toward a surface of dental hard tissue. Typically, the laser beam is pulsed at a prescribed repetition rate and has a certain pulse duration. Alternatively, pulses can be delivered on demand, and the pulse duration can vary (for example, to control the heating of the surface of the dental hard tissue). As a result of the irradiation of the surface, the temperature of the surface rises typically to within a range (e.g., between 100° C. and 1300° C.) momentarily (e.g., during a duration of the laser pulse) and cools back to a normal temperature range (e.g., within a range of 20° C. and 60° C.). As a result of the momentary temperature rise biological materials previously near or adhered to the surface of the dental hard tissue (e.g., pellicle, bio-film, calculus, and tartar) are at least partially removed or denatured. In some embodiments, this removal of biological materials substantially cleans the teeth and the laser treatment replaces other tooth-cleaning procedures typically performed during a dental check-up (e.g., scaling and polishing). Additionally, as described above, heating the surface of the dental hard tissue removes impurities (e.g., carbonate) from the dental hard tissue and makes the dental hard tissue less susceptible to acid dissolution (e.g., demineralization). An exemplary laser energy dosage delivered during a single treatment does not exceed an average power of about 2 W, a treatment time of about 600 seconds, and therefore does not deliver more than about 1200 J of laser energy to the oral cavity. In some embodiments, the laser treatment is performed after other treatments during a dental visit. For example, in some cases, the dental laser treatment is performed only after one or more of the removal of plaque and tartar (with one or more manual instruments), professional flossing, and power polishing (i.e., dental prophylaxis). This order of steps in some cases is considered advantageous, as the laser treatment purifies only an outer portion (e.g., 2 μm thick) of the dental enamel and some dental cleaning treatments can remove a portion of dental enamel (e.g., power polishing), potentially removing the enamel which has just been purified.

With continued reference to FIG. 1, in some embodiment, effective treatment of an enamel surface needs to have its temperature raised momentarily to within an elevated range (e.g., about 400° C. to about 1500° C.). As described throughout, elevating the temperature of enamel changes the chemical composition of hydroxyapatite within the enamel. Dental enamel comprises 96% (wt %) hydroxyapatite, 3% water, and 1% organic molecules (lipids and proteins). Specifically, dental enamel comprises 96% calcium-deficient carbonated hydroxyapatite (CAP), with a chemical formula approximated by $Ca_{10-x}Na_x(PO_4)_{6-y}(CO_3)_z(OH)_{2-u}Fu$. The ideal chemical formula for hydroxyapatite (HAP), by comparison, is approximated as $Ca_{10}(PO_4)_6(OH)_2$. The calcium deficiency of dental enamel is shown by the x in $Ca_{10-x}$. Some of the calcium is replaced by metals, such as sodium, magnesium, and potassium. These metals together total about 1% of enamel. Some of the OH molecules in dental enamel are replaced by F. But the major difference between CAP and HAP comes with the presence of carbonate. Carbonate comprises between about 2 and about 5% (wt %) of dental enamel. The presence of carbonate within the hydroxyapatite structure disturbs the crystal lattice of the CAP, changing the size and shape of the unit crystal form and resulting in different mechanical and chemical properties between CAP and HAP. Increased carbonate content in enamel correlates with increases in susceptibility to acid and inversely correlates with crystallinity, hardness, and modulus (i.e., stiffness). Said another way the purer HAP erodes (through acid dissolution), wears (through mechanical means), and ages more slowly, compared to CAP.

As has been described in the literature, including the Co-owned Int. Patent Appl. No. PCT/US21/15567, entitled "Preventative Dental Hard Tissue Laser Treatment Systems, Methods, and Computer-Readable Media", by C. Dresser et al., incorporated herein by reference, carbonate can be removed from dental enamel by laser irradiation at prescribed parameters. Specifically, by using a laser source that is well absorbed (e.g., the absorbance of at least 500 cm$^{-1}$) in dental enamel, and heating the surface of the tooth momentarily (e.g., at pulse durations that are no greater than 100× a thermal relaxation time) to a temperature of at least about 400° C., carbonate is driven (e.g., sublimated) from the enamel.

With continued reference to FIG. 1, Computing device 128 may include any computing device as described in this disclosure, including without limitation a microcontroller, microprocessor, digital signal processor (DSP), and/or system on a chip (SoC) as described in this disclosure. The computing device may include, be included in, and/or communicate with a mobile device such as a mobile telephone or smartphone. Computing device 128 may include a single computing device operating independently, or may include two or more computing devices operating in concert, in parallel, sequentially, or the like; two or more computing devices may be included together in a single computing device or two or more computing devices. Computing device 128 may interface or communicate with one or more additional devices as described below in further detail via a network interface device 144. The network interface device 144 may be utilized for connecting computing device 128 to one or more of a variety of networks 140, and one or more devices. Examples of a network interface device 144 include, but are not limited to, a network interface card 144 (e.g., a mobile network interface card, a LAN card), a modem, and any combination thereof. Examples of a network 140 include, but are not limited to, a wide area network (e.g., the Internet, an enterprise network), a local area network (e.g., a network associated with an office, a building, a campus, or other relatively small geographic space), a telephone network, a data network associated with a telephone/voice provider (e.g., a mobile communications provider data and/or voice network), a direct connection between two computing devices, and any combinations thereof. A network may employ a wired and/or wireless mode of communication. In general, any network topology may be used. Information (e.g., data, software, etc.) may be communicated to and/or from a computer and/or a computing device. Computing device 128 may include but is not limited to, for example, a computing device or cluster of computing devices in a first location and a second computing device or cluster of computing devices in a second location. Computing device 128 may include one or more computing devices dedicated to data storage, security, distribution of traffic for load balancing, and the like. Computing device 128 may distribute one or more computing tasks as described below across a plurality of computing devices of computing device, which may operate in parallel, in series, redundantly, or in any other manner used for the distribution of tasks or memory between computing devices. Computing device 128 may be implemented using a "shared nothing" architecture in which data is cached at the worker, in an embodiment, this may enable the scalability of system 100 and/or the computing device.

With continued reference to FIG. 1, computing device 128 may be designed and/or configured to perform any method, method step, or sequence of method steps in any embodiment described in this disclosure, in any order and with any degree of repetition. For instance, computing device 128 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 128 may perform any step or sequence of steps as described in this disclosure in parallels, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, in another embodiment, a system 100 for dental treatment and diagnosis includes a laser configured to generate a laser beam as a function of a laser parameter, a beam delivery system configured to deliver the laser beam from the laser, a hand piece configured to accept the laser beam from the beam delivery system and direct the laser beam to dental tissue, a sensor configured to detect a dental parameter as a function of a dental phenomenon, and a computing device configured to receive the dental parameter from the sensor and estimate a diagnosis as a function of the dental parameter. In some embodiments, the sensor comprises a camera and the dental parameter comprises an image of oral tissue. In some cases, the camera is located proximal to the hand piece, and the hand piece is further configured to facilitate an optical path between the oral tissue and the camera. In some embodiments, the diagnosis is a function of one or more of alignment trend, attrition trend, discoloration trend, or decay trend. In some embodiments, the beam delivery system comprises a beam scanner configured to scan the laser beam as a function of a scan parameter; and the computing device is further configured to control the scan parameter. In some cases, the computing device is further configured to control the laser parameter. In some cases, estimating the diagnosis comprises inputting the dental parameter into a diagnosis machine learning model and estimating the diagnosis using the diagnosis machine learning model. In some cases, estimating the diagnosis further comprises inputting diagnostic training data into a machine learning processes, wherein the diagnostic training data correlates dental parameters to diagnosis and training the diagnostic machine learning model, using the diagnostic training data. In some cases, estimating the diagnosis further comprises classifying the dental parameter and selecting the diagnostic training data from a plurality of training data as a function of the classification of the dental parameter. In some cases, classifying the dental parameter is performed as a function of patient information.

With continued reference to FIG. 1, according to an embodiment herein, a method of dental treatment and diagnosis includes generating, using a laser, a laser beam as a function of a laser parameter, delivering, using a beam delivery system, the laser beam from the laser, accepting, using a hand piece, the laser beam from the beam delivery system, directing, using the hand piece, the laser beam to dental tissue, detecting, using a sensor, a dental parameter as a function of a dental phenomenon, receiving, using a computing device, the dental parameter from the sensor, and estimating, using the computing device, a diagnosis as a function of the dental parameter. In some embodiments, the sensor comprises a camera and the dental parameter comprises an image of oral tissue. In some cases, the camera is located proximal to the hand piece, and the method further comprises facilitating, using the hand piece, an optical path between the oral tissue and the camera. In some embodiments, the diagnosis is a function of one or more of alignment trend, attrition trend, discoloration trend, or decay trend. In some embodiments, the method additionally includes scanning, using a beam scanner of the beam delivery system, the laser beam as a function of a scan parameter, and controlling, using the computing device, the scan parameter. In some embodiments, the method additionally includes controlling, using the computing device, the laser parameter. In some embodiments, estimating the diagnosis comprises inputting the dental parameter to a diagnosis machine learning model and estimating the diagnosis using the diagnosis machine learning model. In some cases, estimating the diagnosis further comprises inputting diagnostic training data into a machine learning processes, wherein the diagnostic training data correlates dental parameters to diagnosis and training the diagnostic machine learning model, using the diagnostic training data. In some cases, estimating the diagnosis further comprises classifying the dental parameter and selecting the diagnostic training data from a plurality of training data as a function of the classification of the dental parameter. In some cases, classifying the dental parameter is performed as a function of patient information.

Still referring to FIG. 1, system 100, or like systems described in this disclosure, may be used to perform a number of functions, including but not limited to: (1) identifying and/or tracking attrition (e.g., acid erosion) over time; (2) identifying and/or tracking wear, such as night grinding (i.e., bruxism), for instance by monitoring multiple teeth locations and identifying matching wear patterns; (3) identifying and/or tracking incipient dental decay; (4) identifying and/or tracking dental cracks; (5) identifying and/or tracking gum disease, for example through redness increase, gum geometrical changes, and swelling; (6) identifying and/or tracking gum recession and abfractions; (7) automatic charting, for example of existing restorations; (8) automatic charting of pocket depth; and (9) identifying the need and extent of cosmetic changes and minimizing the use of formulations in delivering cosmetic whitening. Alternatively or additionally, in some embodiments, greatest value of the application of the technology described in this disclosure comes from an ability to perform longitudinal studies to monitor oral health over time. In some cases, 5-7 minutes needed for treatment (e.g., cleaning) provides ample time to capture total tooth coverage, using sensing technologies described in this disclosure, and feed processors (running machine-learning software) which yield clinical insights.

In some embodiments, systems and methods described in this disclosure may be used for (1) identifying and/or tracking attrition (e.g., erosion). The systems and methods described herein apply the described technology to identifying and/or tracking attrition (e.g., erosion) and are an improvement to existing methods. Currently, attrition, i.e., loss of hard dental tissue (e.g., enamel, dentin, cementum) is not measured in dental practice. This lack of measurement, presently, results in a lost opportunity for early intervention. Loss of enamel, dentin, and/or cementum could indicate any number of pathologies which may also be better diagnosed with tracking and/or identification of attrition, including, but not limited to tooth grinding, malocclusion (problems with bite), bulimia, nocturnal acid reflux and sleep apnea.

In some embodiments, systems and methods described in this disclosure may be used for (2) identifying and/or tracking wear, such as night grinding (i.e., bruxism). The systems and methods described herein apply the described technology to identifying and/or tracking wear, such as night grinding (i.e., bruxism), and are an improvement to existing methods. Currently, wear, which is indicated by loss of hard dental tissue (e.g., enamel, dentin, cementum), is not measured in dental practice. This lack of measurement, presently, results in a lost opportunity for early intervention. Loss of enamel, dentin, and/or cementum could indicate any number of pathologies which may also be better diagnosed with tracking and/or identification of attrition, including, but not limited to tooth grinding, malocclusion (problems with bite), bulimia, nocturnal acid reflux and sleep apnea.

In some embodiments, systems and methods described in this disclosure may be used for (3) identifying and/or tracking incipient dental decay, such as caries. The systems and methods described herein apply the described technology to identifying and/or tracking incipient dental decay and are an improvement to existing methods. Currently, decay is when a cavity is found. This lack of measurement, tracking, and/or identification of early decay, presently, results in a lost opportunity for early intervention. In some cases, identifying and/or tracking incipient dental decay may allow for early less invasive treatment, including, for example, shifting a need for a filling to a preventive restorative restoration (PRR) at the discretion of the dentist.

In some embodiments, systems and methods described in this disclosure may be used for (4) identifying and/or tracking cracks in dental hard tissue. The systems and methods described herein apply the described technology to identifying and/or tracking cracks in dental hard tissue and are an improvement to existing methods. Currently, cracks in dental hard dental tissue (e.g., enamel, dentin, cementum) are not measured in dental practice. This lack of measurement, presently, results in a lost opportunity for early intervention.

Presently, cracks are difficult to detect as they are often invisible, to the dental practitioner, while causing significant symptoms present to a patient as originating within groups of teeth. In some cases, uncertainty abounding the crack can lead to erroneous extractions or root canal treatments of teeth that are adjacent to the cracked tooth, according to existing methods. Currently, testing for a cracked tooth relies on testing nerve function and assessing for pain on bite without visual or radiographic confirmation of the presence of a crack. The present method is a diagnosis of exclusion which means that a crack is suspected based on a presence of symptoms in the absence of any other evidence for these symptoms. Comparatively, systems and methods described in this disclosure may permit the detection, identification, and/or tracking of cracks through measurement (e.g., visual imagery) taken concurrently with a prophylactic procedure, such as cleaning.

In some embodiments, systems and methods described in this disclosure may be used for (5) identifying and/or tracking gum disease, for example through quantifying a color of dental hard tissue over time. The systems and methods described herein apply the described technology to identifying and/or gum disease and are an improvement to existing methods. Currently, gum disease inflammation is not measured in dental practice. This lack of measurement, presently, results in a lost opportunity for early intervention.

In some embodiments, systems and methods described in this disclosure may be used for (6) identifying and/or tracking gum recession and/or abfractions. The systems and methods described herein may apply the described technology to identifying and/or gum recession and abfractions and are an improvement to existing methods. Currently, gum recession is tracked manually by a dental hygienist. This sometimes occurs infrequently due to time constraints which result in lost opportunities for early intervention. Gum recession can be caused by issues with the bite, tooth grinding, or aggressive brushing. It is often seen in conjunction with abfractions. Abfractions are notches in the sides of teeth that are an indicator of grinding. These occur due to the lateral flexion of teeth over time and can be prevented by using a night guard.

In some embodiments, systems and methods described in this disclosure may be used for (7) automatic charting of oral conditions, including for example existing restorations. The systems and methods described herein may apply the described technology to the automatic charting of oral conditions. Currently, hygienists are expected to chart existing restorations that a patient has by recording which surfaces have been filled. This process does not capture the size of a filling, and information gained from this process is limited. Also, this process occurs in a time-constrained setting which leads to errors from manual inputs. The time required to obtain this limited information could be better spent providing treatment to the patient. Automatic charting of oral conditions, thus, improves dental office efficiency.

In some embodiments, systems and methods described in this disclosure may be used for (8) automatic charting of oral conditions of pocket depths. The systems and methods described herein may apply the described technology to the automatic charting of periodontal pocket depths. In some embodiments, system may detect a length (i.e., depth) of periodontal pockets around teeth, for instance simultaneously with treatment, such as cleaning. In some cases, automatic periodontal depth charting may eliminate a need for manual probing by hygienist. Perio-probing is subjective and error prone. Currently, periodontal pocket depth is charted by taking three measurements on the buccal (check side) and three on the lingual (tongue side). In some cases, laser measurement may provide a more thorough scan and create a detailed simulation of the pocket to monitor. This combined with other technological applications described in this disclosure would likely eliminate any manual quantitative charting that the hygienist would need to do. Also, this process occurs in a time-constrained setting which leads to errors from manual inputs. The time required to obtain this limited information could be better spent providing treatment to the patient. Automatic charting of oral conditions, thus, improves dental office efficiency.

In some embodiments, systems and methods described in this disclosure may be used for (10) identifying the need and extent of cosmetic changes and minimizing the use of formulations in delivering cosmetic whitening. The systems and methods described herein may apply the described technology to the identification of cosmetic changes to oral tissue. Presently there is no method to identify and track a shade of tooth whiteness. Use of technology described in this disclosure may be applied to monitor and suggest a long-term whitening program that is effective without being time consuming.

Figure 2:
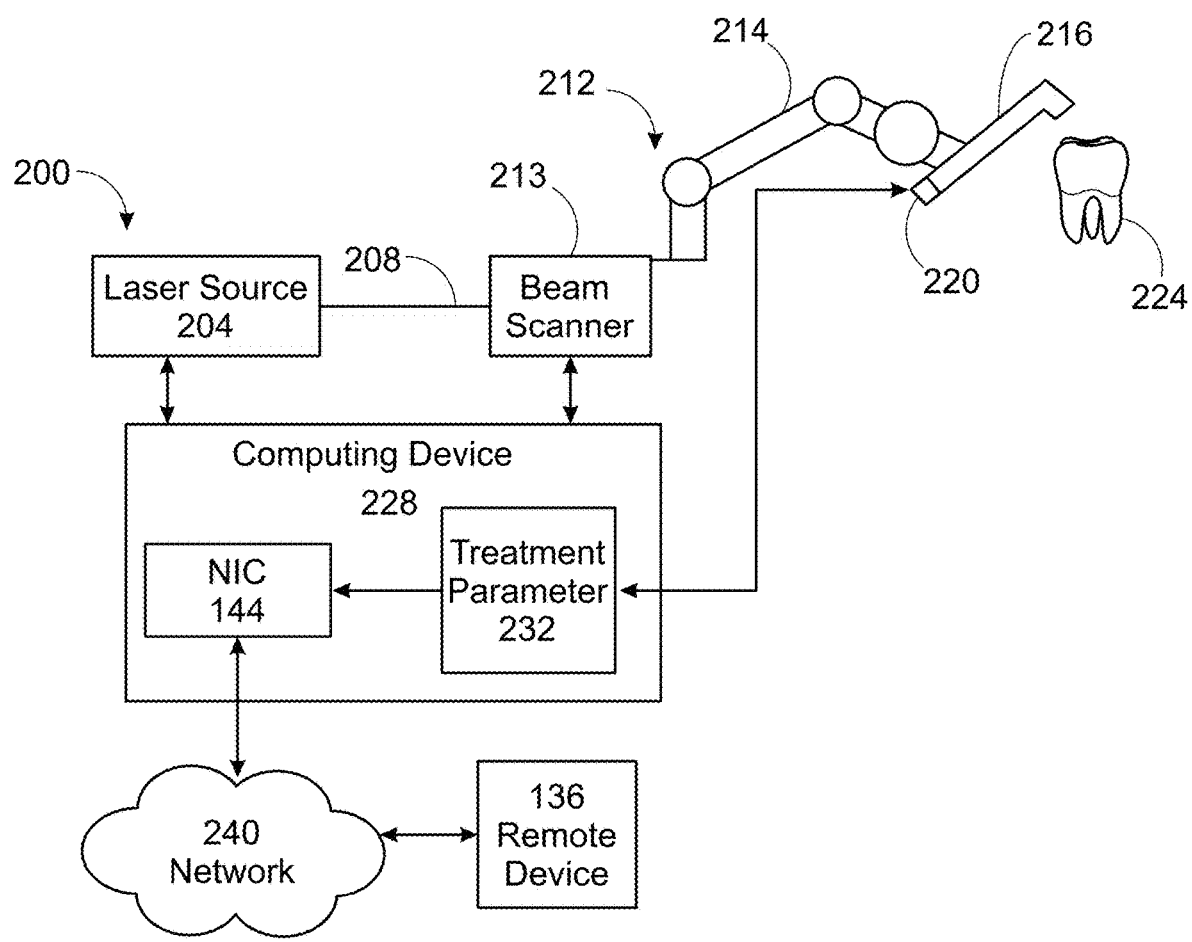
FIG. 2 illustrates a block diagram of the system for dental treatment and verification, in accordance with at least one embodiment.

FIG. 2 illustrates a block diagram of the system 200 for dental treatment and verification, in accordance with at least one embodiment. System 200 may include any system or constituent subsystem described in this disclosure. System 200 may include a laser 204. Laser 204 may include any laser described in this disclosure. Laser 204 may be configured to generate a laser beam 208, for instance as a function of a laser parameter. Laser beam 208 may include any laser beam described in this disclosure. Laser parameters may include any laser parameter described in this disclosure.

With continued reference to FIG. 2, system 200 may include a beam delivery system 212. Beam delivery system 212 may include any beam delivery system described in this disclosure; beam delivery system 212 may be configured to deliver laser beam 208 from laser 204. As described above, the beam delivery system 212 may include one or more of beam scanners 213 and an articulated arm 214.

With continued reference to FIG. 2, system 200 may include a hand piece 216. The hand piece 216 may include any hand piece described throughout this disclosure. As described above, the hand piece 216 may be configured to accept the laser beam 208 from the beam delivery system 212 and direct the laser beam 208 to dental tissue 224. Dental tissue 224 may include any dental tissue described in this disclosure, for instance, multiple enamel surfaces on multiple teeth in a mouth.

With continued reference to FIG. 2, system 200 may include a sensor 220, such as any sensor described throughout this disclosure. In some cases, sensor 220 may be configured to detect a treatment parameter as a function of a treatment phenomenon. A treatment parameter may include any representation of a treatment phenomenon. A treatment phenomenon may include any occurrence related to treatment, for example, dental laser treatment described in this disclosure. For example, in some cases, the treatment parameter may be an indication that at a certain time a laser beam was fired and/or directed to a certain location. Alternatively or additionally, a treatment phenomenon may include a visual representation of a dental treatment, such as without limitation a restorative procedure like filing, crown, bridge, implant, denture in-lay, on-lay, or the like. In some cases, a treatment parameter may include an image of visual representation of dental treatment. In some cases, computing device may chart a restorative procedure by locating a relative position of the restorative procedure within a mouth of a patient. Charting may also include classification of a type of restorative procedure, for instance restorations may be classified by number of sides prepared (i.e., drilled). In some cases, system 200 may automatically chart, by locating, classifying, and documenting, all restorative procedures visually detectable within a patient's mouth.

Still referring to FIG. 2, in some embodiments, sensor 220 may include a position sensor 220 and the treatment parameter represents a treated location. In some cases, a position sensor 220, such as a machine-vision camera, as described throughout, may detect a location of laser direction and/or irradiation at a time coincident with the firing of a laser beam. In some cases, the position sensor may include one or more of an inertial measurement unit, an accelerometer, and a gyroscope. In some cases, the position sensor may include an encoder, for example, a linear encoder and/or a rotary encoder. In some cases, the position sensor may include one or more rotary encoders located on rotational joints located on the articulated arm 214.

Still referring to FIG. 2, in some embodiments, the sensor may include a position sensor 220 including an optical sensor 220. The optical sensor may include any optical sensor described in this disclosure, for example, a photodiode, a photosensor, a camera, or the like. In some cases, an optical sensor may be active (using a light source) or passive. The optical sensor 220 may include a camera 220. Camera 220 may include any camera described in this disclosure. Optical sensor 220 may be used to determine a relative position in a mouth, for example as described throughout this application.

With continued reference to FIG. 2, system 200 may include a computing device 228. The computing device 228 may include any computing device described in this disclosure. The computing device 228 may be configured to receive treatment parameter 232 from the sensor 220. The computing device 228 may communicate with the sensor 220 using any communication method, network, and protocol described in this disclosure.

With continued reference to FIG. 2, computing device 228 may be configured to determine aggregated treated surfaces as a function of one or more of the treatment parameter 232 and the laser parameter. Representations (e.g., images) of treated surfaces may be aggregated using any method described in this method, for example, machine-learning processes and/or stitching methods. In some cases, the computing device may be configured to generate a three-dimensional representation of the treated location. In some cases, the computing device may be further configured to generate a treatment metric as a function of the aggregated treated surfaces; and communicate the treatment metric to a remote device. As used in this disclosure, a "treatment metric" is a measure of a treatment phenomenon. A treatment metric may include a spatial representation of surfaces treated with laser. In some cases, treatment metric may represent previous treatments, for instance, those not performed by laser or not performed concurrently with sensing. For example, in some cases, a treatment metric may include one or more representations of a type of restoration, a restoration material, a restoration location, a classification of restoration (e.g., number of sides restoration reaches), or the like. In some cases, treatment metric may be used to determine one or more of comprehensiveness of treatment, actual treatment performed, or the like. In some cases, treatment metric may be communicated, e.g., to a remote device, to compare actual treatment performed with treatment asserted and/or treatment invoiced.

Figure 3:
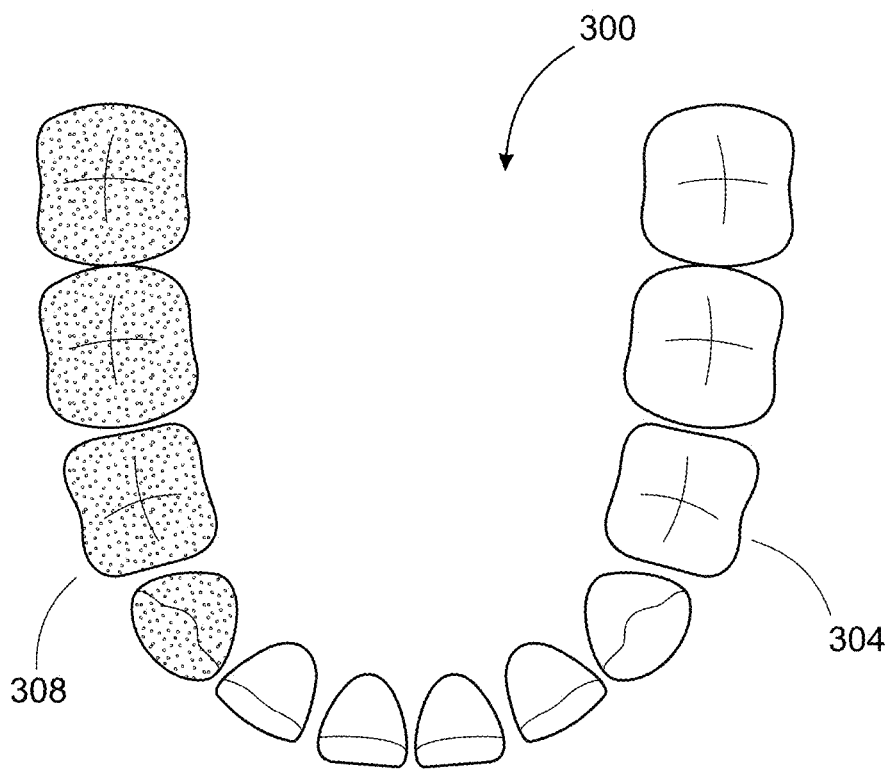
FIG. 3 illustrates a perspective view of a treatment verification in an arch of a mouth, in accordance with at least one embodiment.

FIG. 3 illustrates a perspective view of a treatment verification in an arch 300 of a mouth, in accordance with at least one embodiment. The arch 300 including a plurality of teeth is shown. In some cases, untreated teeth surfaces 304 may be differentiated from treated tooth surfaces 308. Treated tooth surfaces 308 may be aggregated and shown on a display device indicating to a user of the system where treatment has been performed. Additional disclosure related to present inventions may be found in U.S. Pat. App. Nos. 63/226,706, 63/149,354, 62/969,115, 62/968,922, 62/919, 154, Ser. Nos. 17/840,654, and 17/682,944, the entirety of each of which is incorporated herein by reference.

With continued reference to FIGS. 2-3, in another embodiment, a system 200 for dental treatment and verification includes a laser configured to generate a laser beam as a function of a laser parameter, a beam delivery system configured to deliver the laser beam from the laser, a hand piece configured to accept the laser beam from the beam delivery system and direct the laser beam to dental tissue, a sensor configured to detect a treatment parameter as a function of a treatment phenomenon, and a computing device configured to receive the treatment parameter from the sensor and determine aggregated treated surfaces as a function of the treatment parameter and the laser parameter. In some embodiments, the sensor comprises a position sensor and the treatment parameter represents a treated location. In some cases, the computing device is configured to generate a three-dimensional representation of the treated location. In some embodiments, the treatment parameter comprises an image of a restorative procedure. In some embodiments, the sensor comprises an optical sensor. In some cases, the optical sensor comprises a camera. In some embodiments, the computing device is further configured to generate a treatment metric as a function of one or more of the treatment parameter and the aggregated treated surfaces and communicate the treatment metric to a remote device. In some cases, generating the treatment metric comprises inputting one or more of the treatment parameter and a representation of the aggregated treated surfaces into a treatment metric machine learning model and outputting the treatment metric as a function of the treatment metric machine learning model and one or more of the treatment parameter and the representation of the aggregated treated surfaces. In some cases, generating the treatment metric further comprises training the treatment metric machine learning model by inputting a treatment metric training set into a machine learning algorithm, wherein the treatment metric training set correlates treatment metrics to one or more of the treatment parameter and the representation of the aggregated treated surfaces and training the treatment metric machine learning model as a function of the treatment metric training set and the machine learning algorithm. In some cases, the treatment metric is related to a treatment including one or more of cleaning, purifying, whitening, and alignment.

With continued reference to FIGS. 2-3, according to an embodiment herein, a method of dental treatment and verification includes generating, using a laser, a laser beam as a function of a laser parameter, delivering, using a beam delivery system, the laser beam from the laser, accepting, using a hand piece, the laser beam from the beam delivery system, directing, using the hand piece, the laser beam to dental tissue, detecting, using a sensor, a treatment parameter as a function of a treatment phenomenon, receiving, using a computing device, the treatment parameter from the sensor, and determining, using the computing device, aggregated treated surfaces as a function of the treatment parameter and the laser parameter. In some embodiments, the sensor comprises a position sensor and the treatment parameter represents a treated location. In some cases, the method additionally includes generating, using the computing device, a three-dimensional representation of the treated location. In some embodiments, the treatment parameter comprises an image of a restorative procedure. In some embodiments, the sensor comprises an optical sensor. In some cases, the optical sensor comprises a camera. In some embodiments, the method additionally includes generating, using the computing device, a treatment metric as a function of one or more of the treatment parameter and the aggregated treated surfaces and communicating, using the computing device, the treatment metric to a remote device. In some cases, generating the treatment metric comprises inputting one or more of the treatment parameter and a representation of the aggregated treated surfaces into a treatment metric machine learning model and outputting the treatment metric as a function of the treatment metric machine learning model and one or more of the treatment parameter and the representation of the aggregated treated surfaces. In some cases, generating the treatment metric further comprises training the treatment metric machine learning model by inputting a treatment metric training set into a machine learning algorithm, wherein the treatment metric training set correlates treatment metrics to one or more of the treatment parameter and the representation of the aggregated treated surfaces and training the treatment metric machine learning model as a function of the treatment metric training set and the machine learning algorithm. In some cases, the treatment metric is related to a treatment including one or more of cleaning, purifying, whitening, and alignment.

Figure 4:
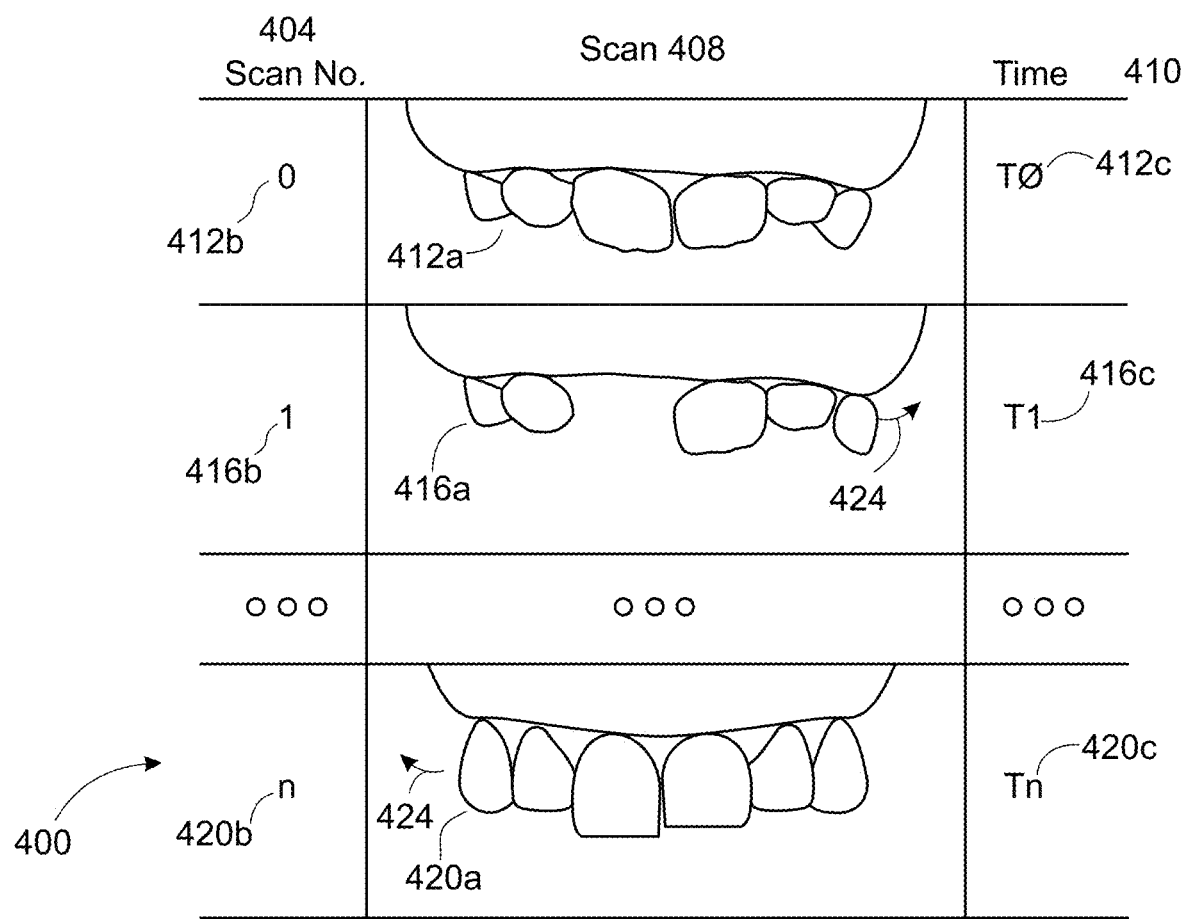
FIG. 4 illustrates a table of a series of oral images from an individual patient over a period of time, indicating misalignment of teeth, in accordance with at least one embodiment.

FIG. 4 illustrates a table 400 of a series of oral images from an individual patient over a period of time, in accordance with at least one embodiment. Table 400 illustrates image indices (Scan No.) at the left-most column 404 of the table 400. Table 400 illustrates oral images (Scans) in a middle column 408. Table 400 illustrates times at a right-most column 412. Table 400 may represent information stored, for instance in a memory, with each image index corresponding to an oral image and a time. In some cases, each oral image may include an aggregated oral image. As used in this disclosure, an "aggregated oral image" is a representation of oral tissue which comprises a plurality of oral images. In some cases, an aggregated oral image may represent more oral tissue (e.g., teeth) than any one of a plurality of oral images which constitute the aggregated oral image. In some cases, an aggregated oral image may include a three-dimensional representation; and the aggregated oral image represents and/or comprises a plurality of oral images which are two-dimensional representations. Aggregated oral image may be aggregated according to any method described in this disclosure, such as without limitation stitching, homography transform, affine transform, or the like. In some cases, an aggregated oral image may include or otherwise be associated with a chart that correlates individual teeth with the aggregated oral image to their respective number. Numbering of teeth may be done according to a tooth numbering method. A commonly used tooth numbering method starts at a rear-most right upper molar location and precedes to a rear left upper molar location, enumerating each tooth location from 1 to 16; bottom teeth locations are enumerated from left to right 17 to 32.

With continued reference to FIG. 4, a computing device may sense, generate, and/or receive oral images for an individual patient at different times, i.e., longitudinal oral data. Longitudinal oral data may include index numbers 404, oral image(s) (i.e., scan(s)) 408, and timestamps 410. For instance, a computing device may receive a first oral image 412a, having a first index 412b, representing oral tissue of a patient at a first time 412c; a second oral image 416a, having a second index 416b, representing oral tissue of the patient at a second time 416c. In some cases, the computing device may receive an additional oral image 420a, having an additional index 420b, representing the oral tissue of the patient at an additional time 420c.

With continued reference to FIG. 4, in some embodiments, oral images 408 may represent a patient's teeth while their bite alignment is changing or their teeth are coming in. For instance, in some cases, a patient may include a pediatric patient and earlier oral images 412a and 416b may include representations of deciduous teeth. In some cases, changes in bite alignment may be evident from changes in subsequent oral images 408. Movement of teeth 424, affecting alignment, may be determined through analysis of longitudinal data. Alternatively or additionally, future alignment changes may be predicted as a function of longitudinal data.

Figure 5A:
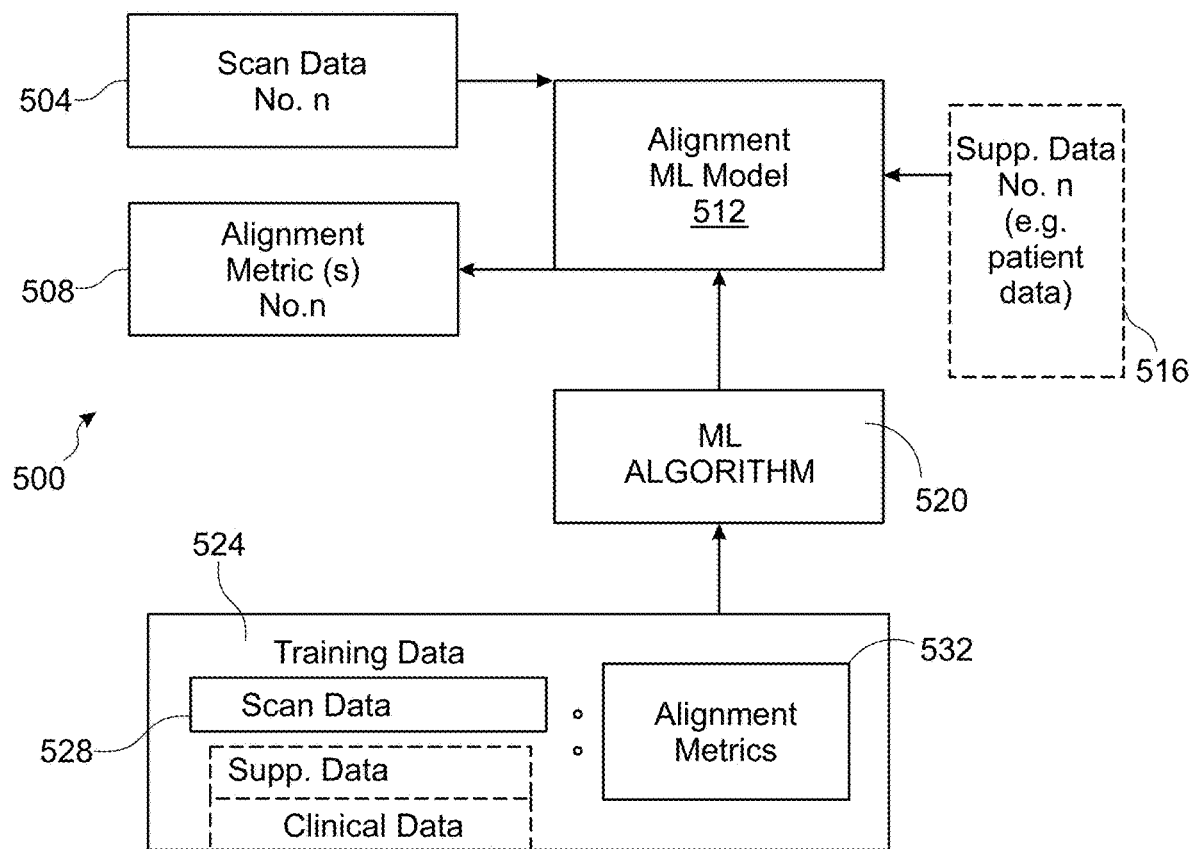
FIG. 5A illustrates a block diagram of an exemplary system for generating oral metrics as a function of oral images, in accordance with at least one embodiment.

FIG. 5A illustrates a block diagram of an exemplary system 500 for generating alignment metrics as a function of oral images, in accordance with at least one embodiment. System 500 may include one or more computing devices and/or laser treatment systems consistent with this disclosure. As used in this disclosure, an "alignment metric" is a quantifiable representation of an alignment phenomenon. An alignment phenomenon may include any occurrence within the mouth related to position/alignment of teeth or arrangement of bite. System 500 may be used to correlate an oral image 504 to an alignment metric 508. In some cases, alignment metric 508 may include one or more of an absolute position, a scalar position, a relative position, a vector, a direction, a size (e.g., of tooth or feature), or the like. In some cases, system 500 may include an alignment metric machine learning model 512. Alignment metric machine learning model 512 may include any machine learning model described in this disclosure, including supervised and unsupervised machine learning models. The alignment metric machine learning model may take as an input an oral image 504. The alignment metric machine learning model may output an alignment metric 508 as a function of oral image 504.

With continued reference to FIG. 5A, in some cases, alignment metric machine learning model 512 may take as input supplementary data 516. As used in this disclosure, "supplementary data" is optional data. Supplementary data may represent, without limitation, patient information (such as name, age, sex, name, and address of current or most recent treating clinician, past dental difficulties, chief complaint including duration, frequency, type, and intensity of any pain), treatment information, temporal information, patient cohort information, clinical information, or the like. Alignment metric machine learning model 512 may be configured to output an alignment metric 508 as a function of oral image 504 and supplementary data 516.

With continued reference to FIG. 5A, oral metric machine learning model 512 may be generated using an alignment metric machine learning process 520. Alignment metric machine learning process 520 may include any machine learning process and/or algorithm described in this disclosure. One of the ordinary skills in the art would appreciate that other currently known and future machine learning processes and/or algorithms can be interchanged with the machine learning processes used herein including one or more of the following methods: decision tree-based machine learning methods, artificial neural networks, logistic regression, naive Bayes, nearest neighbor, support vector machines, boosted tree learning methods, and deep learning methods. In some cases, alignment metric machine learning process 512 may be a supervised machine learning process. In some cases, alignment metric machine learning model 512 may be trained using alignment metric machine learning process 520 and alignment metric training data 524. Alignment metric training data 524 may include any training data (i.e., training data, training set, training data set) described in this disclosure. Alignment metric training data 524 may include historical oral images 528 correlated to historical alignment metrics 532. As used in this disclosure, "historical oral images" are oral images representing oral tissue at an earlier time (i.e., in the past). As used in this disclosure, "historical alignment metrics" are alignment metrics representing oral tissue at an earlier time (i.e., in the past). In some cases, alignment metric training data 524 may additionally correlate historical supplementary data with historical alignment metrics. As used in this disclosure, "historical supplementary data" is supplementary data that is representative of a phenomenon at an earlier time (i.e., in the past). In some cases, alignment metric training data 524 may be used with a supervised alignment metric machine learning model 520 to train alignment metric machine learning model 512. In some cases, training of alignment metric machine learning model may be performed on a device remote from the computing device upon which the machine learning model is implemented (e.g., used to correlate input oral images to output oral metrics).

Figure 5B:
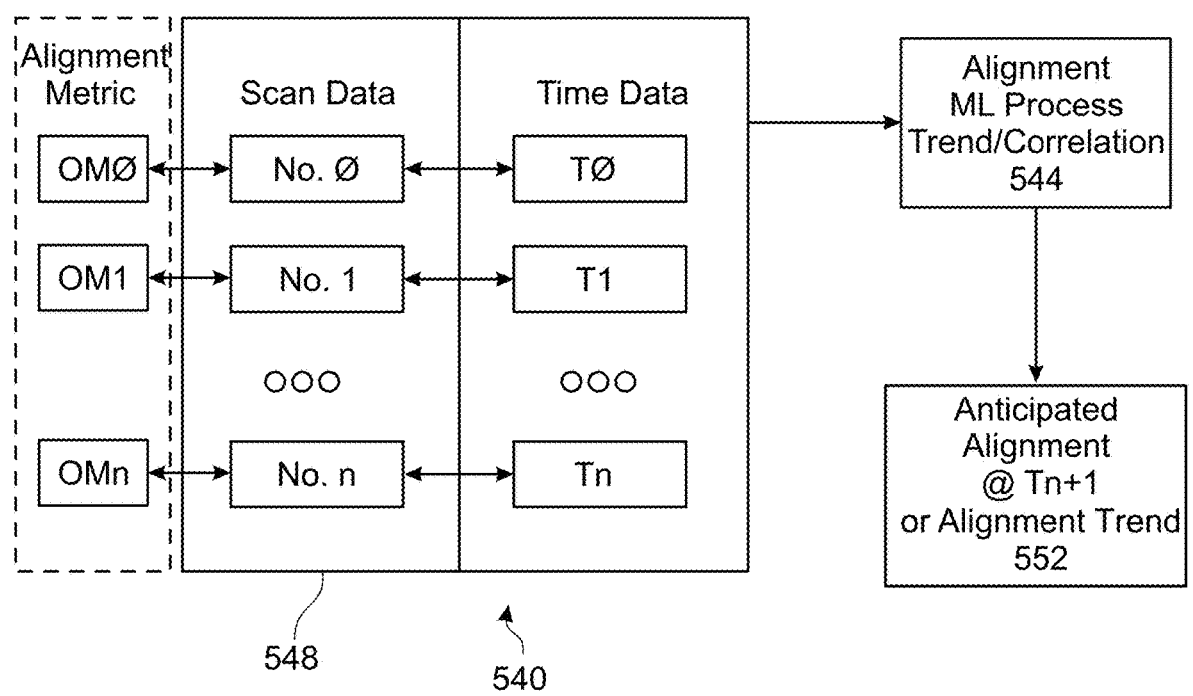
FIG. 5B illustrates a block diagram of an exemplary system for predicting a future oral condition, in accordance with at least one embodiment.

Referring now to FIG. 5B, an exemplary system 540 for predicting a future bite or teeth alignment or alignment trend 552 is illustrated. System 540 may include one or more computing devices and/or laser treatment systems consistent with this disclosure. System 540 may include an alignment prediction machine-learning process 544. Alignment prediction machine-learning process 544 may include any machine-learning process, algorithm, and/or model described in this disclosure, including without limitation prediction machine learning process and/or prediction machine learning model described below. In some cases, alignment prediction machine-learning process 544 may include an unsupervised machine-learning process. In an embodiment, the alignment prediction machine-learning process 544 is based on one or more of a regression model, a neural network, K-Means Clustering, Principal Component Analysis, and Hierarchical Clustering. System 540 may receive oral data 548. As used in this disclosure, "oral data" is information that includes some representation of the oral phenomenon.

With continued reference to FIGS. 4, 5A-B, according to an embodiment herein, a system for estimating future bite arrangement includes a scheduling system, configured to schedule a patient for detecting a plurality of oral images representing a plurality of exposed tooth surfaces on a plurality of the patient's teeth, a sensor configured to periodically detect the plurality of oral images as a function of the schedule, and a computing device configured to: receive the plurality of oral images from the sensor, aggregate a first aggregated oral image as a function of the plurality of oral images at a first time, aggregate a second aggregated oral image as a function of the plurality of oral images at a second time, and estimate a future bite arrangement as a function of the first aggregated oral image and the second aggregated oral image.

With continued reference to FIGS. 4, 5A-B, in another embodiment, a method of estimating future bite arrangement includes scheduling, using a scheduling system, a patient for detecting a plurality of oral images representing a plurality of exposed tooth surfaces on a plurality of the patient's teeth, periodically detecting, using a sensor, the plurality of oral images as a function of the schedule, receiving, using a computing device, the plurality of oral images from the sensor, aggregating, using the computing device, a first aggregated oral image as a function of the plurality of oral images at a first time, aggregating, using the computing device, a second aggregated oral image as a function of the plurality of oral images at a second time, and estimating, using the computing device, a future bite arrangement as a function of the first aggregated oral image and the second aggregated oral image.

With continued reference to FIGS. 4, 5A-5B, according to an embodiment herein, a system for estimating future bite arrangement includes a scheduling system, a sensor, and a computing device. The scheduling system is configured to schedule a patient for detecting a plurality of oral images representing a plurality of exposed tooth surfaces on a plurality of the patient's teeth. The sensor is configured to detect the plurality of oral images as a function of oral phenomena and a computing device configured to receive the plurality of oral images from the sensor, aggregate an aggregated oral image as a function of the plurality of oral images, and estimate a future bite arrangement as a function of the aggregated oral image. In some embodiments, the aggregated oral image comprises a three-dimensional representation of oral tissue. In some embodiments, aggregating the aggregated oral image further comprises identifying at least a common feature in a first oral image and a second oral image of the plurality of oral images and transforming one or more of the first oral image and the second oral image as a function of the at least a common feature. In some cases, aggregating the aggregated oral image further comprises blending a demarcation between the first oral image and the second oral image. In some cases, blending the demarcation comprises comparing pixel values between overlapping pixels in the first oral image and the second oral image and altering the demarcation as a function of the comparison. In some embodiments, altering the demarcation comprises minimizing a difference in value between overlapping pixels between the first oral image and the second oral image along the demarcation. In some embodiments, estimating the future bite arrangement comprises inputting the aggregated oral image to a bite estimation machine learning model and estimating the future bite arrangement using the bite estimation machine learning model. In some embodiments, estimating the future bite arrangement further comprises inputting bite estimation training data into a machine learning processes, wherein the bite estimation training data correlates oral images to subsequent bite arrangements and training the bite estimation machine learning model, using the bite estimation training data. In some embodiments, estimating the future bite arrangement further comprises classifying the aggregated oral image and selecting the bite estimation training data from a plurality of training data as a function of the classification of the aggregated oral image. In some embodiments, classifying the aggregated oral image is performed as a function of patient information.

With continued reference to FIGS. 4, 5A-5B, according to an embodiment herein, a method of estimating future bite arrangement includes detecting, using a sensor, a plurality of oral images as a function of oral phenomena, receiving, using a computing device, the plurality of oral images from the sensor, aggregating, using the computing device, an aggregated oral image as a function of the plurality of oral images and estimating, using the computing device, a future bite arrangement as a function of the aggregated oral image. In some embodiments, the aggregated oral image comprises a three-dimensional representation of oral tissue. In some embodiments, aggregating the aggregated oral image further comprises identifying at least a common feature in a first oral image and a second oral image of the plurality of oral images and transforming one or more of the first oral image and the second oral image as a function of the at least a common feature. In some cases, aggregating the aggregated oral image further comprises blending a demarcation between the first oral image and the second oral image. In some cases, blending the demarcation comprises comparing pixel values between overlapping pixels in the first oral image and the second oral image and altering the demarcation as a function of the comparison. In some cases, altering the demarcation comprises minimizing a difference in value between overlapping pixels between the first oral image and the second oral image along the demarcation. estimating the future bite arrangement comprises inputting the aggregated oral image to a bite estimation machine learning model and estimating the future bite arrangement using the bite estimation machine learning model. In some cases, estimating the future bite arrangement further comprises inputting bite estimation training data into a machine learning processes, wherein the bite estimation training data correlates oral images to subsequent bite arrangements and training the bite estimation machine learning model, using the bite estimation training data. In some cases, estimating the future bite arrangement further comprises classifying the aggregated oral image and selecting the bite estimation training data from a plurality of training data as a function of the classification of the aggregated oral image. In some cases, classifying the aggregated oral image is performed as a function of patient information.

Figure 6A:
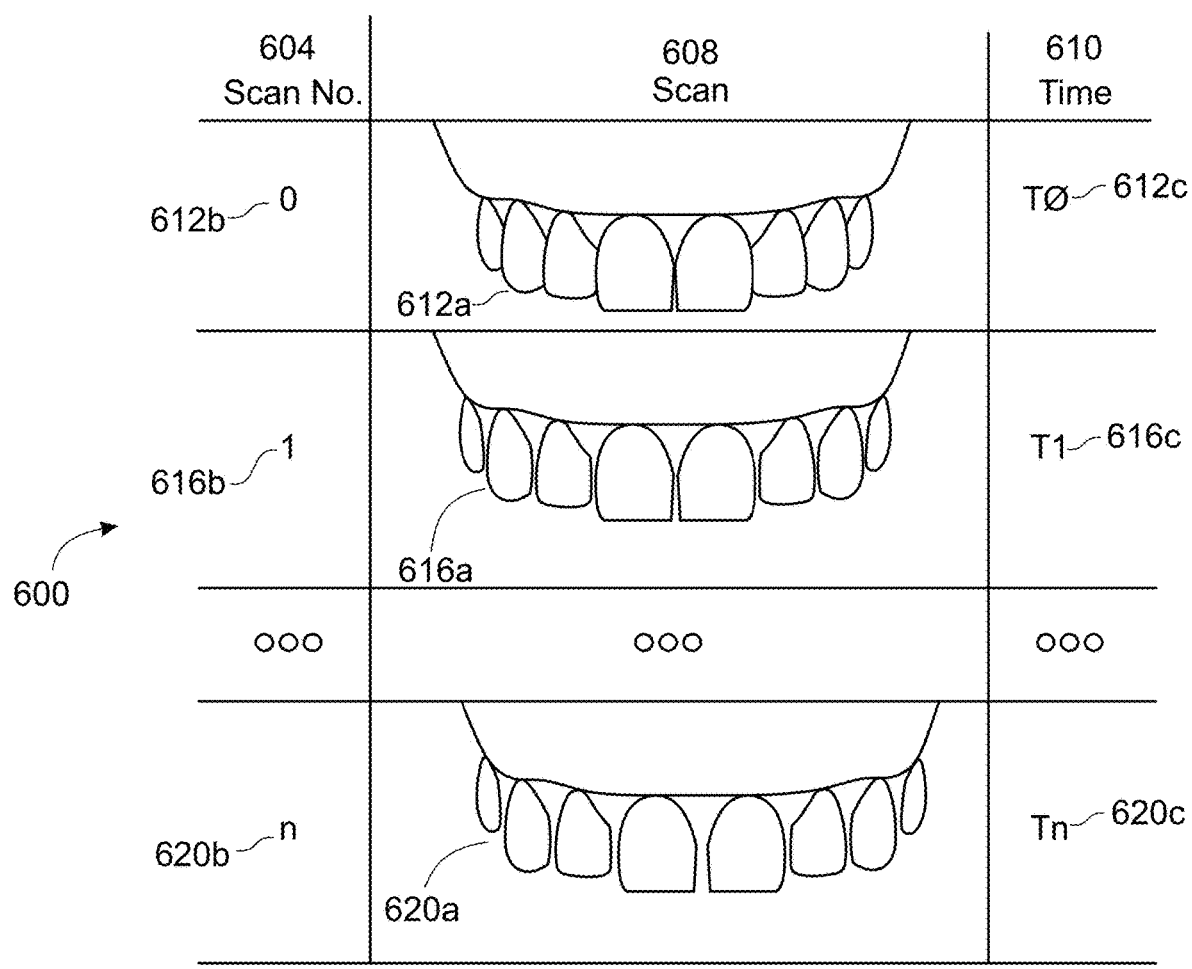
FIG. 6A illustrates a table of a series of images of dental hard tissue captured over time, indicating attrition of the teeth, in accordance with at least one embodiment.

FIG. 6A illustrates a table 600 of a series of images of dental hard tissue captured over time, indicating attrition of the teeth, in accordance with at least one embodiment. Table 600 illustrates image indices (Scan No.) at the left-most column 604, oral images (Scans) in a middle column 608, and times at a right-most column 612. Table 600 may represent information stored, for instance in a memory, with each image index corresponding to an oral image and a time. In some cases, each oral image may include an aggregated oral image.

With continued reference to FIG. 6A, oral images may show attrition of dental tissue over time. For instance, without limitation, oral images 608 may indicate dental hard tissue attrition, as shown in FIG. 6A, including erosion, wear, bruxism, abfraction, or the like. Alternatively or additionally, oral images 608 may indicate dental soft tissue attrition, such as gum recession.

With continued reference to FIG. 6A, a computing device may sense, generate, and/or receive oral images for an individual patient at different times. For instance, a computing device may receive a first oral image 612a, having a first index 612b, representing oral tissue of a patient at a first time 612c; a second oral image 616a, having a second index 616b, representing oral tissue of the patient at a second time 616c, wherein the oral tissue of the patient at the second time 616c is shown to have lost tissue when compared to the oral tissue of the patient at the first time 612c. In some cases, the computing device may receive an additional oral image 620a, having an additional index 620b, representing the oral tissue of the patient at an additional time 620c, wherein the oral tissue of the patient at the additional time 620c is shown to have lost tissue when compared to the oral tissue of the patient at the second time 614c.

Figure 6B:
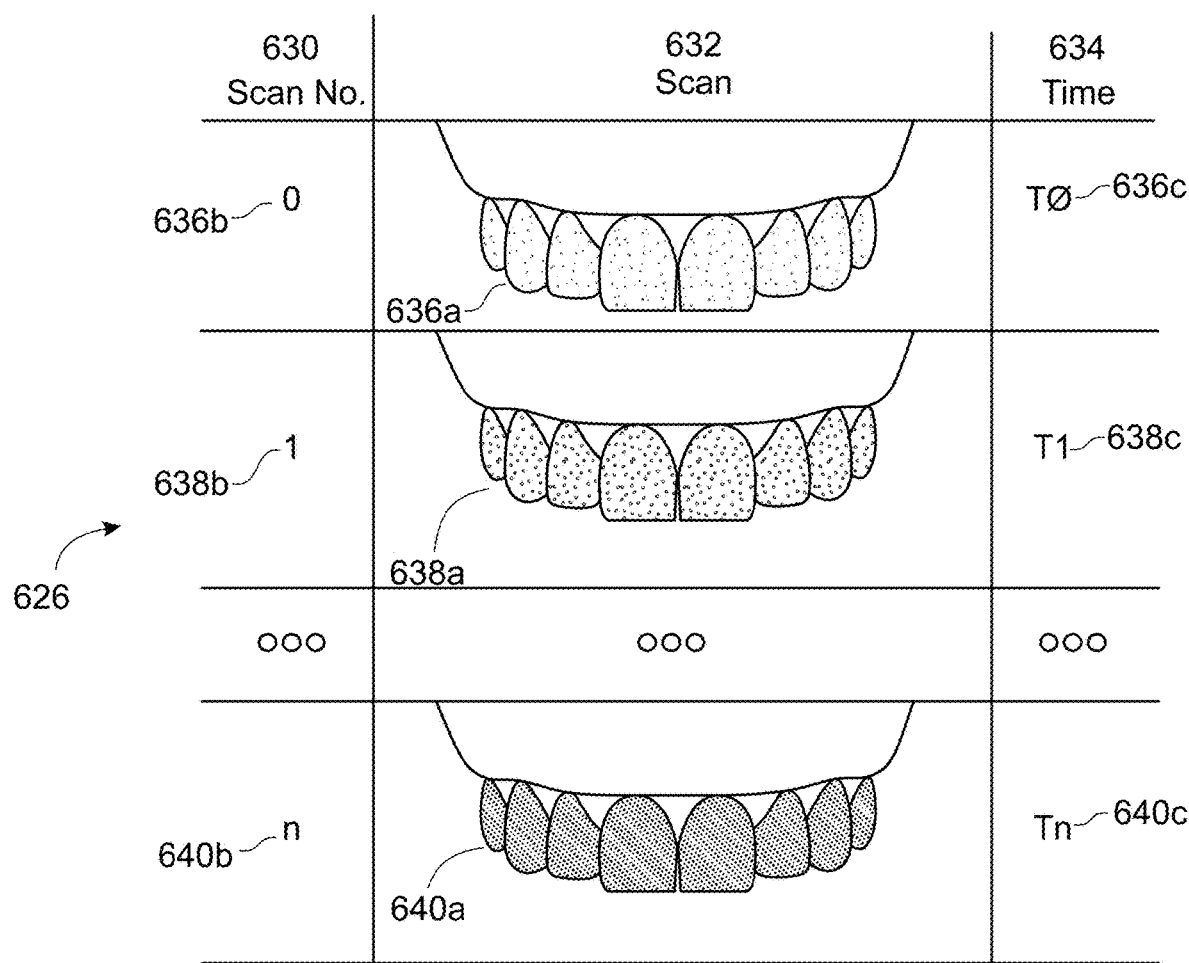
FIG. 6B illustrates a table of a series of images of dental hard tissue captured over time (indicating discoloration of the teeth), in accordance with at least one embodiment.

FIG. 6B illustrates a table 626 of a series of images of dental hard tissue captured over time, indicating discoloration of the teeth, in accordance with at least one embodiment. Table 626 illustrates image indices (Scan No.) at the left-most column 630, oral images (Scans) in the middle column 632, and times at a right-most column 634. Table 626 may represent information stored, for instance in a memory, with each image index corresponding to an oral image and a time. In some cases, each oral image may include an aggregated oral image.

With continued reference to FIG. 6B, oral images may show discoloration of dental tissue over time. For instance, without limitation, oral images 632 may indicate dental hard tissue discoloration, as shown in FIG. 6B, including staining, or the like.

With continued reference to FIG. 6B, a computing device may sense, generate, and/or receive oral images for an individual patient at different times. For instance, a computing device may receive a first oral image 636a, having a first index 636b, representing oral tissue of a patient at a first time 636c; a second oral image 638a, having a second index 638b, representing oral tissue of the patient at a second time 638c, wherein the oral tissue of the patient at the second time 638c is shown to have increased discoloration when compared to the oral tissue of the patient at the first time 636c. In some cases, the computing device may receive an additional oral image 640a, having an additional index 640b, representing the oral tissue of the patient at an additional time 640c, wherein the oral tissue of the patient at the additional time 640c is shown to have increased discoloration when compared to the oral tissue of the patient at the second time 638c.

Figure 6C:
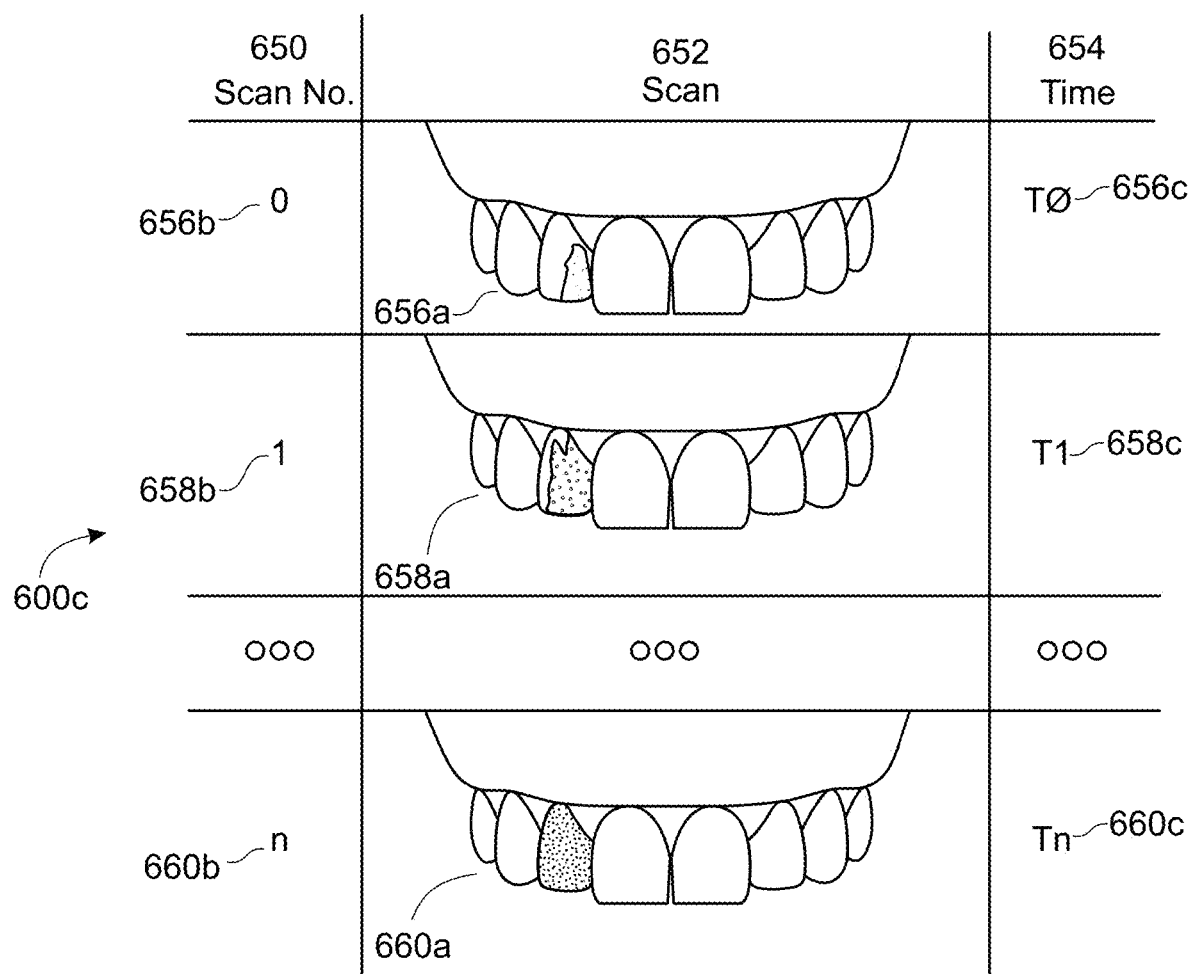
FIG. 6C illustrates a table of a series of images of dental hard tissue captured over time, indicating decay of the teeth, in accordance with at least one embodiment.

FIG. 6C illustrates a table 646 of a series of images of dental hard tissue captured over time, indicating decay of the teeth, in accordance with at least one embodiment. Table 646 illustrates image indices (Scan No.) at the left-most column 650, oral images (Scans) in a middle column 652, and times at a right-most column 654. Table 646 may represent information stored, for instance in a memory, with each image index corresponding to an oral image and a time. In some cases, each oral image may include an aggregated oral image.

With continued reference to FIG. 6C, oral images may show decay of dental tissue over time. For instance, without limitation, oral images 652 may indicate dental hard tissue decay, as shown in FIG. 6C, including caries, white spot lesions, or the like. Alternatively or additionally, in some cases, oral images 652 may show soft tissue pathologies, such as without limitation gum recession, gum disease, periodontal disease, soft tissue inflammation, or the like.

With continued reference to FIG. 6C, a computing device may sense, generate, and/or receive oral images for an individual patient at different times. For instance, a computing device may receive a first oral image 656a, having a first index 656b, representing oral tissue of a patient at a first time 656c; a second oral image 658a, having a second index 658b, representing oral tissue of the patient at a second time 658c, wherein the oral tissue of the patient at the second time 658c is shown to have increased decay when compared to the oral tissue of the patient at the first time 656*c*. In some cases, the computing device may receive an additional oral image 660*a*, having an additional index 660*b*, representing the oral tissue of the patient at an additional time 660*c*, wherein the oral tissue of the patient at the additional time 660*c* is shown to have increased decay when compared to the oral tissue of the patient at the second time 658*c*.

Figure 7A:
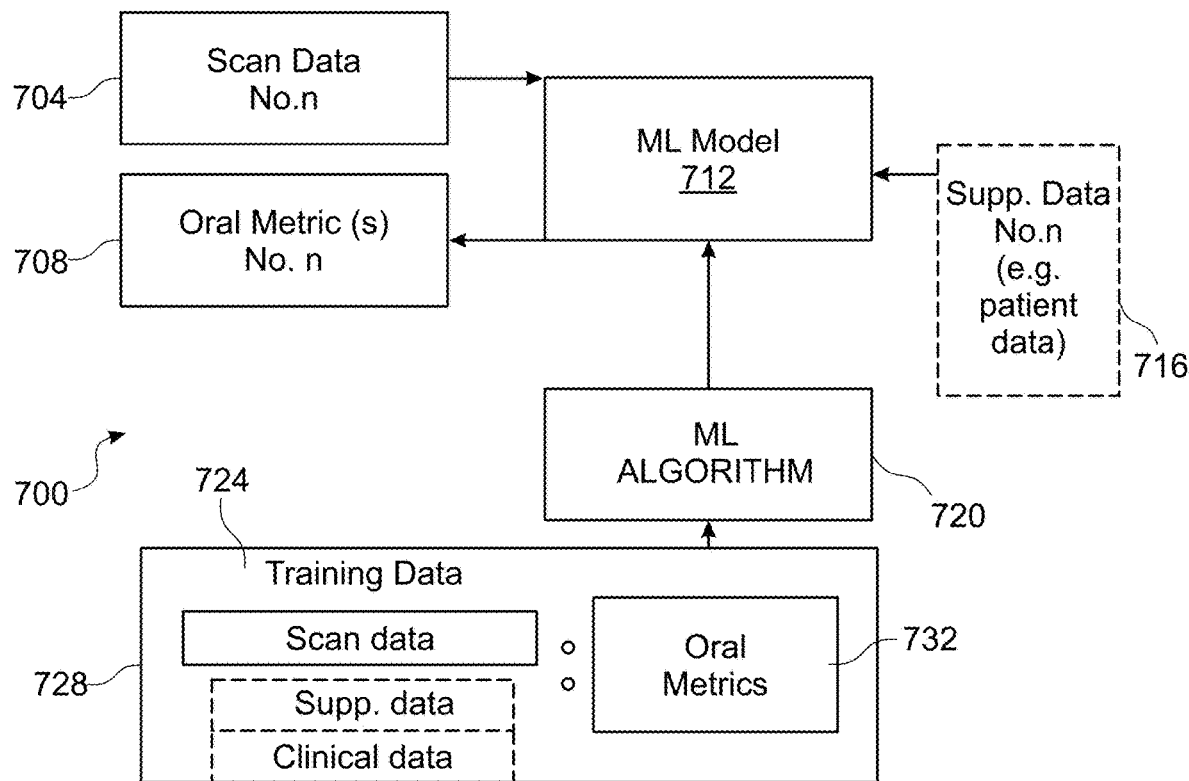
FIG. 7A illustrates a block diagram of the system implementing machine learning processes for quantifying an oral metric using images captured at a single time or taken over time, in accordance with at least one embodiment.

FIG. 7A illustrates a block diagram of the system 700 implementing machine learning processes for quantifying oral conditions using images, (captured at a single time or taken over time,) in accordance with at least one embodiment. System 700 may include one or more computing devices and/or laser treatment systems consistent with this disclosure. System 700 be used to correlate an oral image 704 and to an oral metric 708. As used in this disclosure, an "oral metric" is a quantifiable representation of an oral phenomenon. An oral phenomenon may include any occurrence within the mouth and may be referred to as a dental phenomenon within this disclosure, without great divergence in meaning between the two terms. Oral phenomena include without limitation bite arrangement (i.e., alignment), dental tissue color (i.e., whiteness), dental tissue attrition (e.g., wear, erosion, etc.), dental tissue decay (e.g., demineralization, caries, etc.), or the like. In an embodiment, oral metric 708 may be related to one or more of erosion, attrition, or wear. Alternatively or additionally, oral metric 708 may be related to one or more of discoloration, alignment, or decay. In some cases, oral metric 708 may include one or more of attrition metric, alignment metric (see disclosure above), whiteness metric, and/or decay metric. As used in this disclosure, "attrition metric" is a measure of phenomenon related to attrition of dental tissue, for example erosion or wear of dental hard tissue. Attrition metric 708 may include spatial measurements of dental hard or soft tissue. For example, precise size (e.g., height or width) of dental tissue (relative a fiducial) may be incorporated within an attrition metric. As used in this disclosure, "whiteness metric" is a measure of a phenomenon related to color of dental hard tissue, for example whiteness of enamel and/or dentin. In some cases, whiteness metric may include a photometric measurement, analysis, and/or classification of dental hard tissue, for example under certain lighting and imaging conditions. Whiteness metric may be considered a species within a group of "color metrics," which according to this disclosure are measures of phenomena associated with color and/or visible light. In some cases, color metrics may be used to quantify phenomena associated with inflammation in dental soft tissue, such as gums. As used in this disclosure, "decay metric" is a measure of a phenomenon associated with dental decay, such as without limitation caries. An exemplary non-limiting decay metric may include an estimated quantification of demineralization. In some cases, a decay metric may be related to an optical phenomena, such as without limitation reflection, transmission, scatter, and/or absorption of light. In some cases, optical phenomena may be wavelength dependent, for instance fluorescence is an optical phenomenon which is dependent upon excitation wavelength and emission wavelength.

With continued reference to FIG. 7A, In some cases, system 700 may include an oral metric machine learning model 712. Oral metric machine learning model 712 may include any machine learning model described in this disclosure. The oral metric machine learning model may take as an input an oral image 704. The oral metric machine learning model may output an oral metric 708 as a function of oral image 704.

With continued reference to FIG. 7A, in some cases, oral metric machine learning model 712 may take as input supplementary data 716. Oral metric machine learning model 712 may be configured to output an oral metric 708 as a function of oral image 704 and supplementary data 716.

With continued reference to FIG. 7A, oral metric machine learning model 712 may be generated using an oral metric machine learning process 720. Oral metric machine learning process 720 may include any machine learning process and/or algorithm described in this disclosure. In some cases, oral metric machine learning model 512 is trained using oral metric machine learning process 520 and oral metric training data 524. Oral metric training data 524 may include any training data (i.e., training data, training set, training data set) described in this disclosure. Oral metric training data 524 may include historical oral images 528 correlated to historical oral metrics 532. In some cases, oral metric training data 524 may additionally correlate historical supplementary data with historical oral metrics. In some cases, oral metric training data 524 may be used with a supervised oral metric machine learning model 520 to train oral metric machine learning model 512.

Figure 7B:
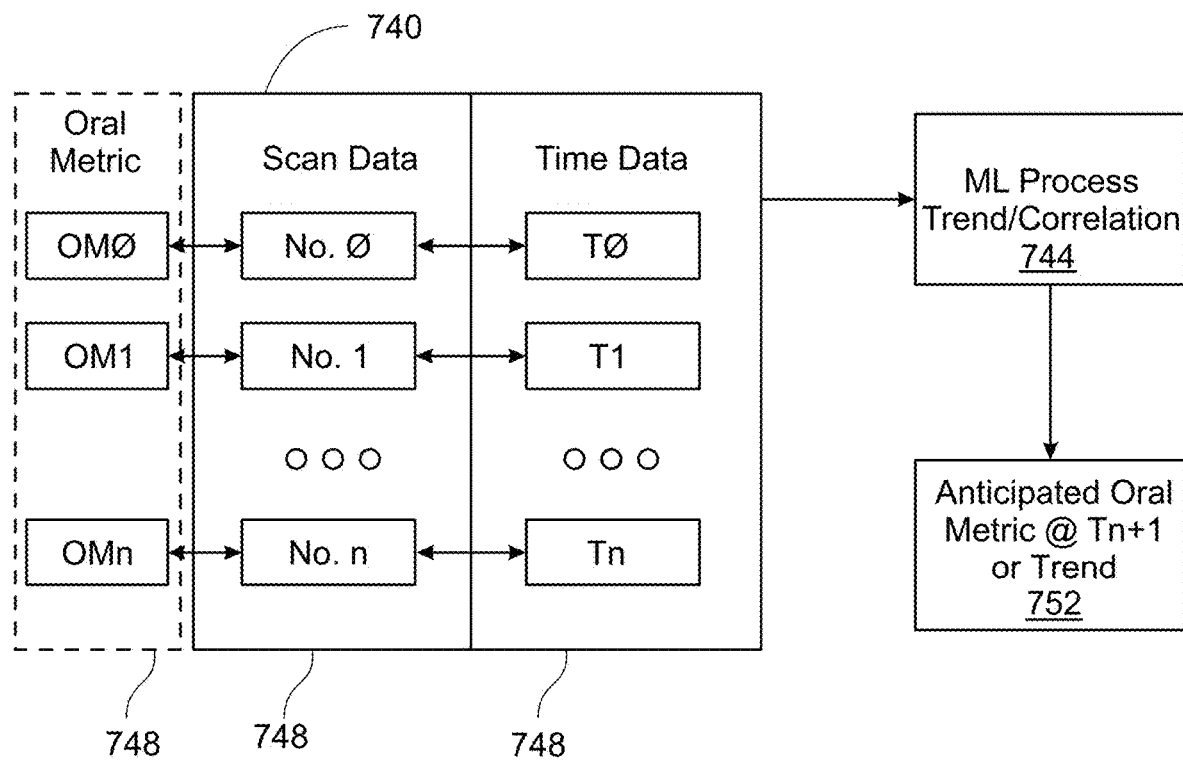
FIG. 7B illustrates a block diagram of the system implementing the machine learning process for estimating a trend using one or more of oral metrics and images, in accordance with at least one embodiment.

FIG. 7B illustrates a block diagram 740 of the system implementing the ML process for estimating future erosion using one or more of erosion metrics and images, in accordance with at least one embodiment. System 740 may include one or more computing devices and/or laser treatment systems consistent with this disclosure. System 740 may include a prediction machine-learning process 544. Prediction machine-learning process 744 may include any machine-learning process, algorithm, and/or model described in this disclosure. Prediction machine learning process may include alignment prediction machine learning process, as described above. In some cases, prediction machine-learning process 744 may include an unsupervised machine-learning process, which may use, for example, interpolative/extrapolative processes or the like. In some cases, prediction machine learning process may include a classifier, which classifies oral data 748 to a class, for instance through nearest-neighbor or fuzzy set processes as described below. System 740 may receive oral data 748. Oral data 748 may include any oral data described in this disclosure, for example without limitation oral metrics, oral images, dental parameters, treatment parameters, or the like. Prediction machine learning process 744 may output one or more of a trend or anticipated oral data 752. Trend may include a representation of change in oral data or condition (e.g., bite alignment, attrition, erosion, wear, decay, discoloration, gum recession, or the like) in relation to time (i.e., time in future). Anticipated oral data may include a predicted quantification (e.g., oral metric) or representation of an oral condition (e.g., bite alignment, attrition, erosion, wear, decay, discoloration, gum recession, or the like) at some time in future, such as without limitation 6 months, one year, two years, five years, 10 years, 20 years, or the like, in the future. In some cases, prediction machine learning process 744 may include a prediction machine learning model 744. Prediction machine learning model 744 may be trained using a prediction training set. Prediction training set may include historical and/or simulated oral data which may be correlated with one or more of trends and later oral data. In some cases, prediction training set may include oral data taken longitudinally using one or more patients, and earlier oral data may be used to train the prediction machine learning process/model by correlating with later oral data, for example through interpolation and/or extrapolation.

With continued reference to FIGS. 6A-6C, 7A-7B, in another embodiment, a system for estimating a trend includes a sensor configured to periodically detect a plurality of oral images representing a plurality of exposed tooth surfaces, as a function of a schedule and a computing device configured to receive the plurality of oral images from the sensor, aggregate a first aggregated oral image as a function of the plurality of oral images at a first time, aggregate a second aggregated oral image as a function of the plurality of oral images at a second time, and estimate a trend as a function of the first aggregated oral image and the second aggregated oral image. In some embodiments, a scheduling system is configured to schedule a patient for detecting a plurality of oral images representing a plurality of exposed tooth surfaces on a plurality of the patient's teeth. In some embodiments, the patient includes a pediatric patient. In some cases, the pediatric patient has deciduous teeth. In some embodiments, the trend includes an attrition trend. In some embodiments, the trend includes a future bite arrangement. In some embodiments, the trend includes an alignment trend. In some embodiments, the trend includes a decay trend. In some embodiments, the trend includes a discoloration trend. In some embodiments, estimating the trend comprises a machine learning process.

With continued reference to FIGS. 6A-6C, 7A-7B, according to an embodiment herein, a method of estimating a trend includes periodically detecting, using a sensor, the plurality of oral images as a function of the schedule, receiving, using a computing device, the plurality of oral images from the sensor, aggregating, using the computing device, a first aggregated oral image as a function of the plurality of oral images at a first time, aggregating, using the computing device, a second aggregated oral image as a function of the plurality of oral images at a second time, and estimating, using the computing device, a future bite arrangement as a function of the first aggregated oral image and the second aggregated oral image. In some embodiments, scheduling, using a scheduling system, a patient for detecting a plurality of oral images representing a plurality of exposed tooth surfaces on a plurality of the patient's teeth. In some embodiments, the patient includes a pediatric patient. In some cases, the pediatric patient has deciduous teeth. In some embodiments, the trend includes an attrition trend. In some embodiments, the trend includes a future bite arrangement. In some embodiments, the trend includes an alignment trend. In some embodiments, the trend includes a decay trend. In some embodiments, the trend includes a discoloration trend. In some embodiments, estimating the trend comprises a machine learning process.

Figure 7C:
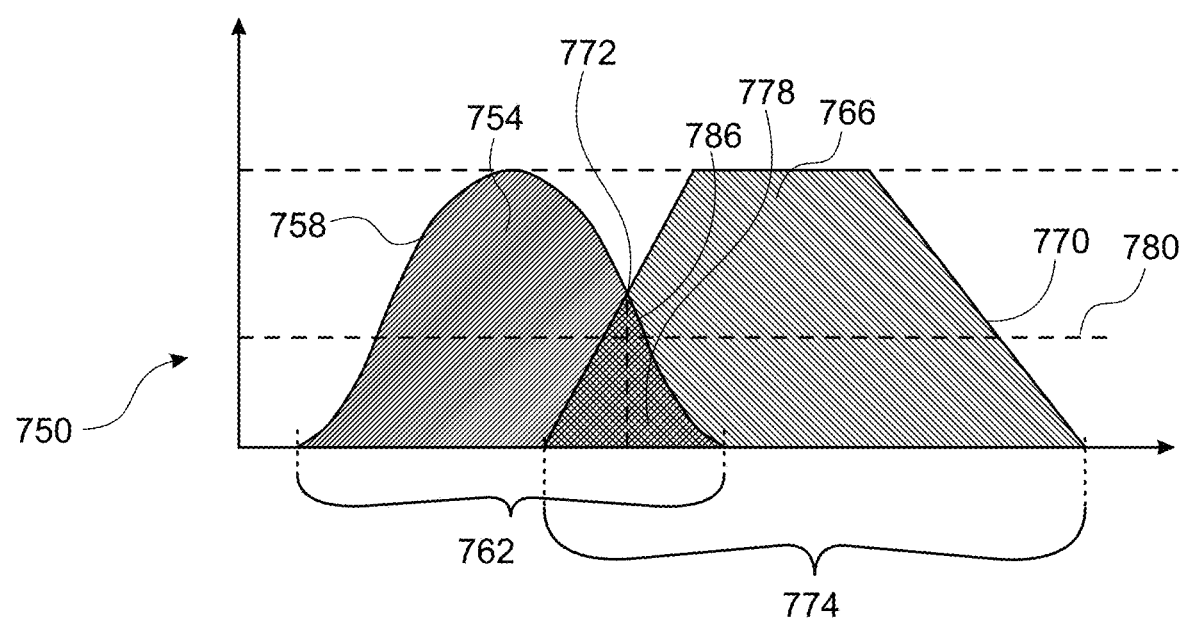
FIG. 7C illustrates a graphical representation of fuzzy set comparison, in accordance with at least one embodiment.

FIG. 7C illustrates a graphical representation of fuzzy set comparison 750, in accordance with at least one embodiment. A first fuzzy set 754 may be represented, without limitation, according to a first membership function 758 representing a probability that an input falling on a first range of values 762 is a member of the first fuzzy set 754, where the first membership function 758 has values on a range of probabilities such as without limitation the interval [0,1], and an area beneath the first membership function 758 may represent a set of values within first fuzzy set 754. Although the first range of values 762 is illustrated for clarity in this exemplary depiction as a range on a single number line or axis, the first range of values 762 may be defined on two or more dimensions, representing, for instance, a Cartesian product between a plurality of ranges, curves, axes, spaces, dimensions, or the like. First membership function 758 may include any suitable function mapping first range 762 to a probability interval, including without limitation a triangular function defined by two linear elements such as line segments or planes that intersect at or below the top of the probability interval. As a non-limiting example, the triangular membership function may be defined as:

$$y(x, a, b, c) = \begin{cases} 0, \text{ for } x > c \text{ and } x < a \\ \frac{x-a}{b-a}, \text{ for } a \leq x < b \\ \frac{c-x}{c-b}, \text{ if } b < x \leq c \end{cases}$$

a trapezoidal membership function may be defined as:

$$y(x, a, b, c, d) = \max\left(\min\left(\frac{x-a}{b-a}, 1, \frac{d-x}{d-c}\right), 0\right)$$

a sigmoidal function may be defined as:

$$y(x, a, c) = \frac{1}{1 - e^{-a(x-c)}}$$

a Gaussian membership function may be defined as:

$$y(x, c, \sigma) = e^{-\frac{1}{2}\left(\frac{x-c}{\sigma}\right)^2}$$

and a bell membership function may be defined as:

$$y(x, a, b, c,) = \left[1 + \left|\frac{x-c}{a}\right|^{2b}\right]^{-1}$$

Persons skilled in the art, upon reviewing the entirety of this disclosure, will be aware of various alternative or additional membership functions that may be used consistently with this disclosure.

Still referring to FIG. 7C, first fuzzy set 754 may represent any value or combination of values as described above, including output from one or more machine-learning models, such as an image correspondence machine learning model, a diagnosis machine learning model, and a prediction machine learning model, and a predetermined class. In an embodiment, predetermined class may include classifications of training data. For instance, training data may be classified according to patient demographic (e.g., age, sex, profession, or the like), patient cohort, individual patient, diagnosis, or the like. In some embodiments, an image may be classified to a predetermined class. In some cases, a dental parameter may be classified into a predetermined class. In some embodiments, a feature (within an image) may be classified to a predetermined class. For instance, a feature within an image representative of an oral feature may be classified to a predetermined class, including oral features such as without limitation cusps, interproximal regions, and the like. Additional or alternative examples of predetermined class may include but are not limited to a treatment metric, a future bite arrangement, classification of an aggregated oral image, alignment trend, attrition trend, discoloration trend, decay trend, classification of a dental parameter, or the like. A second fuzzy set 766, which may represent any value that may be represented by the first fuzzy set 754, may be defined by a second membership function 770 on a second range 774; second range 774 may be identical and/or overlap with the first range 762 and/or may be combined with first range via Cartesian product or the like to generate a mapping permitting evaluation overlap of first fuzzy set 754 and second fuzzy set 766. Where first fuzzy set 754 and second fuzzy set 766 have a region 778 that overlaps, first membership function 758 and second membership function 770 may intersect at a point 772 representing a probability, as defined on probability interval, of a match between the first fuzzy set 754 and second fuzzy set 766. Alternatively, or additionally, a single value of the first and/or second fuzzy set may be located at a locus 786 on the first range 762 and/or second range 774, where a probability of membership may be taken by evaluation of first membership function 758 and/or second membership function 770 at that range point. A probability at 778 and/or 772 may be compared to a threshold value 780 to determine whether a positive match is indicated. Threshold 780 may, in a non-limiting example, represent a degree of match between first fuzzy set 754 and second fuzzy set 766, and/or single values therein with each other or with either set, which is sufficient for purposes of the matching process; for instance, threshold may indicate a sufficient degree of overlap between an output from one or more machine-learning models, such as image correspondence machine learning model, diagnosis machine learning model, oral metric machine learning model, alignment metric machine learning model, prediction machine learning model, or the like, and a predetermined class, such as without limitation diagnosis, trend, anticipated oral metric, anticipate alignment metric, correspondence, feature, charting (location), restoration type categorization, for combination to occur as described above. Alternatively, or additionally, each threshold may be tuned by a machine-learning and/or statistical process, for instance, and without limitation, as described in further detail below.

Further referring to FIG. 7C, in an embodiment, a degree of match between fuzzy sets may be used to classify one or more of at least an oral image, at least an oral metric, and/or at least an alignment metric with a trend. For instance, if at least an oral metric has a fuzzy set matching a trend fuzzy set by having a degree of overlap exceeding a threshold, computing device may classify the at least an oral metric as belonging to the trend categorization. Where multiple fuzzy matches are performed, degrees of a match for each respective fuzzy set may be computed and aggregated through, for instance, addition, averaging, or the like, to determine an overall degree of match.

Still referring to FIG. 7C, in an embodiment, one or more of at least an oral image, at least an oral metric, and/or at least an alignment metric may be compared to multiple categorization fuzzy sets. Categorization fuzzy sets may include trend categorization fuzzy sets, correspondence categorization fuzzy sets, feature categorization fuzzy sets, treatment categorization fuzzy sets (which categorizes to restoration type, location, charting, treatment location, or the like), or the like. For instance, at least an oral image may be represented by a fuzzy set that is compared to each of the multiple categorization fuzzy sets; and a degree of overlap exceeding a threshold between the at least an oral image fuzzy set and any of the multiple categorization fuzzy sets may cause computing device to classify the at least an oral image as belonging to a categorization. For instance, in one embodiment there may be two treatment categorization fuzzy sets, representing respectively class I restoration categorization and a class II restoration categorization. First, class I restoration categorization may have a first fuzzy set; Second class II restoration categorization may have a second fuzzy set; and at least an oral image (or portion thereof) may have an at least an oral image fuzzy set. The computing device, for example, may compare an the at least an oral image fuzzy set with each of class I restoration categorization fuzzy set and in class II restoration categorization fuzzy set, as described above, and classify a images of restorations on one or more teeth within the at least an oral image to either, both, or neither of class I restoration categorization or in class II restoration categorization. Machine-learning methods as described throughout may, in a non-limiting example, generate coefficients used in fuzzy set equations as described above, such as without limitation x, c, and σ of a Gaussian set as described above, as outputs of machine-learning methods. Likewise, detected parameters (e.g., treatment parameters, dental parameters, oral images, and the like) may be used indirectly to determine a fuzzy set, as a fuzzy set may be derived from outputs of one or more machine-learning models that take the detected parameters directly or indirectly as inputs.

Still referring to FIG. 7C, a computing device may use a logic comparison program, such as, but not limited to, a fuzzy logic model to determine a response. A response may include, but is not limited to, nominal, mild, moderate, advanced, excessive, and the like; each such response may be represented as a value for a linguistic variable representing response or in other words a fuzzy set as described above that corresponds to a degree of overlap with a categorization as calculated using any statistical, machine-learning, or other methods that may occur to a person skilled in the art upon reviewing the entirety of this disclosure. In some embodiments, determining a categorization may include using a linear regression model. A linear regression model may include a machine learning model. A linear regression model may be configured to map data, to one or more categories. A linear regression model may be trained using a machine-learning process. A linear regression model may map statistics. In some embodiments, an classification model may be configured to input data (e.g., oral images, oral metrics, or the like) and cluster data to a centroid based on, but not limited to, frequency of appearance, linguistic indicators noted by a dental professional, and the like. Centroids may include scores assigned to them. In some embodiments, a classification model may include a K-means clustering model. In some embodiments, a classification model may include a particle swarm optimization model. In some embodiments, determining a classification model may include using a fuzzy inference engine. A fuzzy inference engine may be configured to map one or more data elements using fuzzy logic. In some embodiments, one or more of oral metrics and oral images may be arranged by a logic comparison program into an arrangement. An arrangement as used in this disclosure is any grouping of objects and/or data. This step may be implemented as described in this disclosure. Membership function coefficients and/or constants as described in this disclosure may be tuned according to classification and/or clustering algorithms. For instance, and without limitation, a clustering algorithm may determine a Gaussian or other distribution of questions about a centroid corresponding to a given level, and iterative or other methods may be used to find a membership function, for any membership function type as described above, that minimizes an average error from the statistically determined distribution, such that, for instance, a triangular or Gaussian membership function about a centroid representing a center of the distribution that most closely matches the distribution. Error functions to be minimized, and/or methods of minimization, may be performed without limitation according to any error function and/or error function minimization process and/or method as described in this disclosure.

Further referring to FIG. 7C, an inference engine may be implemented according to input and/or output membership functions and/or linguistic variables. For instance, a first linguistic variable may represent a first measurable value pertaining to alignment such as a degree of misalignment of bite, while a second membership function may indicate a degree of attrition of teeth, or another measurable value pertaining to attrition, discoloration, decay, or the like. Continuing the example, an output linguistic variable may represent, without limitation, a score value. An inference engine may combine rules—the degree to which a given input function membership matches a given rule may be determined by a triangular norm or "T-norm" of the rule or output membership function with the input membership function, such as min (a, b), product of a and b, a drastic product of a and b, Hamacher product of a and b, or the like, satisfying the rules of commutativity (T(a, b)=T(b, a)), monotonicity: (T(a, b)≤T(c, d) if a≤c and b≤d), (associativity: T(a, T(b, c))=T(T(a, b), c)), and the requirement that the number 1 acts as an identity element. Combinations of rules ("and" or "or" combination of rule membership determinations) may be performed using any T-conorm, as represented by an inverted T symbol or "⊥," such as max(a, b), a probabilistic sum of a and b (a+b−a*b), bounded sum, and/or drastic T-conorm; any T-conorm may be used that satisfies the properties of commutativity: ⊥(a, b)=⊥(b, a), monotonicity: ⊥(a, b)≤⊥(c, d) if a≤c and b≤d, associativity: ⊥(a, ⊥(b, c))=⊥(⊥(a, b), c), and identity element of 0. Alternatively, or additionally, T-conorm may be approximated by sum, as in a "product-sum" inference engine in which T-norm is the product and T-conorm is a sum. A final output score or other fuzzy inference output may be determined from an output membership function as described above using any suitable defuzzification process, including without limitation Mean of Max defuzzification, Centroid of Area/Center of Gravity defuzzification, Center Average defuzzification, Bisector of Area defuzzification, or the like. Alternatively, or additionally, output rules may be replaced with functions according to the Takagi-Sugeno-King (TSK) fuzzy model.

Figure 7D:
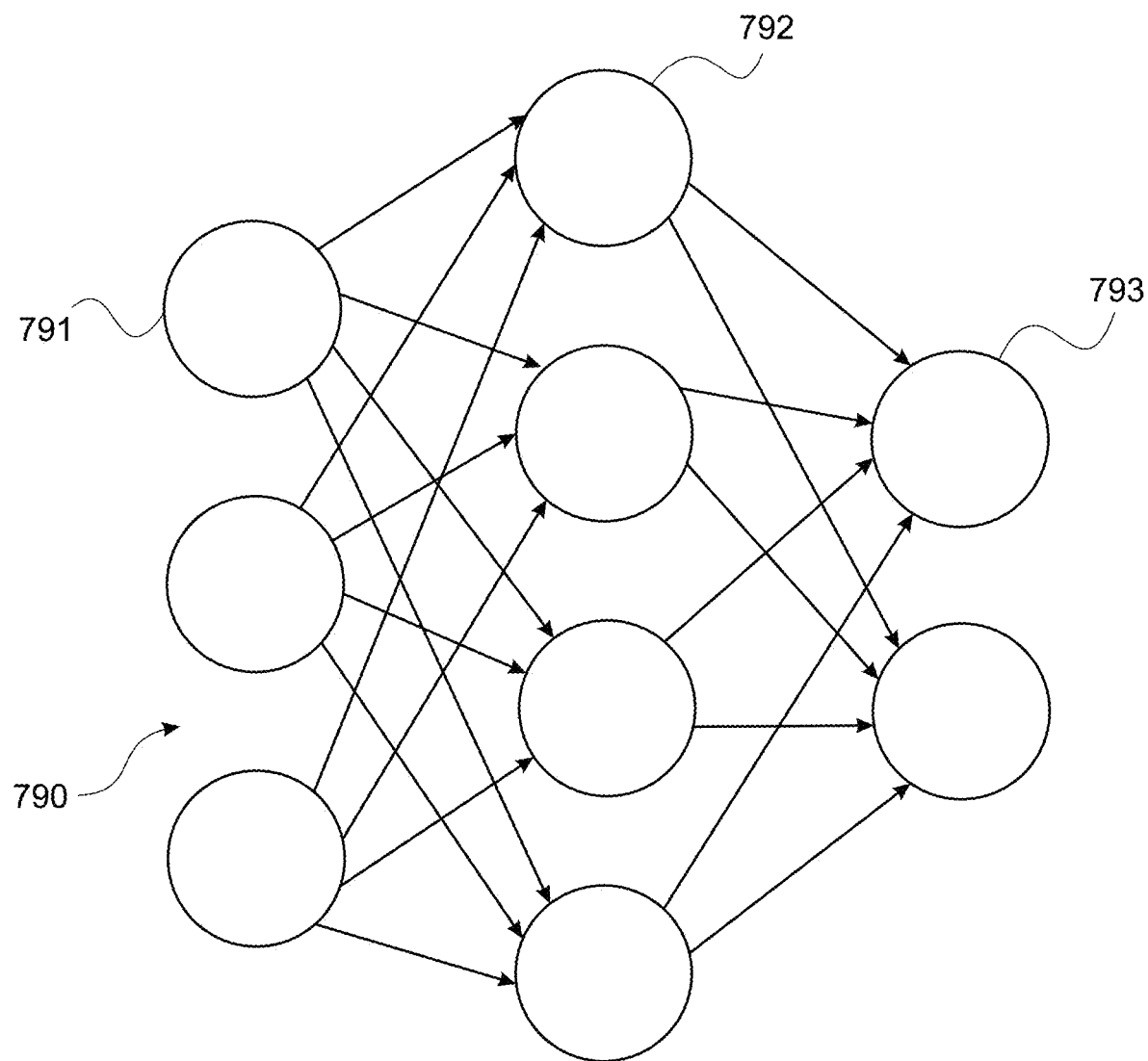
FIG. 7D illustrates an exemplary embodiment of a neural network, in accordance with at least one embodiment.

FIG. 7D illustrates an exemplary embodiment of a neural network 790, in accordance with at least one embodiment. A neural network 790 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 791, one or more intermediate layers 792, and an output layer of nodes 793. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 7E:
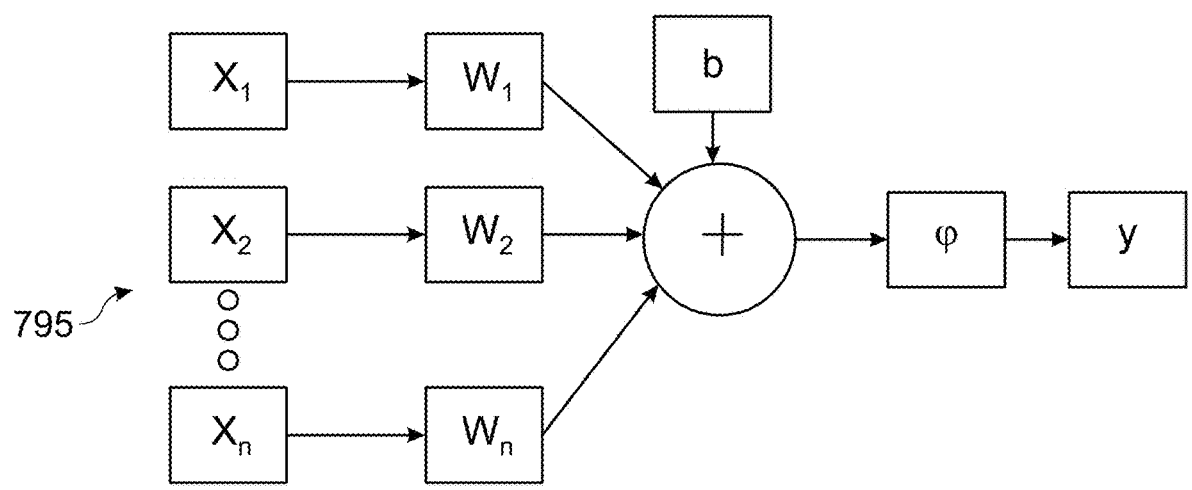
FIG. 7E illustrates an exemplary embodiment of a node of a neural network, in accordance with at least one embodiment.

FIG. 7E illustrates an exemplary embodiment of node 795 of a neural network, in accordance with at least one embodiment. A node may include, without limitation a plurality of inputs xi that may receive numerical values from inputs to a neural network containing the node and/or from other nodes. The node may perform a weighted sum of inputs using weights $w_i$ that are multiplied by respective inputs xi. Additionally, or alternatively, a bias b may be added to the weighted sum of the inputs such that an offset is added to each unit in the neural network layer that is independent of the input to the layer. The weighted sum may then be input into a function co, which may generate one or more outputs y. Weight $w_i$ applied to an input xi may indicate whether the input is "excitatory," indicating that it has a strong influence on the one or more outputs y, for instance by the corresponding weight having a large numerical value, and/or an "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 8:
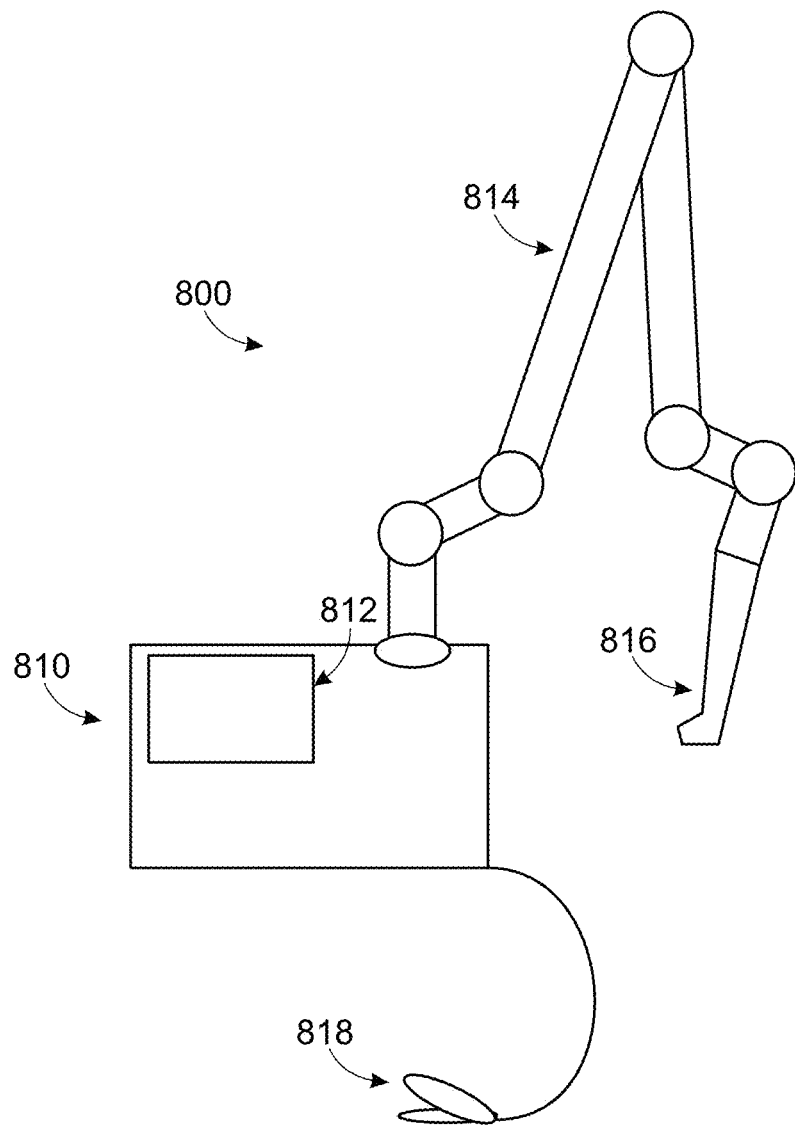
FIG. 8 illustrates a console that houses various components of the system, in accordance with at least one embodiment.

FIG. 8 illustrates a console that houses various components of the system 800, in accordance with at least one embodiment. The system 800 includes a console 810. The console 810 houses components of the system 800, for example, a laser source to generate the laser beam, a direct current (DC) power supply to power the laser source, a beam shaper to shape an energy profile of the laser beam, a compressed air system to deliver compressed air for bulk cooling of dental hard tissue being treated, and a user interface 812 for user control. A beam delivery system 814 directs the laser beam to a hand piece 816. Exemplary beam delivery systems 814 include articulated arms, waveguides, and fiber optics. An exemplary articulated arm is provided by Laser Mechanisms of Novi, Michigan, U.S.A. The hand piece 816 is configured to be used intra-orally (i.e., within an oral cavity). Typically, the hand piece 816 includes a focus optic (not shown) that converges the laser beam to a focal region outside of the hand piece 816. In accordance with one embodiment, the system 900 is operated with a foot pedal 818, which is configured to initiate the laser source.

In accordance with one embodiment, the system 800 is used by a clinician. First, the clinician inputs operating parameters into the user interface 812, for example by using a touch screen. Then the clinician places the hand piece 816 within a patient's mouth and directs the hand piece 816 toward dental hard tissue. For example, the clinician positions the hand piece 816 so that a focal region of the laser beam is coincident with or near (e.g., +/−1 mm, 2 mm, 3 mm, or 5 mm) a surface of a tooth. Then, the clinician activates the laser by stepping on a foot pedal 818. The clinician moves the hand piece 816 within the patient's mouth, carefully directing the focal region of the laser beam near every treatment surface of the patient's teeth.

To aid in the practice of the claimed invention and parameter selection a table is provided below with exemplary ranges and nominal values for relevant parameters.

| Parameter | Min. | Max. | Nom. |
|---|---|---|---|
| Repetition Rate | 1 Hz | 100 KHz | 1 KHz |
| Pulse Energy | 1 μJ | 10 J | 10 mJ |
| Focal Region Width | 1 μm | 10 mm | 1 mm |
| Fluence | 0.01 J/cm$^2$ | 1 MJ/cm$^2$ | 1 J/cm$^2$ |
| Wavelength | 200-500 nm | 4000-12000 nm | 10.6 μm |
| Numerical Aperture (NA) | 0.00001 | 0.5 | 0.01 |
| Focal length | 10 mm | 1000 mm | 200 mm |
| Average Power | 1 mW | 100 W | 1 W |
| Peak Power | 50 mW | 5000 W | 500 W |
| Scan Speed | 0.001 mm/S | 10 mm/S | 100,000 mm/S |
| Scan Location Spacing | 0 | 0.5 × Focal Region Width | 10 × Focal Region Width |
| Correspondence | <=25 micrometers | <=150 micrometers | <=1 mm |
| Resolution | <=25 micrometers | <=150 micrometers | <=500 micrometers |
| Bleaching Agents | Hydrogen Peroxide, Carbamide Peroxide, Sodium Perborate | | |
| Remineralizing and/or Desensitizing Agents | Fluorides (see below), Nonfluoride remineralizing agents (e.g., Alpha tricalcium phosphate [TCP] and beta TCP [β-TCP], Amorphous calcium phosphate [ACP], casein phosphopeptide-stabilized amorphous calcium phosphate [CPP-ACP], Sodium calcium phosphosilicate [bioactive glass], Xylitol, Dicalcium phosphate dehydrate [DCPD], Nanoparticles for remineralization [e.g., Calcium fluoride nanoparticles, Calcium phosphate-based nanomaterials, NanoHydroxyapatite {NanoHAP} particles, ACP nanoparticles, Nanobioactive glass materials]), Polydopamine, proanthocyanidin [PA], Oligopeptides, Theobromine, Arginine, Self-assembling peptides, and Electric field-induced remineralization | | |
| Fluoride Agents | Sodium Fluoride, Stannous Fluoride, Titanium Tetrafluoride, Acidulated-Phosphate Fluoride, and Amine Fluoride | | |
| Subsurface imaging | X-ray, magnetic resonance imaging (MRI), computed tomography scan, ultrasonic imaging, or the like. | | |
| Optic materials | Zinc Sulfide, Zinc Selenide, Silicon, Germanium, Quartz, Calcium Fluoride, Magnesium Fluoride, Sodium Chloride, Potassium Bromide, and Barium Fluoride. | | |

Exemplary Embodiment

Further explanation is provided below with an exemplary embodiment demonstrating effective treatment of dental surfaces to prevent deterioration common with aging.

Method—A 9.3 nm CO$_2$ laser was used. The laser was a Luxinar OEM45ix. The laser was operated at an average power, of not more than 1 W. Output from the laser was directed by three reflectors and aligned into a galvanometer scan head. The laser was output from the galvanometer scan head and focused by focusing optics. The width of the laser focal region was determined using a 90-10 knife edge method. A knife (e.g., razor blade) was placed in front of the beam at the focal region and scanned transversely to the laser axis. A thermopile was used to measure the laser power down the beam from the knife edge. The knife edge location where the laser power is found to be at 10% and 90% was measured using a calibrated stage. This distance (i.e., 90-10 knife edge distance) was used to estimate the 1/e$^2$ beam width. The 1/e$^2$ beam width was then used to determine the desired pulse energy from a fluence (i.e., energy density) range known to affect treatment without melting: between about 0.5 and 1.0 J/cm$^2$. The pulse energy was calculated by measuring the average power using a thermopile (Ophir PN: 30A-BB-18) and dividing by an average repetition rate, determined by an oscilloscope (PicoScope 2205A) measuring the amplified signal from a fast infrared photodiode (Hamamatsu PN: C12494-011LH). A laser scan pattern was developed using ScanLab software. A laser controller controlled the laser and the galvanometers to deliver the laser beam deterministically according to the scan pattern. The scan pattern sequentially delivered individual laser pulses to individual scan locations, to increase the effective treatment area of the laser beam, without increasing the focal region width (which would require greater laser energy per pulse to maintain the necessary energy density [fluence]). Additionally, each sequential pulse in the scan pattern was delivered to a location, which is non-adjacent to the previous pulse, with 7 individual laser pulses elapsing between adjacent pulses. This method of spacing sequential pulses maximized the amount of time between adjacent pulses, which allowed more time for the surface to cool the post-laser pulse to its initial temperature before another laser pulse acting at the same (or proximal) location was delivered. The laser scan pattern width was approximately 2.5 mm wide. An effective treatment area of this size or larger allows for a clinically viable treatment speed. For example, it was estimated that the treatable surface area of teeth in the mouth is about 2500 mm$^2$, from available anatomical data. A 2.5 mm wide laser treatment, if scanned over the teeth at a rate of 5 mm/S, will theoretically be completed in a little under four minutes.

Figure 9:
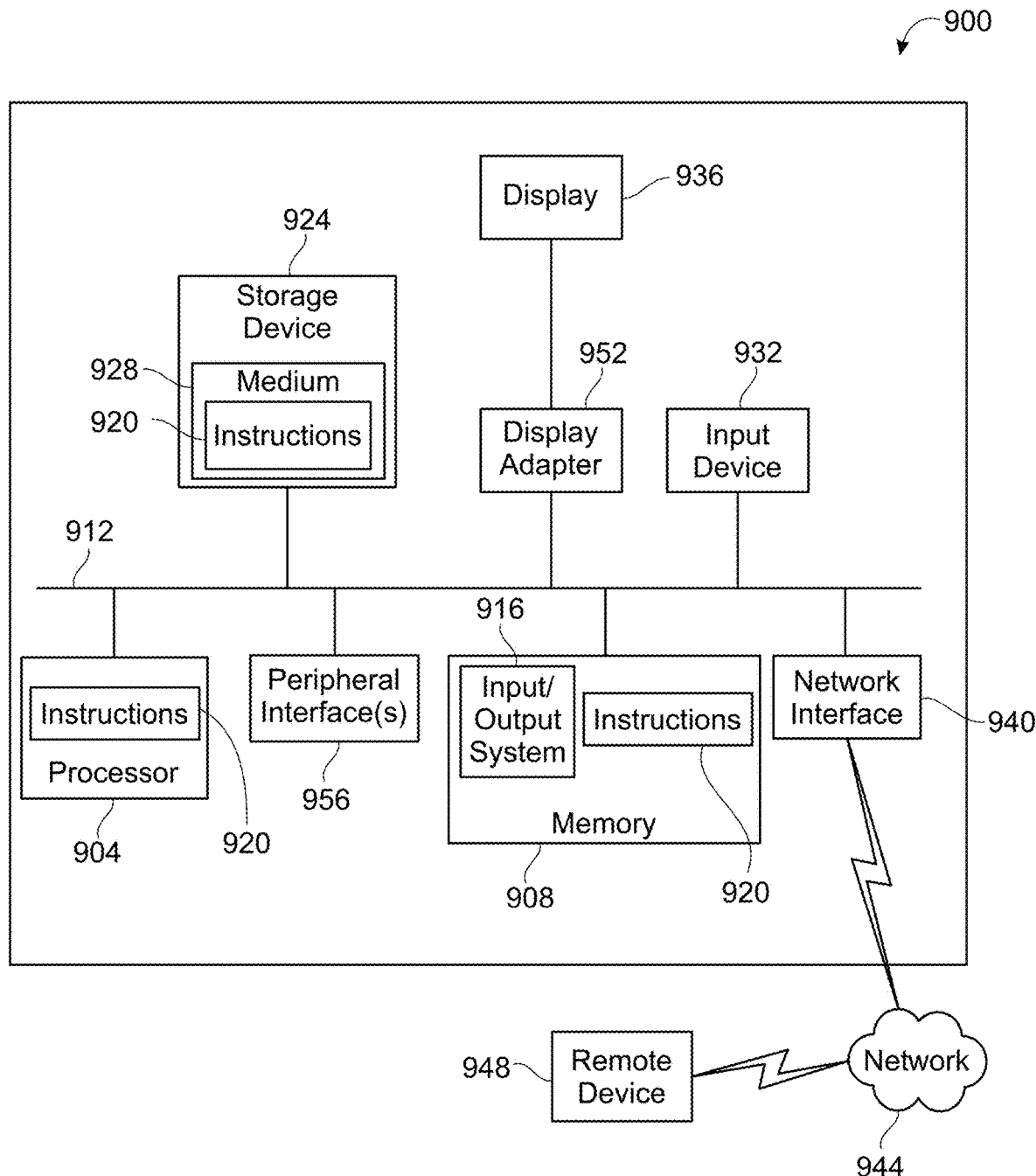
FIG. 9 illustrates a block diagram of testing performed using bisected human molars having a ground flat facet, in accordance with at least one embodiment.

FIG. 9 illustrates a block diagram of a testing performed using bisected human molars 900 having a ground flat facet, in accordance with at least one embodiment. Each flat facet was masked with copper tape so that only a treated half 910 of the flat facet was exposed to the laser treatment. The untreated half 912 beneath the copper tape was left untreated. The facet was then treated with the laser scan pattern at a prescribed pulse duration and 1 W average power. During the treatment of the facet, a smear layer was removed, as evidenced by smoke (i.e., particles and vapors) visibly emanating from the surface. Likewise, overtreatment of the facet, onto the unground surface of the tooth, showed similar smoke during initial treatment which dissipated after the first laser irradiation. This smoke is believed to have been a result of the removal of a biofilm layer (e.g., pellicle, calculur, and/or tartar) on the unground portion of the tooth. After laser treatment, the copper tape was removed and tape residue was removed with acetone and a cotton swab. Next, a thin stripe of nail polish 914 was applied to the flat facet. The nail polish stripe was applied perpendicularly to the direction the copper tape was applied. So, the nail polish 914 covered and left exposed two areas of the facet, which comprised laser treated 910 and untreated 912 areas. The samples were then exposed to acid erosive challenges of varying durations. Acid erosive challenge parameters included a citric acid buffer, 3.2 pH, and 35° C. temperature. After the erosive challenge, the nail polish was removed with acetone and each tooth was examined with a confocal microscope (Lieca DCM8). Depth of erosion (relative to the nail polish-masked surface, which was not exposed to the acid) was determined for both laser-treated and untreated surfaces and compared to reveal a percent reduction in erosion. In some cases, before the erosive challenge, the tooth surface was analyzed using an FTIR spectrometer (Nicolet Summit with an IRSurvey micro sampler attachment). An FTIR spectrum of laser-treated and untreated surfaces of the bisected molar facet was compared to determine the percent carbonate reduction resulting from treatment. Finally, the surfaces of the teeth were examined under a high-powered microscope to ensure that overheating of the tooth surface (i.e., melting) did not occur, even at a microscopic level. A number of laser parameters were tested. Representative laser parameters are shown in the table below.

| Sample (—) | Pulse Duration (uS) | Power (W) | Rep. Rate (Hz) | Pulse Energy (mJ) | Avg. Fluence (J/cm$^2$) | Peak Fluence (J/cm$^2$) | FTIR (Y/N) | Erosion (min) |
|---|---|---|---|---|---|---|---|---|
| 1 |  |  |  | 2.5 | 0.74 | 1.48 | Yes | 10 |
| 2 | 16.5 | 1.04 | 481 | 2.16 | 0.64 | 1.28 | Yes | 10 |
| 3 | 16.8 | 1.05 | 448 | 2.34 | 0.69 | 1.39 | No | 5 |
| 4 | 17.4 | 1.05 | 417 | 2.52 | 0.74 | 1.49 | No | 15 |
| 5 | 16.7 | 1.03 | 481 | 2.14 | 0.63 | 1.27 | No | 5 |
| 6 | 17.3 | 1.05 | 419 | 2.51 | 0.74 | 1.48 | No | 15 |

Results—Laser treatment with the exemplary embodiment was able to achieve both carbonate reduction and acid erosion resistance in human enamel. For example, 50% or more carbonate reduction correlated with a marked increase in acid demineralization resistance (e.g., 80%). It was found that most laser settings were able to achieve at least 50% carbonate reduction without introducing surface overheating. Also, some laser parameters could effectively remove all the carbonate from the surface of the tooth without surface damage.

Figure 10:
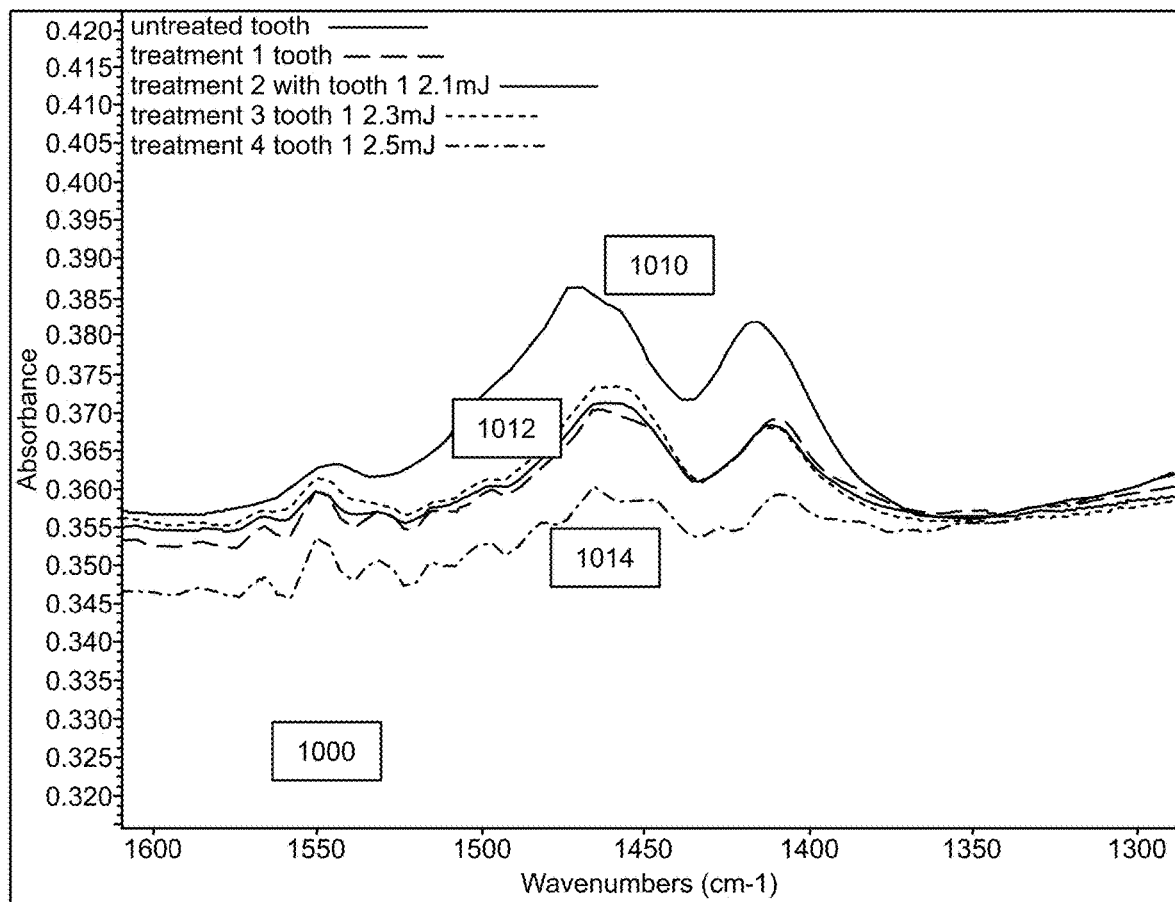
FIG. 10 illustrates a graphical representation of FTIR spectra measured from teeth pre-treatment and post-treatment, in accordance with at least one embodiment.

FIG. 10 illustrates a graphical representation of FTIR spectra 1000 measured from teeth pre-treatment 1010 and post-treatment 1012, 1014, in accordance with at least one embodiment. It can be seen that about 50% carbonate reduction 1012 corresponds with pulse energies of about 1.9-2.3 mJ (Avg. fluence between 0.5-0.7 J/cm$^2$), while complete carbonate removal is achieved with pulse energies of 2.5 mJ (Avg. fluence >0.7 J/cm$^2$). Additionally, confocal microscope profilometry revealed reduced erosion with the laser-treated surfaces.

Figure 11:
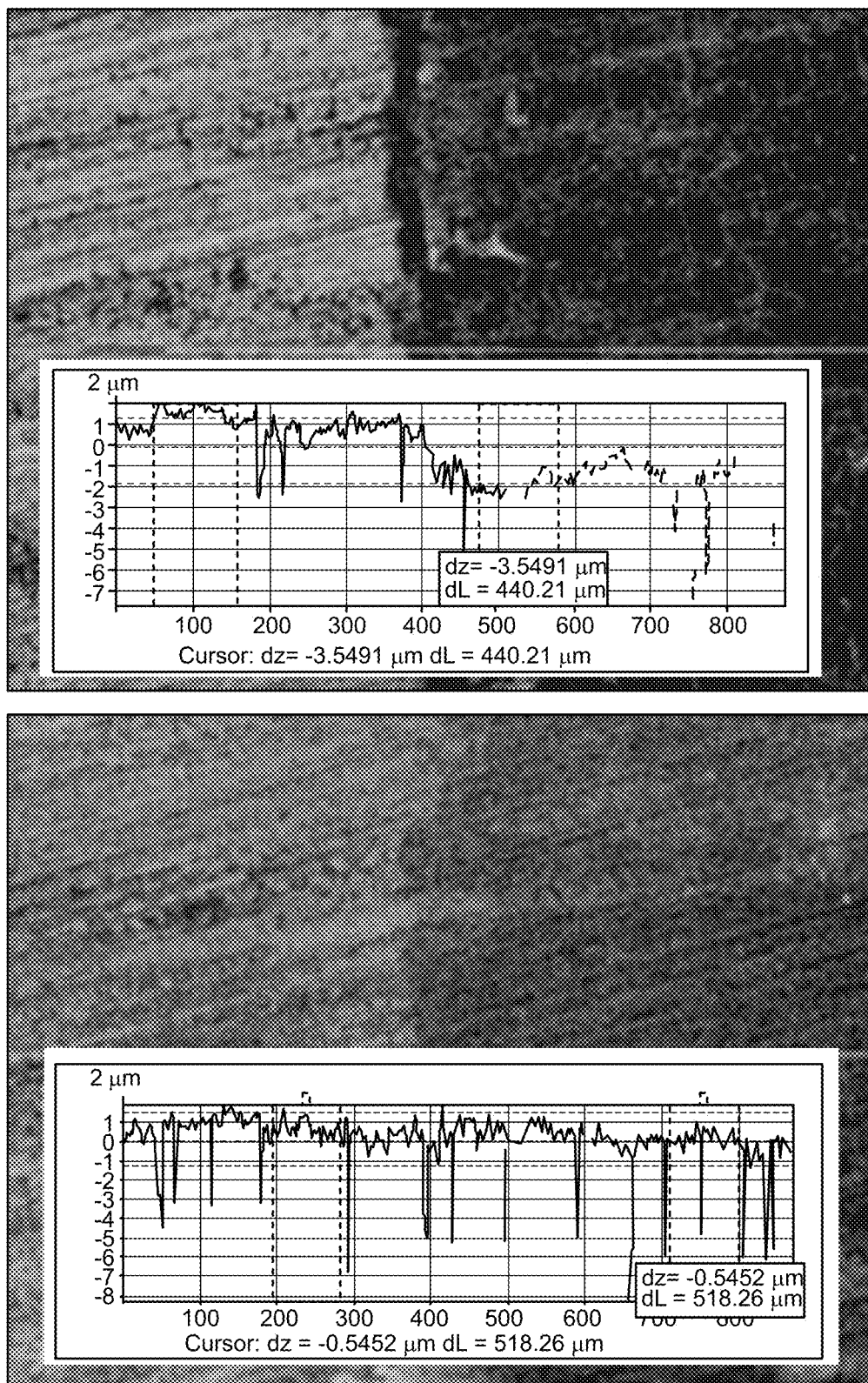
FIG. 11 illustrates representative confocal measurements showing a sample experienced 3.5 µm of erosion in an untreated portion of the tooth and only 0.5 µm of erosion where the tooth had been laser treated, in accordance with at least one embodiment.

FIG. 11 illustrates representative confocal measurements showing a sample experienced 3.5 μm of erosion in an untreated portion of the tooth and only 0.5 μm of erosion where the tooth had been laser treated. This corresponds to an 86% reduction in erosion for the laser-treated surface compared to the untreated surface.

Figure 12:
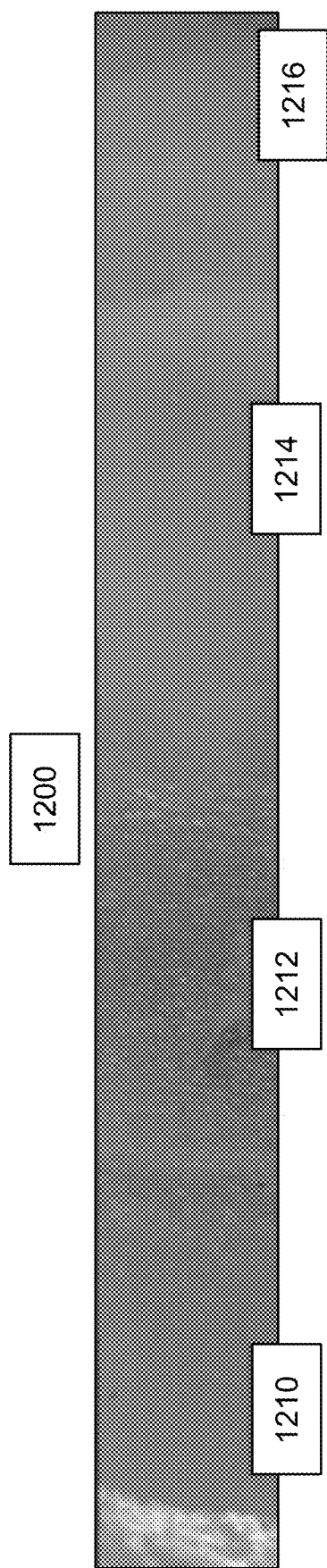
FIG. 12 illustrates a stitched composite microscopic image of a ground flat facet of a human molar having four vertical stripes treated with: 0.6 $J/cm^2$ fluence (no surface damage), 0.9 $J/cm^2$ (melting), untreated, and 0.7 $J/cm^2$ (no surface damage), in accordance with at least one embodiment.

FIG. 12 shows a stitched composite microscopic image 1200 of a ground flat facet of a human molar having four vertical stripes treated with: 0.6 J/cm$^2$ fluence (no surface damage) 1210, 0.9 J/cm$^2$ (melting) 1212, untreated 1214, and 0.7 J/cm$^2$ (no surface damage) 1216. It was found, with the exemplary embodiment, that fluences of about 0.9 J/cm$^2$ cause melting of the surface, which is seen only under a microscope. However, fluence settings used for treatment (even those capable of removing all of the carbonates from the surface) can be delivered to the teeth without causing melting.

Conclusion—The exemplary embodiment was able to produce an effective treatment at a speed suitable for the clinic, without damaging the surface of the teeth. Using the 9.3 μm laser, an average fluence setting between 0.5 and 0.75 J/cm$^2$ removes carbonate, increases acid resistance, and does not damage the tooth surface. With this bench test, it was demonstrated that treatment can be performed quickly, using a large (e.g., 2.5 mm wide) scanned laser pattern, and that this pattern can be arranged to prevent overtreatment (and overheating of the surface). Additionally, this treatment was demonstrated to be effective using both acid erosive tests and FTIR spectral analysis.

The methods, systems, and devices discussed above are examples. Various configurations may omit, substitute, or add various procedures or components as appropriate. For instance, in alternative configurations, the methods may be performed in an order different from that described, and that various steps may be added, omitted, or combined. For example, in some embodiments, fluoride treatment is omitted after laser treatment. Also, features described with respect to certain configurations may be combined in various other configurations. Different aspects and elements of the configurations may be combined similarly. Technology evolves and, thus, many of the elements are examples and do not limit the scope of the disclosure or claims.

Figure 13:
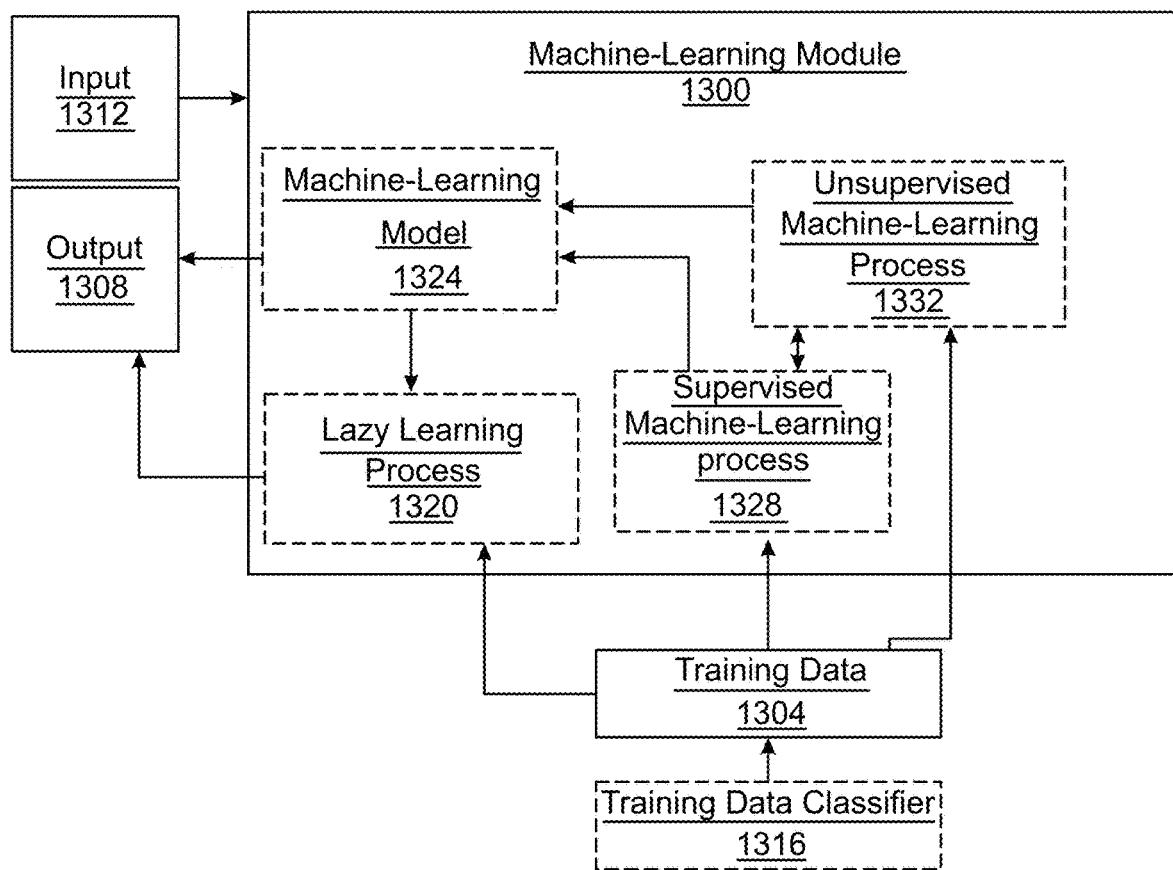
FIG. 13 illustrates a block diagram of exemplary machine-learning processes, in accordance with at least one embodiment.

FIG. 13 illustrates a block diagram of exemplary machine learning processes, in accordance with at least one embodiment. The machine-learning module 1300 shown in FIG. 13 may perform one or more machine-learning processes as described in this disclosure. Machine-learning module 1300 may perform determinations, classification, and/or analysis steps, methods, processes, or the like as described in this disclosure using machine-learning processes. A "machine learning process," as used in this disclosure, is a process that automatedly uses training data 1304 to generate an algorithm that will be performed by a computing device/module to produce outputs 1308 given data provided as inputs 1312; this is in contrast to a non-machine learning software program where the commands to be executed are determined in advance by a user and written in a programming language. Inputs and outputs may include any parameters described in this disclosure.

Still referring to FIG. 13, "training data," as used herein, is data containing correlations that a machine-learning process may use to model relationships between two or more categories of data elements. For instance, and without limitation, training data 1304 may include a plurality of data entries, each entry representing a set of data elements that were recorded, received, and/or generated together; data elements may be correlated by shared existence in a given data entry, by proximity in a given data entry, or the like. Multiple data entries in training data 1304 may evince one or more trends in correlations between categories of data elements; for instance, and without limitation, a higher value of a first data element belonging to a first category of a data element may tend to correlate to a higher value of a second data element belonging to a second category of data element, indicating a possible proportional or other mathematical relationship linking values belonging to the two categories. Multiple categories of data elements may be related in training data 1304 according to various correlations; correlations may indicate causative and/or predictive links between categories of data elements, which may be modeled as relationships such as mathematical relationships by machine-learning processes as described in further detail below. Training data 1304 may be formatted and/or organized by categories of data elements, for instance by associating data elements with one or more descriptors corresponding to categories of data elements. As a non-limiting example, training data 1304 may include data entered in standardized forms by persons or processes, such that the entry of a given data element in a given field in a form may be mapped to one or more descriptors of categories. Elements in training data 1304 may be linked to descriptors of categories by tags, tokens, or other data elements; for instance, and without limitation, training data 1304 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively, or additionally, and continuing to refer to FIG. 13, training data 1304 may include one or more elements that are not categorized; that is, training data 1304 may not be formatted or contain descriptors for some elements of data. Machine-learning algorithms and/or other processes may sort training data 1304 according to one or more categorizations using, for instance, natural language processing algorithms, tokenization, detection of correlated values in raw data, and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or another compendium of terms, permitting ad-hoc categorization by machine-learning algorithms, and/or automated association of data in the data entry with descriptors or into a given format. The ability to categorize data entries automatedly may enable the same training data 1304 to be made applicable for two or more distinct machine-learning algorithms as described in further detail below. Training data 1304 used by machine-learning module 1300 may correlate any input data as described in this disclosure to any output data as described in this disclosure.

Further referring to FIG. 13, training data may be filtered, sorted, and/or selected using one or more supervised and/or unsupervised machine-learning processes and/or models as described in further detail below; such models may include without limitation training data classifier 1316. Training data classifier 1316 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 1300 may generate a classifier using a classification algorithm, defined as a process whereby a computing device and/or any module and/or component operating thereon derives a classifier from training data 1304. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. Classifiers may be used to classify any parameters described herein.

Still referring to FIG. 13, machine-learning module 1300 may be configured to perform a lazy-learning process 1320 and/or protocol, which may alternatively be referred to as a "lazy loading" or "call-when-needed" process and/or protocol, maybe a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 1304. Heuristics may include selecting some number of highest-ranking associations and/or training data 1304 elements. Lazy learning may implement any suitable lazy learning algorithm, including without limitation a K-nearest neighbors' algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively, or additionally, and with continued reference to FIG. 13, machine-learning processes as described in this disclosure may be used to generate machine-learning models 1324. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 1324 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 1324 may be generated by creating an artificial neural network, such as a convolutional neural network comprising an input layer of nodes, one or more intermediate layers, and an output layer of nodes. Connections between nodes may be created via the process of "training" the network, in which elements from a training data 1304 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 13, machine-learning algorithms may include at least a supervised machine-learning process 1328. At least a supervised machine-learning process 1328, as defined herein, include algorithms that receive a training set relating a number of inputs to a number of outputs and seek to find one or more mathematical relations relating inputs to outputs, where each of the one or more mathematical relations is optimal according to some criterion specified to the algorithm using some scoring function. For instance, a supervised learning algorithm may include dental parameters as described above as inputs, diagnosis as outputs, and a scoring function representing a desired form of relationship to be detected between inputs and outputs; the scoring function may, for instance, seek to maximize the probability that a given input and/or combination of elements inputs is associated with a given output to minimize the probability that a given input is not associated with a given output. The scoring function may be expressed as a risk function representing an "expected loss" of an algorithm relating inputs to outputs, where loss is computed as an error function representing a degree to which a prediction generated by the relation is incorrect when compared to a given input-output pair provided in training data 1304. Persons skilled in the art, upon reviewing the entirety of this disclosure, will be aware of various possible variations of at least a supervised machine-learning process 1328 that may be used to determine the relation between inputs and outputs. Supervised machine-learning processes may include classification algorithms as defined above.

Further referring to FIG. 13, machine-learning processes may include at least unsupervised machine-learning processes 1332. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 13, machine-learning module 1300 may be designed and configured to create a machine-learning model 1324 using techniques for the development of linear regression models. Linear regression models may include ordinary least squares regression, which aims to minimize the square of the difference between predicted outcomes and actual outcomes according to an appropriate norm for measuring such a difference (e.g., a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include the least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive-aggressive algorithm, a robustness regression model, a Huber regression model, or any other suitable model that may occur to persons skilled in the art upon reviewing the entirety of this disclosure. Linear regression models may be generalized in an embodiment of polynomial regression models, whereby a polynomial equation (e.g. a quadratic, cubic, or higher-order equation) providing a best-predicted output/actual output fit is sought; similar methods to those described above may be applied to minimize error functions, as will be apparent to persons skilled in the art upon reviewing the entirety of this disclosure.

Continuing to refer to FIG. 13, machine-learning algorithms may include, without limitation, linear discriminant analysis. Machine-learning algorithms may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in software art. Aspects and implementations discussed above employing software and/or software modules may also include appropriate hardware for assisting in the implementation of the machine-executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 14:
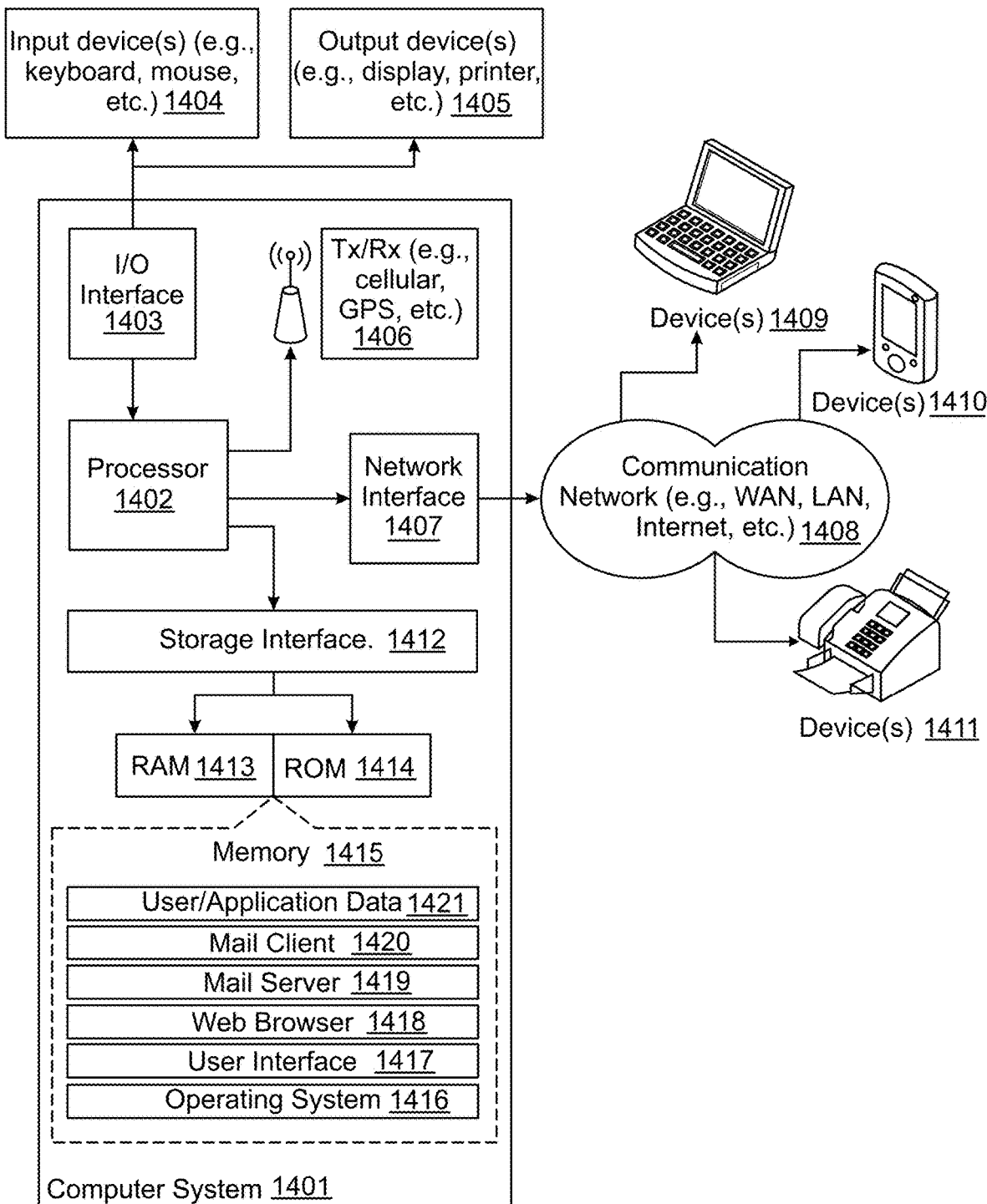
FIG. 14 illustrates a block diagram of an exemplary computer system for implementing embodiments consistent with the present disclosure.

FIG. 14 illustrates a block diagram of an exemplary computer system for implementing embodiments consistent with the present disclosure. Variations of computer system 1401 may be used for performing optical character recognition on an image including a plurality of printed characters. The computer system 1401 may comprise a central processing unit ("CPU" or "processor") 1402. Processor 1402 may comprise at least one data processor for executing program components for executing user- or system-generated requests. A user may include a person, a person using a device such as those included in this disclosure, or such a device itself. The processor may include specialized processing units such as integrated system (bus) controllers, memory management control units, floating-point units, graphics processing units, digital signal processing units, etc. The processor may include a microprocessor, such as AMD Athlon, Duron, or Opteron, ARM's application, embedded or secure processors, IBM PowerPC, Intel's Core, Itanium, Xeon, Celeron or other lines of processors, etc. Processor 1402 may be implemented using a mainframe, distributed processor, multi-core, parallel, grid, or other architectures. Some embodiments may utilize embedded technologies like application-specific integrated circuits (ASICs), digital signal processors (DSPs), Field Programmable Gate Arrays (FPGAs), etc.

Processor 1402 may be disposed in communication with one or more input/output (I/O) devices via I/O interface 1403. The I/O interface 1403 may employ communication protocols/methods such as, without limitation, audio, analog, digital, monoaural, RCA, stereo, IEEE-1394, serial bus, universal serial bus (USB), infrared, PS/2, BNC, coaxial, component, composite, digital visual interface (DVI), high-definition multimedia interface (HDMI), RF antennas, S-Video, VGA, IEEE 802.n/b/g/n/x, Bluetooth, cellular (e.g., code-division multiple access (CDMA), high-speed packet access (HSPA+), global system for mobile communications (GSM), long-term evolution (LTE), WiMax, or the like), etc.

Using the I/O interface 1403, the computer system 1401 may communicate with one or more I/O devices. For example, the input device 404 may be an antenna, keyboard, mouse, joystick, (infrared) remote control, camera, card reader, fax machine, dongle, biometric reader, microphone, touch screen, touchpad, trackball, sensor (e.g., accelerometer, light sensor, GPS, gyroscope, proximity sensor, or the like), stylus, scanner, storage device, transceiver, video device/source, visors, etc. Output device 405 may be a printer, fax machine, video display (e.g., cathode ray tube (CRT), liquid crystal display (LCD), light-emitting diode (LED), plasma, or the like), audio speaker, etc. In some embodiments, a transceiver 1406 may be disposed in connection with the processor 1402. The transceiver may facilitate various types of wireless transmission or reception. For example, the transceiver may include an antenna operatively connected to a transceiver chip (e.g., Texas Instruments WiLink WL1283, Broadcom BCM4750IUB8, Infineon Technologies X-Gold 618-PMB9800, or the like), providing IEEE 802.11a/b/g/n, Bluetooth, FM, a global positioning system (GPS), 2G/3G HSDPA/HSUPA communications, etc.

In some embodiments, the processor 1402 may be disposed in communication with a communication network 1408 via a network interface 1407. The network interface 1407 may communicate with the communication network 1408. The network interface may employ connection protocols including, without limitation, direct connect, Ethernet (e.g., twisted pair 10/100/1000 Base T), transmission control protocol/internet protocol (TCP/IP), token ring, IEEE 802.11a/b/g/n/x, etc. The communication network 1408 may include, without limitation, a direct interconnection, local area network (LAN), wide area network (WAN), wireless network (e.g., using Wireless Application Protocol), the Internet, etc. Using the network interface 407 and the communication network 408, the computer system 1401 may communicate with devices 1410, 1411, and 1412. These devices may include, without limitation, personal computer(s), server(s), fax machines, printers, scanners, various mobile devices such as cellular telephones, smartphones (e.g., Apple iPhone, Blackberry, Android-based phones, etc.), tablet computers, eBook readers (Amazon Kindle, Nook, etc.), laptop computers, notebooks, gaming consoles (Microsoft Xbox, Nintendo DS, Sony PlayStation, etc.), or the like. In some embodiments, the computer system 1401 may itself embody one or more of these devices.

In some embodiments, the processor 1402 may be disposed of in communication with one or more memory devices (e.g., RAM 413, ROM 414, etc.) via a storage interface 1412. The storage interface may connect to memory devices including, without limitation, memory drives, removable disc drives, etc., employing connection protocols such as serial advanced technology attachment (SATA), integrated drive electronics (IDE), IEEE-1394, universal serial bus (USB), fiber channel, small computer systems interface (SCSI), etc. The memory drives may further include a drum, magnetic disc drive, magneto-optical drive, optical drive, redundant array of independent disks (RAID), solid-state memory devices, solid-state drives, etc.

The memory devices may store a collection of program or database components, including, without limitation, an operating system 1416, the user interface application 1417, web browser 1418, mail server 1419, mail client 1420, user/application data 1421 (e.g., any data variables or data records discussed in this disclosure), etc. The operating system 1416 may facilitate resource management and operation of the computer system 1401. Examples of operating systems include, without limitation, Apple Macintosh OS X, UNIX, Unix-like system distributions (e.g., Berkeley Software Distribution (BSD), FreeBSD, NetBSD, OpenBSD, etc.), Linux distributions (e.g., Red Hat, Ubuntu, Kubuntu, etc.), IBM OS/2, Microsoft Windows (XP, Vista/7/8, etc.), Apple iOS, Google Android, Blackberry OS, or the like. User interface 1417 may facilitate the display, execution, interaction, manipulation, or operation of program components through textual or graphical facilities. For example, user interfaces may provide computer interaction interface elements on a display system operatively connected to the computer system 1401, such as cursors, icons, checkboxes, menus, scrollers, windows, widgets, etc. Graphical user interfaces (GUIs) may be employed, including, without limitation, Apple Macintosh operating systems' Aqua, IBM OS/2, Microsoft Windows (e.g., Aero, Metro, etc.), Unix X-Windows, web interface libraries (e.g., ActiveX, Java, Javascript, AJAX, HTML, Adobe Flash, etc.), or the like.

In some embodiments, the computer system 1401 may implement a web browser 1418 stored program component. The web browser may be a hypertext viewing application, such as Microsoft Internet Explorer, Google Chrome, Mozilla Firefox, Apple Safari, etc. Secure web browsing may be provided using HTTPS (secure hypertext transport protocol), secure sockets layer (SSL), Transport Layer Security (TLS), etc. Web browsers may utilize facilities such as AJAX, DHTML, Adobe Flash, JavaScript, Java, application programming interfaces (APIs), etc. In some embodiments, the computer system 1401 may implement a mail server 1419 stored program component. The mail server may be an Internet mail server such as Microsoft Exchange, or the like. The mail server may utilize facilities such as ASP, ActiveX, ANSI C++/C #, Microsoft .NET, CGI scripts, Java, JavaScript, PERL, PHP, Python, WebObjects, etc. The mail server may utilize communication protocols such as internet message access protocol (IMAP), messaging application programming interface (MAPI), Microsoft Exchange, post office protocol (POP), simple mail transfer protocol (SMTP), or the like. In some embodiments, the computer system 1401 may implement a mail client 1420 stored program component. The mail client may be a mail-viewing application, such as Apple Mail, Microsoft Entourage, Microsoft Outlook, Mozilla Thunderbird, etc.

In some embodiments, computer system 1401 may store user/application data 1421, such as the data, variables, records, etc. as described in this disclosure. Such databases may be implemented as fault-tolerant, relational, scalable, secure databases such as Oracle or Sybase. Alternatively, such databases may be implemented using standardized data structures, such as an array, hash, linked list, struct, structured text file (e.g., XML), table, or as object-oriented databases (e.g., using ObjectStore, Poet, Zope, etc.). Such databases may be consolidated or distributed, sometimes among the various computer systems discussed above in this disclosure. It is to be understood that the structure and operation of any computer or database component may be combined, consolidated, or distributed in any working combination.

Furthermore, one or more computer-readable storage media may be utilized in implementing embodiments consistent with the present invention. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., non-transitory. Examples include Random Access Memory (RAM), Read-Only Memory (ROM), volatile memory, nonvolatile memory, hard drives, Compact Disc (CD) ROMs, Digital Video Disc (DVDs), flash drives, disks, and any other known physical storage media.

Figure 15:
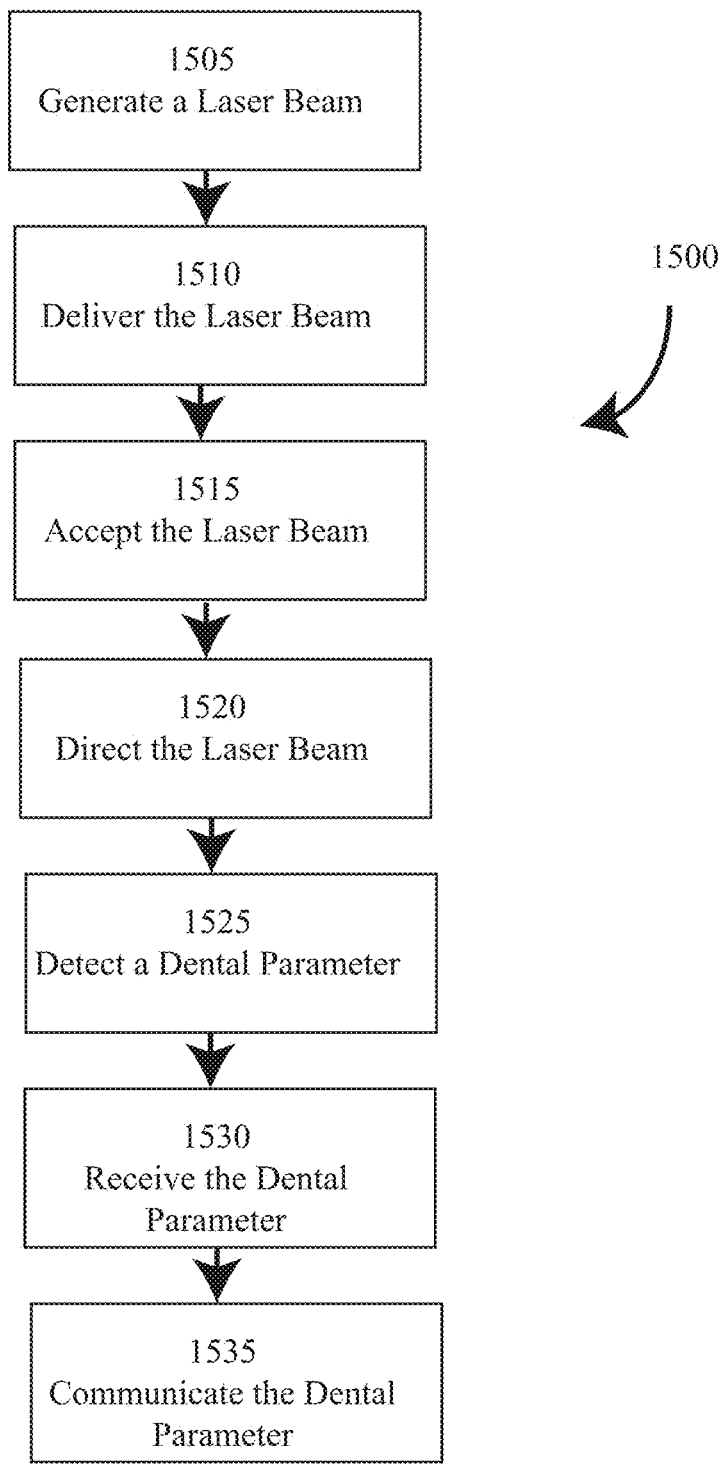
FIG. 15 illustrates a method of dental treatment and remote oversight with a flow diagram, according to some embodiments.

Referring now to FIG. 15, a method 1500 of dental treatment and remote oversight is illustrated with a flow diagram, according to some embodiments. In some embodiments, the method 1500 may include, at step 1505, generating, using a laser configured, a laser beam as a function of a laser parameter. The method 1500 may include, at step 1510, delivering, using a beam delivery system, the laser beam from the laser. The method 1500 may include, at step 1515, accepting, using a hand piece, the laser beam from the beam delivery system. The method 1500 may include, at step 1520, directing, using the hand piece, the laser beam to dental tissue. The method may include, at step 1525, detecting, using a sensor, a dental parameter as a function of a dental phenomenon. The method 1500 may include, at step 1530, receiving, using a computing device, the dental parameter from the sensor. Finally, the method 1500 may include, at step 1535, communicating, using the computing device, the dental parameter to a remote device configured to interface with a remote user.

Still referring to FIG. 15, in some cases, sensor may comprise a camera and dental parameter comprises an image of oral tissue. In some cases, camera may be located proximal to hand piece, and method 1500 may further include facilitating, using the hand piece, an optical path between the oral tissue and the camera. In some cases, optical path may include a zinc selenide lens. In some cases, camera may have a global shutter.

Still referring to FIG. 15, in some embodiments, method 1500 may additionally include scanning, using a beam scanner of the beam delivery system, to scan the laser beam as a function of a scan parameter and controlling, using the computing device, the scan parameter.

Still referring to FIG. 15, in some embodiments, method 1500 may additionally include controlling, using computing device, the laser parameter. In some embodiments, remote device is configured to communicate with a user of the system. In some embodiments, sensor detects the dental parameter concurrently while the laser generates the laser beam. In some cases, computing device communicates the dental parameter to the remote device concurrently while the laser generates the laser beam.

Figure 16:
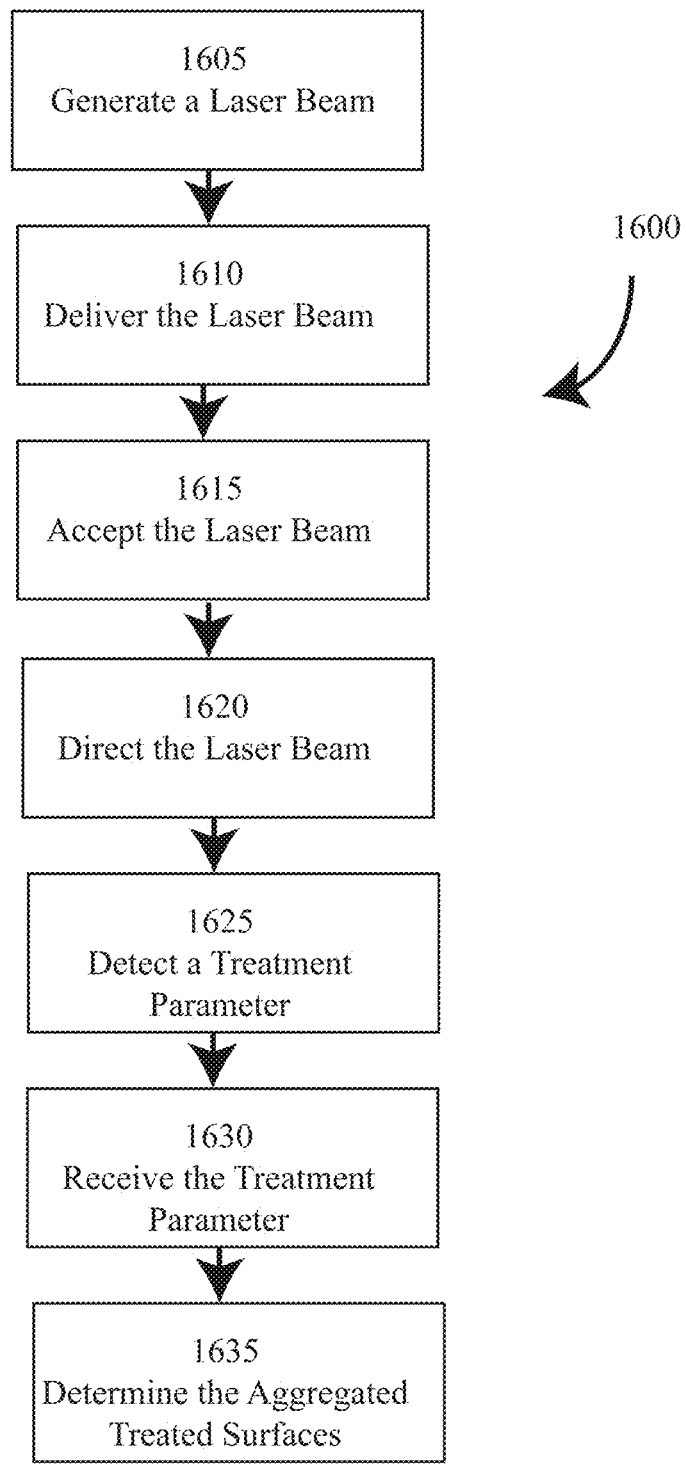
FIG. 16 illustrates a method of dental treatment and verification by way of a flow diagram, according to some embodiments.

Referring now to FIG. 16, a method 1600 of dental treatment and verification is illustrated by way of a flow diagram, according to some embodiments. At step 1605, method 1600 may include generating, using a laser, a laser beam as a function of a laser parameter. At step 1610, method 1600 may include delivering, using a beam delivery system, the laser beam from the laser. At step 1615, method 1600 may include accepting, using a hand piece, the laser beam from the beam delivery system. At step 1620, method 1600 may include directing, using the hand piece, the laser beam to dental tissue. At step 1625, method 1600 may include detecting, using a sensor, a treatment parameter as a function of a treatment phenomenon. At step 1630, method 1600 may include receiving, using a computing device, the treatment parameter from the sensor. Finally, at step 1635, method may include determining, using the computing device, aggregated treated surfaces as a function of the treatment parameter.

Still referring to FIG. 16, in some embodiments, sensor may include a position sensor and the treatment parameter represents a treated location. In some cases, method 1600 may additionally include generating, using the computing device, a three-dimensional representation of the treated location.

Still referring to FIG. 16, in some embodiments, treatment parameter comprises an image of a restorative procedure. In some cases, method 1600 may additionally include charting, using the computing device, the restorative procedure.

Still referring to FIG. 16, in some embodiments, method 1600 may additionally include generating, using the computing device, a treatment metric as a function of one or more of the treatment parameter and the aggregated treated surfaces and communicating, using the computing device, the treatment metric to a remote device. In some cases, generating the treatment metric includes inputting one or more of the treatment parameter and a representation of the aggregated treated surfaces into a treatment metric machine learning model and outputting the treatment metric as a function of the treatment metric machine learning model and one or more of the treatment parameter and the representation of the aggregated treated surfaces. In some cases, generating the treatment metric further includes training the treatment metric machine learning model by: inputting a treatment metric training set into a machine learning algorithm, wherein the treatment metric training set correlates treatment metrics to one or more of the treatment parameter and the representation of the aggregated treated surfaces and training the treatment metric machine learning model as a function of the treatment metric training set and the machine learning algorithm. In some cases, treatment metric is related to a treatment including one or more of cleaning, purifying, whitening, and alignment.

Figure 17:
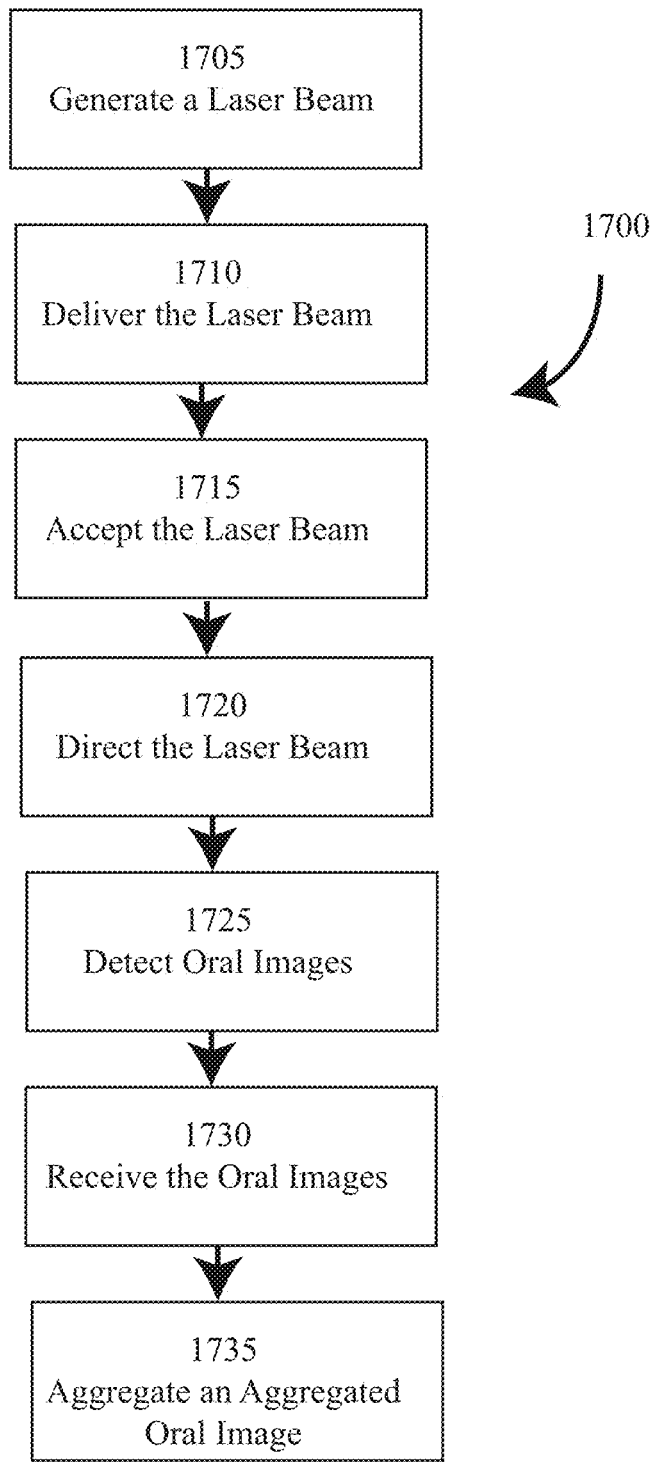
FIG. 17 illustrates a method of generating an image representative of oral tissue concurrently with preventative dental laser treatment by way of a flow diagram, according to some embodiments.

Referring now to FIG. 17, a method 1700 of generating an image representative of oral tissue concurrently with preventative dental laser treatment is illustrated by way of a flow diagram, according to some embodiments. At step 1705, method 1700 may include generating, using a laser, a laser beam as a function of a laser parameter. At step 1710, method 1700 may include delivering, using a beam delivery system, the laser beam from the laser. At step 1715, method 1700 may include accepting, using a hand piece, the laser beam from the beam delivery system. At step 1720, method 1700 may include directing, using the hand piece, the laser beam to dental tissue, wherein the laser beam performs a non-ablative treatment of the dental tissue, as a function of the laser parameter. At step 1725, method 1700 may include detecting, using a sensor, a plurality of oral images as a function of oral phenomena concurrently with delivery of the laser beam to the dental tissue. At step 1730, method 1700 may include receiving, using a computing device, the plurality of oral images from the sensor. At step 1735, method 1700 may include aggregating, using the computing device, an aggregated oral image as a function of the plurality of oral images.

Still referring to FIG. 17, in some embodiments, aggregated oral image may include a three-dimensional representation of oral tissue. In some cases, method 1700 may additionally include associating, using the computing device, the aggregated oral image with the laser parameter.

Still referring to FIG. 17, in some embodiments, aggregating the aggregated oral image further may include identifying at least a common feature in a first oral image and a second oral image of the plurality of oral images and transforming one or more of the first oral image and the second oral image as a function of the at least a common feature. In some cases, aggregating the aggregated oral image further comprises blending a demarcation between the first oral image and the second oral image. In some cases, blending the demarcation may include comparing pixel values between overlapping pixels in the first oral image and the second oral image and altering the demarcation as a function of the comparison. In some cases, altering the demarcation comprises minimizing a difference in value between overlapping pixels between the first oral image and the second oral image along the demarcation.

Still referring to FIG. 17, in some embodiments, aggregated oral image has a resolution which is finer than one or more of 500, 250, 150, 100, 50, or 25 micrometers. In some embodiments, aggregating the aggregated oral image may include inputting the plurality of oral images into an image aggregation machine learning model and outputting the aggregated oral image as a function of the plurality of oral images and the image aggregation machine learning model. In some cases, aggregating the aggregated oral image may additionally include training the image aggregation machine learning model by inputting an image aggregation training set into a machine learning process, wherein the image aggregation training set correlates aggregated oral images to pluralities of oral images and training the image aggregation metric machine learning model as a function of the image aggregation training set and the machine learning algorithm.

Figure 18:
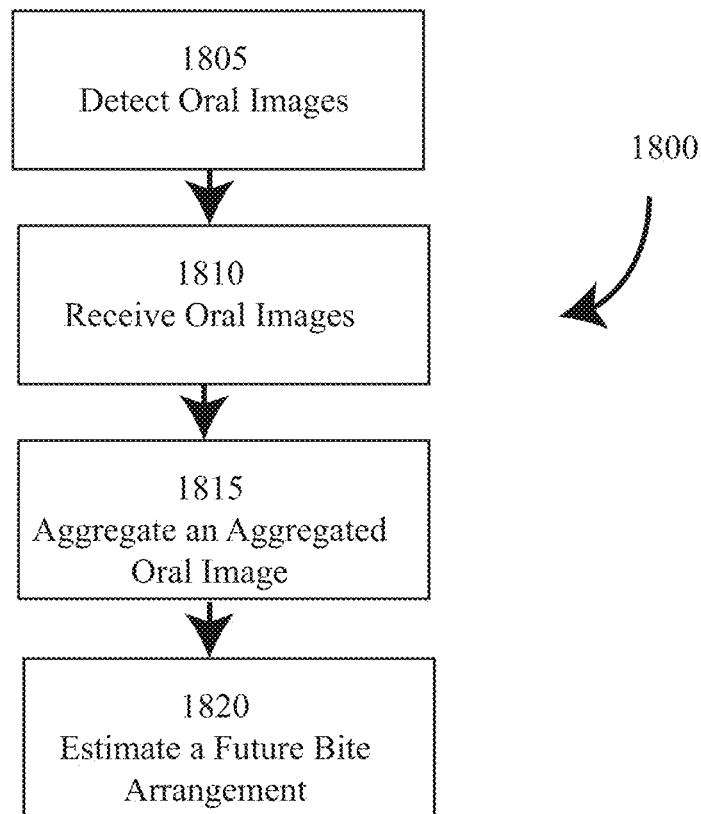
FIG. 18, illustrates a method of estimating future bite arrangement by way of a flow diagram, according to some embodiments.

Referring now to FIG. 18, a method 1800 of estimating future bite arrangement is illustrated by way of a flow diagram, according to some embodiments. At step 1805, method 1800 may include detecting, using a sensor, a plurality of oral images as a function of oral phenomena. At step 1810, method 1800 may include receiving, using a computing device, the plurality of oral images from the sensor. At step 1815, method 1800 may include aggregating, using the computing device, an aggregated oral image as a function of the plurality of oral images. At step 1820, method 1800 may include estimating, using the computing device, a future bite arrangement as a function of the aggregated oral image.

Still referring to FIG. 18, in some embodiments, aggregated oral image may include a three-dimensional representation of oral tissue. In some embodiments, aggregating the aggregated oral image may additionally include identifying at least a common feature in a first oral image and a second oral image of the plurality of oral images and transforming one or more of the first oral image and the second oral image as a function of the at least a common feature. In some cases, aggregating the aggregated oral image further comprises blending a demarcation between the first oral image and the second oral image. In some cases, blending the demarcation may include comparing pixel values between overlapping pixels in the first oral image and the second oral image and altering the demarcation as a function of the comparison. In some cases, altering the demarcation comprises minimizing a difference in value between overlapping pixels between the first oral image and the second oral image along the demarcation. In some cases, estimating the future bite arrangement may include inputting the aggregated oral image to a bite estimation machine learning model and estimating the future bite arrangement using the bite estimation machine learning model. In some cases, estimating the future bite arrangement may additionally include inputting bite estimation training data into a machine learning processes, wherein the bite estimation training data correlates oral images to subsequent bite arrangements and training the bite estimation machine learning model, using the bite estimation training data. In some cases, estimating the future bite arrangement may additionally include classifying the aggregated oral image and selecting the bite estimation training data from a plurality of training data as a function of the classification of the aggregated oral image. In some cases, classifying the aggregated oral image is performed as a function of patient information.

Figure 19:
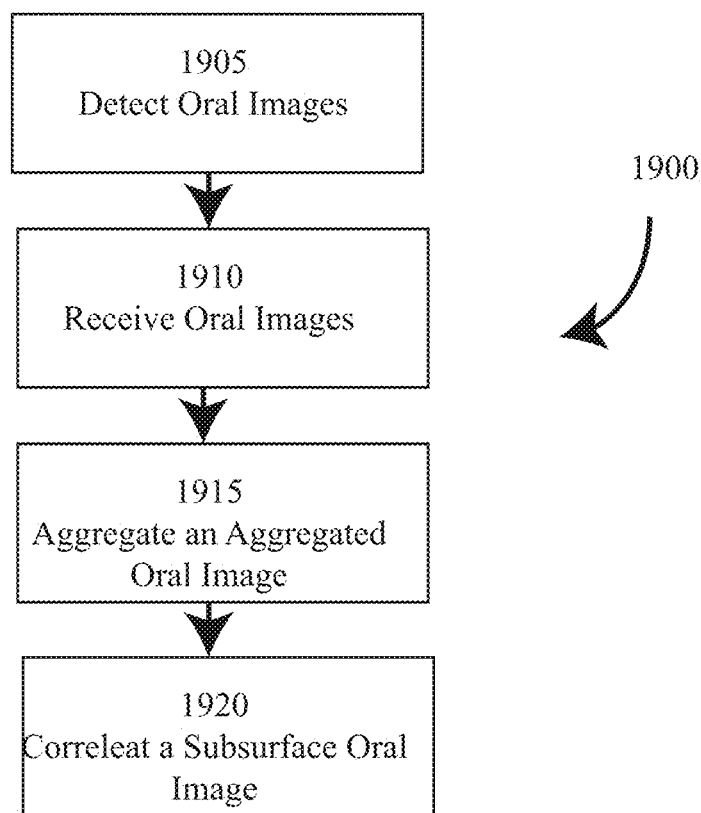
FIG. 19 illustrates a method for correlating surface and subsurface oral imagery by way of a flow diagram, according to some embodiments.

Referring now to FIG. 19, a method 1900 for correlating surface and subsurface oral imagery is illustrated by way of a flow diagram, according to some embodiments. At step 1905, method 1900 may include detecting, using a sensor, a plurality of oral images as a function of oral phenomena. At step 1910, method 1900 may include receiving, using a computing device, the plurality of oral images from the sensor. At step 1915, method 1900 may include aggregating, using the computing device, an aggregated oral image as a function of the plurality of oral images. At step 1920, method 1900 may include correlating, using the computing device, a subsurface oral image with the aggregated oral image.

Still referring to FIG. 19, aggregated oral image may include a three-dimensional representation of oral tissue. In some embodiments, aggregating the aggregated oral image may additionally include identifying at least a common feature in a first oral image and a second oral image of the plurality of oral images and transforming one or more of the first oral image and the second oral image as a function of the at least a common feature. In some cases, aggregating the aggregated oral image further includes blending a demarcation between the first oral image and the second oral image. In some cases, blending the demarcation may include comparing pixel values between overlapping pixels in the first oral image and the second oral image and altering the demarcation as a function of the comparison. In some cases, altering the demarcation may include minimizing a difference in value between overlapping pixels between the first oral image and the second oral image along the demarcation.

Still referring to FIG. 19, in some embodiments, correlating the subsurface image with the aggregated oral image additionally includes identifying at least a common feature in the aggregated oral image and the subsurface oral image of the plurality of oral images and transforming one or more of the aggregated oral image and the subsurface oral image as a function of the at least a common feature.

Still referring to FIG. 19, in some embodiments, correspondence between the subsurface oral image and the aggregated oral image is within one or more of 500, 250, 150, 100, 50, or 25 micrometers. In some embodiments, correlating the subsurface oral image with the aggregated oral image may include inputting the subsurface oral image and the aggregated oral image into an image correspondence machine learning model and correlating the subsurface oral image and the aggregated oral image as a function of the subsurface oral image and the aggregated oral image and the image correspondence machine learning model. In some cases, aggregating the aggregated oral image may additionally include training the image aggregation machine learning model by inputting an image correspondence training set into a machine learning process, wherein the image correspondence training set correlates aggregated oral images to subsurface oral images and training the image correspondence metric machine learning model as a function of the image correspondence training set and the machine learning algorithm.

Figure 20:
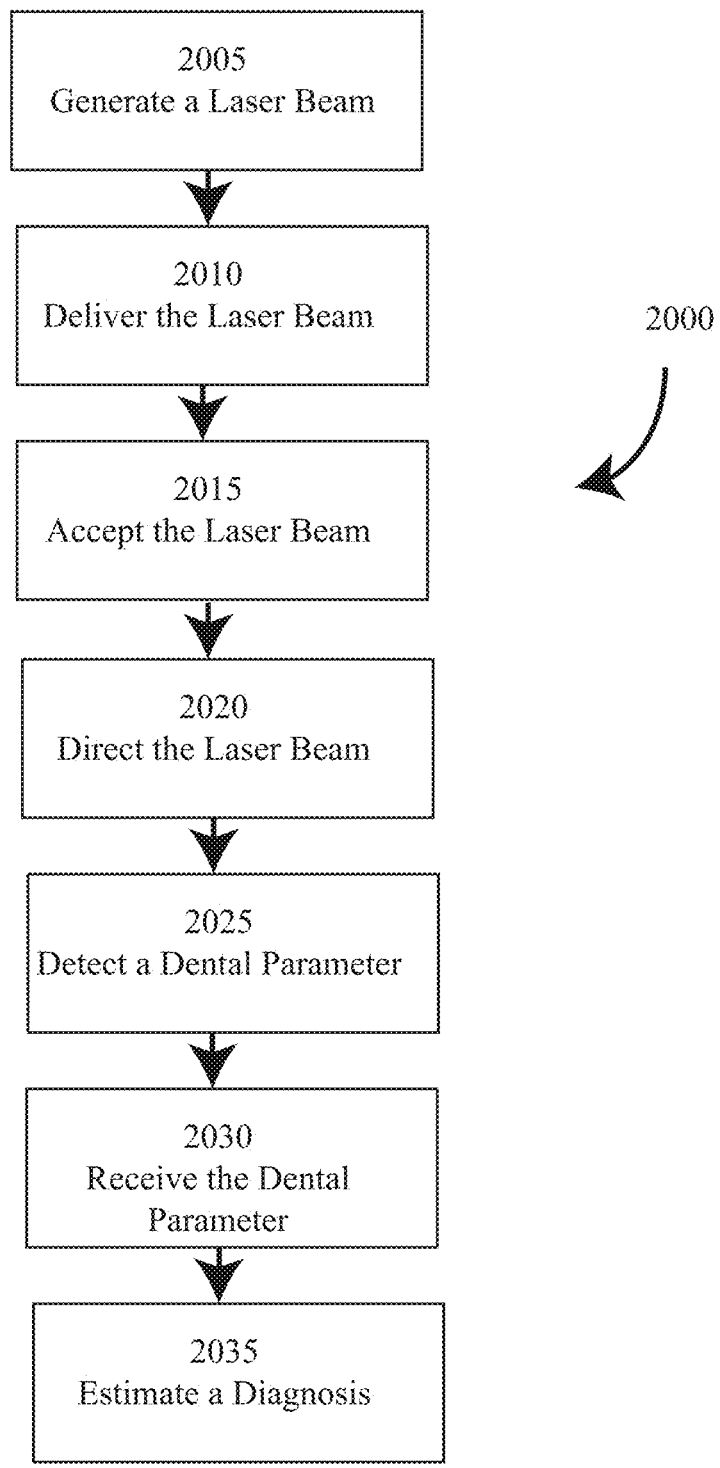
FIG. 20 illustrates a method of dental treatment and diagnosis by way of a flow diagram, according to some embodiments.

Referring now to FIG. 20, a method 2000 of dental treatment and diagnosis is illustrated by way of a flow diagram, according to some embodiments. At step 2005, method 2000 may include generating, using a laser, a laser beam as a function of a laser parameter. At step 2010, method 2000 may include delivering, using a beam delivery system, the laser beam from the laser. At step 2015, method 2000 may include accepting, using a hand piece, the laser beam from the beam delivery system. At step 2015, method 2000 may include directing, using the hand piece, the laser beam to dental tissue. At step 2020, method 2000 may include detecting, using a sensor, a dental parameter as a function of a dental phenomenon. At step 2025, method 2000 may include receiving, using a computing device, the dental parameter from the sensor. At step 2030, method 2000 may include estimating, using the computing device, a diagnosis as a function of the dental parameter.

Still referring to FIG. 20, in some embodiments, sensor may include a camera and the dental parameter comprises an image of oral tissue. In some cases, the camera is located proximal to the hand piece, and the method further comprises facilitating, using the hand piece, an optical path between the oral tissue and the camera.

Still referring to FIG. 20, in some embodiments, diagnosis may be a function of one or more of alignment trend, attrition trend, discoloration trend, or decay trend. In some embodiments, method 2000 may additionally include scanning, using a beam scanner of the beam delivery system, the laser beam as a function of a scan parameter and controlling, using the computing device, the scan parameter.

Still referring to FIG. 20, in some embodiments, method may additionally include controlling, using the computing device, the laser parameter. In some embodiments, estimating the diagnosis may include inputting the dental parameter to a diagnosis machine learning model and estimating the diagnosis using the diagnosis machine learning model. In some cases, estimating the diagnosis may additionally include inputting diagnostic training data into a machine learning processes, wherein the diagnostic training data correlates dental parameters to diagnosis and training the diagnostic machine learning model, using the diagnostic training data. In some cases, estimating the diagnosis may additionally include classifying the dental parameter and selecting the diagnostic training data from a plurality of training data as a function of the classification of the dental parameter. In some cases, classifying the dental parameter is performed as a function of patient information.

Figure 21:
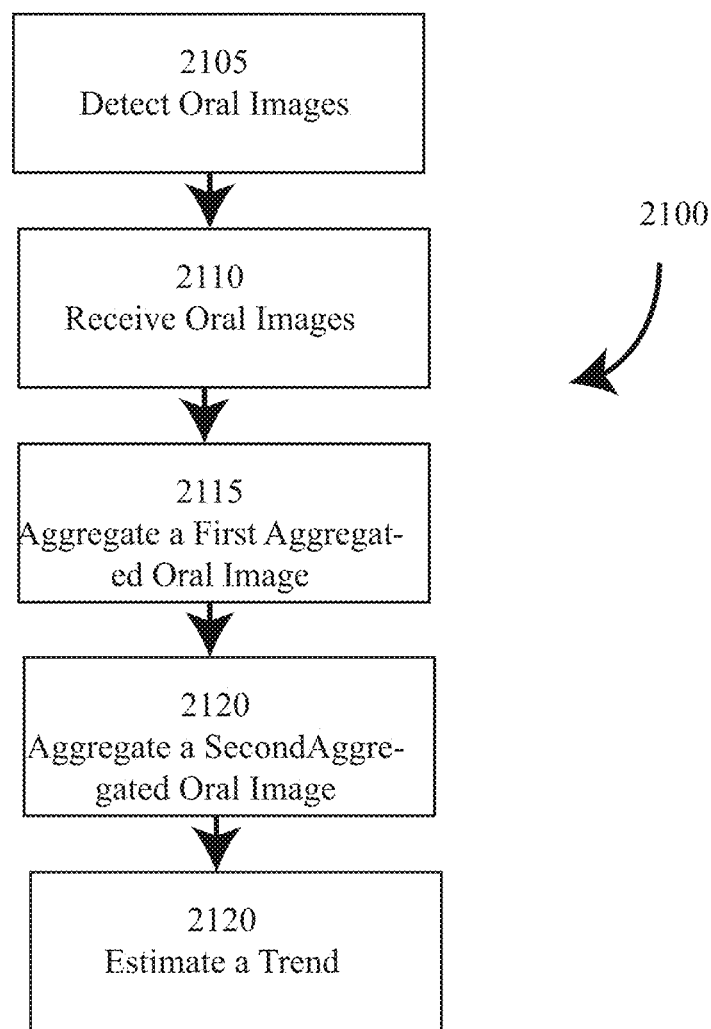
FIG. 21 illustrates a method of estimating a trend associated with dental tissue by way of a flow diagram, according to some embodiments.

Referring now to FIG. 21, a method 2100 of estimating a trend associated with dental tissue is illustrated by way of a flow diagram, according to some embodiments. At step 2105, method 2100 may include periodically detecting, using a sensor, the plurality of oral images as a function of the schedule. At step 2110, method 2100 may include receiving, using a computing device, the plurality of oral images from the sensor. At step 2115, method 2100 may include aggregating, using the computing device, a first aggregated oral image as a function of a first plurality of oral images at a first time. At step 2120, method 2100 may include aggregating, using the computing device, a second aggregated oral image as a function of a second plurality of oral images at a second time. At step 2125, method 2100 may include estimating, using the computing device, a future bite arrangement as a function of the first aggregated oral image and the second aggregated oral image.

Still referring to FIG. 21, method 2100 may additionally include scheduling, using a scheduling system, a patient for detecting a plurality of oral images representing a plurality of exposed tooth surfaces on a plurality of the patient's teeth. In some embodiments, patient includes a pediatric patient. In some cases, the pediatric patient has deciduous teeth.

Still referring to FIG. 21, in some embodiments, trend includes one or more of an attrition trend, a future bite arrangement trend, an alignment trend, a decay trend, or a discoloration trend. In some embodiments, estimating the trend may additionally include quantifying a first oral metric as a function of the first plurality of oral images, quantifying a second or metric as a function of the second plurality of oral images, and estimating the trend as a function of the first oral metric and the second oral metric. In some cases, quantifying the first oral metric may additionally include inputting into an oral metric machine learning model at least one image from the first plurality of oral images and outputting the first oral metric from the oral metric machine learning model as a function of the at least one image from the first plurality of oral images. In some cases, quantifying the first oral metric may additionally include receiving an oral metric machine learning training set that correlates oral metrics to oral images and training the oral metric machine learning model as a function of the oral metric machine learning training set. In some cases, estimating the trend may additionally include inputting the first oral metric and the second oral metric into a prediction machine learning process and outputting the trend as a function of the prediction machine learning process, the first oral metric, and the second oral metric. In some cases, estimating the trend may additionally include receiving a prediction training set that includes longitudinal oral metrics, training a prediction machine learning model as a function of prediction training set and a machine learning algorithm, inputting the first oral metric and the second oral metric into a prediction machine learning model, and outputting the trend as a function of the prediction machine learning model, the first oral metric, and the second oral metric.

The foregoing has been a detailed description of illustrative embodiments of the invention. Various modifications and additions can be made without departing from the spirit and scope of this invention. Features of each of the various embodiments described above may be combined with features of other described embodiments as appropriate to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within the ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. A system for dental treatment and verification, the system comprising:
   a laser configured to generate a laser beam as a function of at least a laser parameter;
   a beam delivery system configured to deliver the laser beam from the laser, the beam delivery system comprising a beam scanner configured to scan a position of the laser beam on dental tissue as a function of at least a scan parameter;
   a hand piece configured to accept the laser beam from the beam delivery system and direct the laser beam to the dental tissue;
   at least a sensor configured to detect at least a treatment parameter as a function of at least a treatment phenomenon, during the dental treatment, wherein the at least a sensor comprises:
      at least a camera configured to detect at least a treatment parameter comprising an image of at least a portion of the dental tissue concurrently with the dental treatment of the dental tissue, wherein the image includes an existing dental restoration; and
   a computing device, in communication with the laser, the beam scanner, and the at least a sensor, configured to:
      control the laser using the at least a laser parameter;
      control the beam scanner using the at least a scan parameter;
      controlling each of the at least a laser parameter and the at least a scan parameter to effect the dental treatment, wherein the dental treatment comprises dental laser cleaning;
      receive the treatment parameter from the at least a sensor;
      automatically determine aggregated treated surfaces as a function of the at least a treatment parameter and the at least a laser parameter;
      generate a 3D representation of the aggregated treated surfaces as a function of the aggregated treated surfaces, the at least a treatment parameter, and the at least a laser parameter; and
      display the 3D representation of the aggregated treated surfaces to a user of the system during the dental laser cleaning.

2. The system of claim 1, wherein:
   the at least a sensor comprises a position sensor, comprising a rotary encoder configured to detect rotary position of a component of the beam delivery system; and
   the at least a treatment parameter represents a treated location derived from the rotary position of the component of the beam delivery system.

3. The system of claim 1, wherein the computing device is further configured to:
   generate a treatment metric as a function of one or more of the at least a treatment parameter and the aggregated treated surfaces; and
   communicate the treatment metric to a remote device.

4. The system of claim 3, wherein generating the treatment metric comprises:
   inputting one or more of the at least a treatment parameter and a representation of the aggregated treated surfaces into a treatment metric machine learning model; and
   outputting the treatment metric as a function of the treatment metric machine learning model and one or more of the at least a treatment parameter and the representation of the aggregated treated surfaces.

5. The system of claim 4 wherein generating the treatment metric further comprises:
training the treatment metric machine learning model by:
inputting a treatment metric training set into a machine learning algorithm, wherein the treatment metric training set correlates treatment metrics to one or more of the at least a treatment parameter and the representation of the aggregated treated surfaces; and
training the treatment metric machine learning model as a function of the treatment metric training set and the machine learning algorithm.

6. The system of claim 3 wherein the treatment metric is related to the laser treatment.

7. A method of dental treatment and verification, the method comprising:
generating, using a laser, a laser beam as a function of at least a laser parameter;
delivering, using a beam delivery system comprising a beam scanner, the laser beam from the laser;
scanning, using the beam scanner of the beam delivery system, a position of the laser beam on dental tissue as a function of at least a scan parameter;
accepting, using a hand piece, the laser beam from the beam delivery system
directing, using the hand piece, the laser beam to the dental tissue;
detecting, using at least a sensor comprising a camera, at least a treatment parameter as a function of at least a treatment phenomenon, during the dental laser treatment;
detecting, using the at least a camera, the at least a treatment parameter comprising an image of at least a portion of the dental tissue concurrently with the dental laser treatment of the dental tissue, wherein the image includes an existing dental restoration;
controlling, using a computing device in communication with the laser, the beam scanner, and the at least a sensor, the laser using the at least a laser parameter;
controlling, using the computing device, the beam scanning using the at least a scan parameter;
controlling, using the computing device, each of the at least a laser parameter and the at least a scan parameter to effect the dental treatment, wherein the dental treatment includes dental laser cleaning;
receiving, using the computing device, the treatment parameter from the at least a sensor;
automatically determining, using the computing device, aggregated treated surfaces as a function of the at least a treatment parameter and the at least a laser parameter;
generating, using the computing device, a 3D representation of the aggregated treated surfaces as a function of the aggregated treated surfaces, the at least a treatment parameter, and the at least a laser parameter; and
displaying, using the computing device, the 3D representation of the aggregated treated surfaces to a user of the system during the dental laser cleaning.

8. The method of claim 7, wherein:
the at least a sensor comprises a position sensor, comprising a rotary encoder configured to detect rotary position of a component of the beam delivery system; and;
the at least a treatment parameter represents a treated location derived from the rotary position of the component of the beam delivery system.

9. The method of claim 7, further comprising:
generating, using the computing device, a treatment metric as a function of one or more of the at least a treatment parameter and the aggregated treated surfaces; and
communicating, using the computing device, the treatment metric to a remote device.

10. The method of claim 9, wherein generating the treatment metric comprises:
inputting one or more of the at least a treatment parameter and a representation of the aggregated treated surfaces into a treatment metric machine learning model; and
outputting the treatment metric as a function of the treatment metric machine learning model and one or more of the at least a treatment parameter and the representation of the aggregated treated surfaces.

11. The method of claim 10 wherein generating the treatment metric further comprises:
training the treatment metric machine learning model by:
inputting a treatment metric training set into a machine learning algorithm, wherein the treatment metric training set correlates treatment metrics to one or more of the at least a treatment parameter and the representation of the aggregated treated surfaces; and
training the treatment metric machine learning model as a function of the treatment metric training set and the machine learning algorithm.

12. The method of claim 9 wherein, the treatment metric is related to the dental treatment.

13. The system of claim 1, wherein the computing device is further configured to automatically chart a size, location, and surface of the existing dental restoration, and automatically charting includes classifying the at least a treatment parameter comprising the image of the existing dental restoration to a type of restoration.

14. The system of claim 13, wherein classifying the at least a treatment parameter comprising the image of the existing dental restoration to the type of restoration comprises:
inputting the at least a treatment parameter comprising the image of the existing dental restoration into a classifier comprising a machine learning model; and
classifying the type of restoration as a function of the at least a treatment parameter comprising the image of the existing dental restoration and the classifier comprising the machine learning model.

15. The method of claim 7, further comprising automatically charting, using the computing device, a size, location, and surface of the existing dental restoration, wherein automatically charting includes classifying the at least a treatment parameter comprising the image of the existing dental restoration to a type of restoration.

16. The method of claim 15, wherein classifying the at least a treatment parameter comprising the image of the existing dental restoration to the type of restoration comprises:
inputting the at least a treatment parameter comprising the image of the existing dental restoration into a classifier comprising a machine learning model; and
classifying the type of restoration as a function of the at least a treatment parameter comprising the image of the existing dental restoration and the classifier comprising the machine learning model.

17. The system of claim 1, wherein the computing device is further configured to differentiate between treated surfaces and untreated surfaces on the 3D representation of the aggregated treated surfaces as a function of the aggregated treated surfaces, the at least a treatment parameter, and the at least a laser parameter.

18. The system of claim 1, wherein the dental laser cleaning treatment is a prophylactic treatment configured to retreat a patient periodically at least once a year.

19. The method of claim 7, further comprising differentiating, using the computing device, between treated surfaces and untreated surfaces on the 3D representation of the aggregated treated surfaces as a function of the aggregated treated surfaces, the at least a treatment parameter, and the at least a laser parameter.

20. The method of claim 7, wherein the dental laser cleaning treatment is a prophylactic treatment configured to retreat a patient periodically at least once a year.

* * * * *